(12) United States Patent
Marx et al.

(10) Patent No.: US 7,595,325 B2
(45) Date of Patent: Sep. 29, 2009

(54) SUBSTITUTED PYRROLO[2,3-D]PYRIMIDINE DERIVATIVES USEFUL IN CANCER TREATMENT

(75) Inventors: Matthew A. Marx, Waterford, CT (US); Jinshan Chen, Brookfield, CT (US); Susan LaGreca, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 375 days.

(21) Appl. No.: 11/140,411

(22) Filed: May 27, 2005

(65) Prior Publication Data

US 2006/0035912 A1 Feb. 16, 2006

Related U.S. Application Data

(60) Provisional application No. 60/574,859, filed on May 27, 2004.

(51) Int. Cl.
C07D 487/04 (2006.01)
A61K 31/519 (2006.01)
A61P 35/04 (2006.01)

(52) U.S. Cl. .................... 514/265.1; 544/280
(58) Field of Classification Search ............... 544/280; 514/265.1
See application file for complete search history.

(56) References Cited

U.S. PATENT DOCUMENTS

| | | | |
|---|---|---|---|
| 5,747,498 A | 5/1998 | Schnur et al. | |
| 6,001,839 A | 12/1999 | Calderwood et al. | |
| 6,051,577 A | 4/2000 | Altmann | |
| 6,492,383 B1 | 12/2002 | Munchhof et al. | |
| 2005/0037999 A1 | 2/2005 | La Greca et al. | |
| 2005/0130994 A1 | 6/2005 | Chen et al. | |

FOREIGN PATENT DOCUMENTS

| | | |
|---|---|---|
| EP | 0837063 | 4/1998 |
| EP | 0907649 | 4/1999 |
| WO | WO95/23141 | 8/1995 |
| WO | WO96/40142 | 12/1996 |
| WO | WO97/13771 | 4/1997 |
| WO | WO97/49688 | 12/1997 |
| WO | WO98/23613 | 6/1998 |
| WO | WO00/17202 | 3/2000 |
| WO | WO00/17203 | 3/2000 |
| WO | WO01/72751 | 10/2001 |
| WO | WO01/72778 | 10/2001 |
| WO | WO2004/013141 | 12/2004 |

OTHER PUBLICATIONS

Townsend, L., et al., "Synthesis, Antiproliferative, And Antiviral Activity Of Certain 4-Substituted And 4,5-Disubstituted 7-[1,3-Dihydroxy-2-propoxy)methyl]pyrrolo[2,3-*d*]pyrimidines," *J. Med. Chem.*, 1990, 1984-1992, vol. 33.

Ugarkar, b., et al., "Adenosine Kinase Inhibitors. 1. Synthesis, Enzyme Inhibition, and Antiseisure Activity Of 5-Iodotubercidin Analogues," *J. Med. Chem.*, 2000, 2883-2893, vol. 43, No. 15.

*Primary Examiner*—Brenda L Coleman
*Assistant Examiner*—Susanna Moore
(74) *Attorney, Agent, or Firm*—Bryan C. Zielinski; Suzanne M. Bates

(57) ABSTRACT

The invention relates to compounds of the formula 1

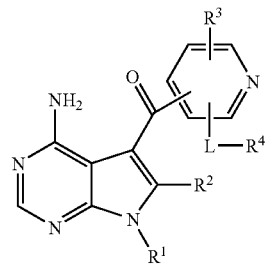

or a pharmaceutically acceptable salt, prodrug, solvate or hydrate thereof, wherein L, $R^1$, $R^2$, $R^3$ and $R^4$ are as defined herein. The invention also relates to pharmaceutical compositions containing the compounds of formula 1 and to methods of treating abnormal cell growth, such as cancer in a mammal by administering the compounds of formula 1.

6 Claims, No Drawings

SUBSTITUTED PYRROLO[2,3-D]PYRIMIDINE DERIVATIVES USEFUL IN CANCER TREATMENT

The entire disclosure of parent application No. 60/574,859 filed May 27, 2004 is fully incorporated herein by reference thereto.

This application claims priority to U.S. Provisional Application No. 60/574,859 filed May 27, 2004, the disclosure of which is incorporated into this application in its entirety.

BACKGROUND OF THE INVENTION

This invention relates to novel pyrrolopyrimidine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

It is known that a cell may become cancerous by virtue of the transformation of a portion of its DNA into an oncogene (i.e. a gene that upon activation leads to the formation of malignant tumor cells). Many oncogenes encode proteins, which are aberrant tyrosine kinases capable of causing cell transformation. Alternatively, the over expression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residue in proteins and hence to influence cell proliferation. The foregoing tyrosine kinases may be classified as growth factor receptor (e.g. TIE-2, TrkA, EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or over expressed in many human cancers such as brain, lung, squamous cell, bladder, gastric, breast, head and neck, esophageal, gynecological and thyroid cancers. Thus, it is believed that inhibitors of receptor tyrosine kinases, such as the compounds of the present invention, are useful as selective inhibitors of the growth of mammalian cancer cells.

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli.

The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovascularization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, therefore, useful in treating such disorders, and in other situations of inappropriate neovascularization. The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. Agents, such as the compounds of the present invention, that are capable of binding to or modulating the Tie-2 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

Patent publications referring to pyrrolopyrimidines as protein kinase inhibitors include the following: WO 01/72751 (published Oct. 4, 2001), WO 00/17203 and WO 00/17202 (both published Mar. 30, 2000), U.S. Pat. No. 6,001,839 (granted Dec. 14, 1999), and U.S. Pat. No. 6,051,577 (granted Apr. 18, 2000). WO 01/72778 (published Oct. 4, 2001) refers to polypeptides comprising the catalytic domain of a Tie-2 protein. U.S. Provisional Applications Ser. No. 60/434,568, filed Dec. 17, 2002, and Ser. No. 60/523,206 filed Nov. 18, 2003 refer to pyrrolopyrimidine derivatives useful in the treatment of hyperproliferative diseases, such as cancers.

Compounds that are useful in the treatment of hyperproliferative diseases are referred to the following patent publications: International patent application publication numbers WO 97/49688 (published Dec. 31, 1997), WO 98/23613 (published Jun. 4, 1998), WO 96/40142 (published Dec. 19, 1996), WO 97/13771 (published Apr. 17, 1997), and WO 95/23141 (published Aug. 31, 1995); European patent publication numbers EP 0837063 (published Apr. 22, 1998), and EP 0907649 (published Apr. 14, 1999); and U.S. Pat. Nos. 5,747,498 (granted May 5, 1998), and 6,492,383 (granted Dec. 10, 2002).

SUMMARY OF THE INVENTION

The present invention relates to a compound of the formula 1

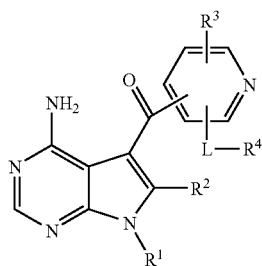

1 wherein:
L is —O—; —S—; —S(O)—; —S(O)$_2$—; —N(R)—; —N(C(O)OR)—; —N(C(O)R)—; —N(S(O)$_2$R)—; —C(O)N(R)—; —N(R)C(O)—; —N(R)S(O)—; —N(R)S(O)$_2$—; —OC(O)N(R)—; —N(R)C(O)N(R)—; —N(R)C(O)O—; —S(O)N(R)—; —S(O)$_2$N(R)—; or —N=; wherein each R independently is H, (C$_1$-C$_6$)alkylC(O), (C$_1$-C$_6$)alkyl, (C$_6$-C$_{10}$)aryl or (C$_1$-C$_{10}$)heteroaryl; wherein each of the aforesaid (C$_1$-C$_6$)alkylC(O), (C$_1$-C$_6$)alkyl, (C$_6$-C$_{10}$)aryl, and (C$_1$-C$_{10}$)heteroaryl groups is independently optionally substituted with 1 to 5 substituents independently selected from halogen, (C$_1$-C$_6$)alkyl and (C$_1$-C$_6$)alkoxy;
each of R$^1$ and R$^2$ is independently H, (C$_1$-C$_6$)alkyl, (C$_3$-C$_8$)cycloalkyl, (C$_6$-C$_{10}$)aryl, (C$_1$-C$_{10}$)heteroaryl, or (C$_1$-C$_{10}$)heterocycloalkyl; wherein each of the aforesaid (C$_1$-C$_6$)alkyl, (C$_3$-C$_8$)cycloalkyl, (C$_6$-C$_{10}$)aryl, (C$_1$-C$_{10}$)heteroaryl, and (C$_1$-C$_{10}$)heterocycloalkyl groups is independently optionally substituted with 1 to 5 (C$_1$-C$_6$) alkyl groups;
R$^3$ is H, (C$_1$-C$_6$)alkyl, (C$_3$-C$_8$)cycloalkyl, (C$_1$-C$_6$)alkoxy, —NH$_2$, —NH(C$_1$-C$_6$)alkyl, —N[(C$_1$-C$_6$)alkyl]$_2$, (C$_6$-C$_{10}$)aryl, (C$_1$-C$_{10}$)heteroaryl, or (C$_1$-C$_{10}$)heterocycloalkyl; wherein each of the aforesaid (C$_1$-C$_6$)alkyl, (C$_3$-C$_8$)cycloalkyl, (C$_6$-C$_{10}$)aryl, (C$_1$-C$_{10}$)heteroaryl, and (C$_1$-C$_{10}$)heterocycloalkyl groups is independently optionally substituted with 1 to 5 (C$_1$-C$_6$) alkyl groups;
R$^4$ is H, (C$_1$-C$_6$)alkyl, (C$_3$-C$_8$)cycloalkyl, —(CR$^5$R$^6$)$_t$(C$_6$-C$_{10}$)aryl, —(CR$^5$R$^6$)$_t$(C$_1$-C$_{10}$)heteroaryl, (C$_3$-C$_8$)heterocycloalkyl, or CR$^7$R$^8$; wherein R$^4$ is CR$^7$R$^8$ only when L is —N=; wherein t is an integer from 0 to 6; and each of the aforesaid (C$_1$-C$_6$)alkyl, (C$_3$-C$_8$)cycloalkyl, —(CR$^5$R$^6$)$_t$(C$_6$-C$_{10}$)aryl, —(CR$^5$R$^6$)$_t$(C$_1$-C$_{10}$)heteroaryl, and (C$_3$-C$_8$)heterocycloalkyl groups is independently optionally substituted with 1 to 5 R$^9$ groups;
each of R$^5$ and R$^6$ is independently selected from H and (C$_1$-C$_6$)alkyl;
each of R$^7$ and R$^8$ is independently (C$_1$-C$_6$)alkyl, (C$_3$-C$_8$)cycloalkyl, —(CR$^5$R$^6$)$_t$(C$_6$-C$_{10}$)aryl, —(CR$^5$R$^6$)$_t$(C$_1$-C$_{10}$)heteroaryl, or (C$_3$-C$_8$)heterocycloalkyl; or R$^7$ and R$^8$ may be taken together with the carbon atom to which they are attached form a (C$_3$-C$_8$)cycloalkyl, (C$_1$-C$_{10}$)heteroaryl, or a (C$_3$-C$_8$)heterocycloalkyl group; wherein t is an integer from 0 to 6; and each of the aforesaid (C$_1$-C$_6$)alkyl, (C$_3$-C$_8$)cycloalkyl, —(CR$^5$R$^6$)$_t$(C$_6$-C$_{10}$)aryl, (C$_1$-C$_{10}$)heteroaryl, —(CR$^5$R$^6$)$_t$(C$_1$-C$_{10}$)heteroaryl, and (C$_3$-C$_8$)heterocycloalkyl groups is optionally independently substituted with 1 to 5 R$^9$ groups;
each R$^9$ is independently halo, cyano, trifluoromethoxy, trifluoromethyl, (C$_1$-C$_6$)alkyl, (C$_2$-C$_6$)alkenyl, (C$_2$-C$_6$)alkynyl, or —(CR$^5$R$^6$)$_t$OR$^{10}$; t is independently an integer from 0 to 6; any of the aforesaid —(CR$^5$R$^6$)$_t$- moiety may optionally include a carbon-carbon double or triple bond where t is an integer from 2 to 6; and
each R$^{10}$ is independently hydrogen or (C$_1$-C$_6$)alkyl; and a pharmaceutically acceptable salt, prodrug, solvate or hydrate of the compound of formula 1.

One embodiment of the invention includes those compounds wherein formula 1 is formula 1A

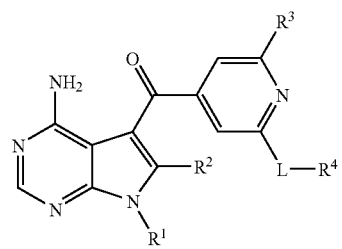

1A wherein L, R$^1$, R$^2$, R$^3$ and R$^4$ are as set forth for formula 1.

Other embodiments of the invention include those compounds of formula 1A wherein L is —N(R)—; —N(C(O)R)—; —N(R)C(O)N(R)—; or —N(R)S(O)$_2$—; wherein each R is independently H or (C$_1$-C$_6$)alkyl, wherein said C$_1$-C$_6$)alkyl is optionally substituted with 1-5 substituents independently selected from halogen, (C$_1$-C$_6$)alkyl and (C$_1$-C$_6$)alkoxy.

Other embodiments of the invention include those compounds of formula 1A wherein L is —N(R)C(O)N(R), wherein each R is independently H or (C$_1$-C$_6$)alkyl, wherein said C$_1$-C$_6$)alkyl is optionally substituted with 1 to 5 substituents independently selected from halogen, (C$_1$-C$_6$)alkyl and (C$_1$-C$_6$)alkoxy.

Other embodiments of the invention include those compounds of formula 1A wherein L is —N(R)C(O)N(R) wherein each R is independently H or (C$_1$-C$_6$)alkyl, wherein said C$_1$-C$_6$)alkyl is optionally substituted with 1-5 substituents independently selected from halogen, (C$_1$-C$_6$)alkyl and (C$_1$-C$_6$)alkoxy; R$^1$ is (C$_1$-C$_6$)alkyl; R$^2$ is H; R$^3$ is H, (C$_1$-C$_6$) alkyl or (C$_1$-C$_6$)alkoxy; and R$^4$ is (C$_6$-C$_{10}$)aryl; wherein each of the aforesaid (C$_1$-C$_6$)alkyl and (C$_6$-C$_{10}$)alkoxy groups of the R$^1$ and R$^3$ substituents is optionally independently substituted with 1 to 5 (C$_1$-C$_6$)alkyl groups and said (C$_6$-C$_{10}$)aryl group is optionally substituted with 1 to 5 R$^9$ groups.

Other embodiments of the invention include those compounds of formula 1A wherein L is —N(R)S(O)$_2$— wherein each R is independently H or (C$_1$-C$_6$)alkyl, wherein said (C$_1$-C$_6$)alkyl is optionally substituted with 1 to 5 substituents independently selected from halogen, (C$_1$-C$_6$)alkyl and (C$_1$-C$_6$)alkoxy.

Other embodiments of the invention include those compounds of formula 1A wherein L is —N(R)S(O)$_2$— wherein R is H or (C$_1$-C$_6$)alkyl, wherein said (C$_1$-C$_6$)alkyl is optionally substituted with 1-5 substituents independently selected from halogen, (C$_1$-C$_6$)alkyl and (C$_1$-C$_6$)alkoxy; R$^1$ is (C$_1$-C$_6$) alkyl; R$^2$ is H; R$^3$ is H, (C$_1$-C$_6$)alkyl or (C$_1$-C$_6$)alkoxy; and R$^4$ is ($C_6$-$C_{10}$)aryl; wherein each of the aforesaid ($C_1$-$C_6$)alkyl and ($C_6$-$C_{10}$)alkoxy groups of the $R^1$ and $R^3$ substituents is optionally independently substituted with 1 to 5 ($C_1$-$C_6$)alkyl groups and said ($C_6$-$C_{10}$)aryl group is optionally substituted with 1 to 5 $R^9$ groups.

Other embodiments of the invention include those compounds of formula 1A wherein L is —N(R)—, wherein R is H or ($C_1$-$C_6$)alkyl, wherein said ($C_1$-$C_6$)alkyl is optionally substituted with 1 to 5 substituents independently selected from halogen, ($C_1$-$C_6$)alkyl and ($C_1$-$C_6$)alkoxy.

Other embodiments of the invention include those compounds of formula 1A wherein L is —N(R)—, wherein R is H or ($C_1$-$C_6$)alkyl, wherein said ($C_1$-$C_6$)alkyl is optionally substituted with 1-5 substituents independently selected from halogen, ($C_1$-$C_6$)alkyl and ($C_1$-$C_6$)alkoxy; $R^1$ is ($C_1$-$C_6$) alkyl; $R^2$ is H; $R^3$ is H or ($C_1$-$C_6$)alkyl; and $R^4$ is H; wherein said ($C_1$-$C_6$)alkyl of said $R^1$ and $R^3$ substituents is optionally substituted with 1 to 5 ($C_1$-$C_6$)alkyl groups.

Other embodiments of the invention include those compounds wherein the formula 1 is represented by formula 1B wherein L, $R^1$, $R^2$, $R^3$ and $R^4$ are as set forth for formula 1.

Other embodiments of the invention include those compounds of the formula 1B, wherein L is —N(R)—; —N(C(O)R)—; —N(R)C(O)N(R)—; or —N(R)S(O)$_2$—; wherein each R is independently H or ($C_1$-$C_6$)alkyl, wherein said ($C_1$-$C_6$)alkyl is optionally substituted with 1 to 5 substituents independently selected from halogen, ($C_1$-$C_6$)alkyl and ($C_1$-$C_6$)alkoxy.

Other embodiments of the invention include those compounds of the formula 1B, wherein L is —N(R)C(O)N(R)—; wherein each R is independently H or ($C_1$-$C_6$)alkyl, wherein said ($C_1$-$C_6$)alkyl is optionally substituted with 1 to 5 substituents independently selected from halogen, ($C_1$-$C_6$)alkyl and ($C_1$-$C_6$)alkoxy.

Other embodiments of the invention include those compounds of the formula 1B, wherein L is —N(R)C(O)N(R)—; wherein each R is independently H or ($C_1$-$C_6$)alkyl, wherein said ($C_1$-$C_6$)alkyl is optionally substituted with 1-5 substituents independently selected from halogen, ($C_1$-$C_6$)alkyl and ($C_1$-$C_6$)alkoxy; $R^1$ is ($C_1$-$C_6$)alkyl; $R^2$ is H; $R^3$ is H; and $R^4$ is ($C_6$-$C_{10}$)aryl; wherein said ($C_1$-$C_6$)alkyl group is optionally substituted with 1 to 5 ($C_1$-$C_6$)alkyl groups; and said ($C_6$-$C_{10}$) aryl group is optionally substituted with 1 to 5 $R^9$ groups.

Other embodiments of the invention include those compounds of the formula 1B, wherein L is —N(R)S(O)$_2$—; wherein R is H or ($C_1$-$C_6$)alkyl, wherein said ($C_1$-$C_6$)alkyl is optionally substituted with 1 to 5 substituents independently selected from halogen, ($C_1$-$C_6$)alkyl and ($C_1$-$C_6$)alkoxy;

Other embodiments of the invention include those compounds of the formula 1B, wherein L is —N(R)S(O)$_2$—; $R^1$ is ($C_1$-$C_6$)alkyl; $R^2$ is H; $R^3$ is H; and $R^4$ is ($C_6$-$C_{10}$)aryl; wherein said ($C_1$-$C_6$)alkyl group is optionally substituted with 1 to 5 ($C_1$-$C_6$)alkyl groups; and said ($C_6$-$C_{10}$)aryl group is optionally substituted with 1 to 5 $R^9$ groups.

Other embodiments of the invention include those compounds of the formula 1B, wherein L is —N(R)—; wherein R is H or ($C_1$-$C_6$)alkyl, wherein said ($C_1$-$C_6$)alkyl is optionally substituted with 1-5 substituents independently selected from halogen, ($C_1$-$C_6$)alkyl and ($C_1$-$C_6$)alkoxy.

Other embodiments of the invention include those compounds of the formula 1B, wherein L is —N(R)—; wherein R is H or ($C_1$-$C_6$)alkyl, wherein said ($C_1$-$C_6$)alkyl is optionally substituted with 1-5 substituents independently selected from halogen, ($C_1$-$C_6$)alkyl and ($C_1$-$C_6$)alkoxy; $R^1$ is ($C_1$-$C_6$) alkyl; and $R^2$, $R^3$ and $R^4$ are all H; wherein said ($C_1$-$C_6$)alkyl of said $R^1$ substituent is optionally independently substituted with 1 to 5 ($C_1$-$C_6$)alkyl groups.

Other embodiments of the invention include those compounds wherein formula 1 is represented by formula 1C wherein L, $R^1$, $R^2$, $R^3$ and $R^4$ are as set forth for formula 1.

Other embodiments of the invention include those compounds of the formula 1C wherein L is —N(R)—; —N(C(O)R)—; —N(R)C(O)N(R)—; or —N(R)S(O)$_2$—; wherein each R is independently H or ($C_1$-$C_6$)alkyl, wherein said $C_1$-$C_6$)alkyl is optionally substituted with 1-5 substituents independently selected from halogen, ($C_1$-$C_6$)alkyl and ($C_1$-$C_6$)alkoxy.

Other embodiments of the invention include those compounds of the formula 1C wherein L is —N(R)C(O)N(R)—; wherein each R is independently H or ($C_1$-$C_6$)alkyl, wherein said $C_1$-$C_6$)alkyl is optionally substituted with 1 to 5 substituents independently selected from halogen, ($C_1$-$C_6$)alkyl and ($C_1$-$C_6$)alkoxy.

Other embodiments of the invention include those compounds of the formula 1C wherein L is —N(R)C(O)N(R)—; wherein each R is independently H or ($C_1$-$C_6$)alkyl, wherein said $C_1$-$C_6$)alkyl is optionally substituted with 1-5 substituents independently selected from halogen, ($C_1$-$C_6$)alkyl and ($C_1$-$C_6$)alkoxy; $R^1$ is ($C_1$-$C_6$)alkyl; $R^2$ is H; $R^3$ is H; and $R^4$ is ($C_6$-$C_{10}$)aryl; wherein said ($C_1$-$C_6$)alkyl of said $R^1$ substituent is optionally substituted with 1 to 5 ($C_1$-$C_6$)alkyl groups; and said ($C_6$-$C_{10}$)aryl group is optionally substituted with 1 to 5 $R^9$ groups.

Other embodiments of the invention include those compounds of the formula 1C wherein L is —N(R)S(O)$_2$—; wherein R is H or ($C_1$-$C_6$)alkyl, wherein said $C_1$-$C_6$)alkyl is optionally substituted with 1 to 5 substituents independently selected from halogen, ($C_1$-$C_6$)alkyl and ($C_1$-$C_6$)alkoxy.

Other embodiments of the invention include those compounds of the formula 1C wherein L is —N(R)S(O)$_2$—; wherein R is H or ($C_1$-$C_6$)alkyl, wherein said $C_1$-$C_6$)alkyl is optionally substituted with 1-5 substituents independently selected from halogen, ($C_1$-$C_6$)alkyl and ($C_1$-$C_6$)alkoxy; $R^1$ is ($C_1$-$C_6$)alkyl; $R^2$ is H; $R^3$ is H; and $R^4$ is ($C_6$-$C_{10}$)aryl; wherein said ($C_1$-$C_6$)alkyl of said $R^1$ substituent is optionally substituted with 1 to 5 ($C_1$-$C_6$)alkyl groups; and said ($C_6$-$C_{10}$) aryl is optionally substituted with 1 to 5 $R^9$ groups.

Other embodiments of the invention include those compounds of the formula 1C wherein L is —N(R)—; wherein R is H or (C$_1$-C$_6$)alkyl, wherein said C$_1$-C$_6$ alkyl is optionally substituted with 1 to 5 substituents independently selected from halogen, (C$_1$-C$_6$)alkyl and (C$_1$-C$_6$)alkoxy; R$^1$ is (C$_1$-C$_6$)alkyl.

Other embodiments of the invention include those compounds of the formula 1C wherein L is —N(R)—; wherein R is H or (C$_1$-C$_6$)alkyl, wherein said C$_1$-C$_6$ alkyl is optionally substituted with 1-5 substituents independently selected from halogen, (C$_1$-C$_6$)alkyl and (C$_1$-C$_6$)alkoxy; R$^1$ is (C$_1$-C$_6$)alkyl; and R$^2$, R$^3$ and R$^4$ are all H; wherein said (C$_1$-C$_6$)alkyl of said R$^1$ substituent is optionally independently substituted with 1 to 5 (C$_1$-C$_6$)alkyl groups.

Other embodiments of the invention include those compounds wherein formula 1 is represented by formula 1D

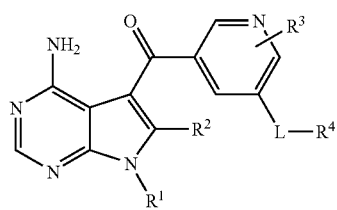

1D wherein L, R$^1$, R$^2$, R$^3$ and R$^4$ are as set forth for formula 1.

Other embodiments of the invention include those compounds of the formula 1D wherein L is —N(R)—; —N(C(O)R)—; —N(R)C(O)N(R)—; —N(R)S(O)$_2$—; or —N═; wherein each R is independently H or (C$_1$-C$_6$)alkyl, wherein said C$_1$-C$_6$ alkyl is optionally substituted with 1 to 5 substituents independently selected from halogen, (C$_1$-C$_6$)alkyl and (C$_1$-C$_6$)alkoxy.

Other embodiments of the invention include those compounds of the formula 1D wherein L is —N(R)C(O)N(R)—; wherein each R is independently H or (C$_1$-C$_6$)alkyl, wherein said C$_1$-C$_6$ alkyl is optionally substituted with 1 to 5 substituents independently selected from halogen, (C$_1$-C$_6$)alkyl and (C$_1$-C$_6$)alkoxy.

Other embodiments of the invention include those compounds of the formula 1D wherein L is —N(R)C(O)N(R)—; wherein each R is independently H or (C$_1$-C$_6$)alkyl, wherein said C$_1$-C$_6$ alkyl is optionally substituted with 1 to 5 substituents independently selected from halogen, (C$_1$-C$_6$)alkyl and (C$_1$-C$_6$)alkoxy; R$^1$ is (C$_1$-C$_6$)alkyl; R$^2$ is H; R$^3$ is H; and R$^4$ is (C$_3$-C$_8$)cycloalkyl or (C$_6$-C$_{10}$)aryl; wherein said (C$_1$-C$_6$)alkyl of said R$^1$ substituent is optionally substituted with 1 to 5 (C$_1$-C$_6$)alkyl groups and said (C$_3$-C$_8$)cycloalkyl and (C$_6$-C$_{10}$)aryl of said R$^4$ substituents are optionally independently substituted with 1 to 5 R$^9$ groups.

Other embodiments of the invention include those compounds of the formula 1D wherein L is —N(R)S(O)$_2$—; wherein R is H or (C$_1$-C$_6$)alkyl, wherein said C$_1$-C$_6$ alkyl is optionally substituted with 1 to 5 substituents independently selected from halogen, (C$_1$-C$_6$)alkyl and (C$_1$-C$_6$)alkoxy.

Other embodiments of the invention include those compounds of the formula 1D wherein L is —N(R)S(O)$_2$—; R$^1$ is (C$_1$-C$_6$)alkyl; R$^2$ is H; R$^3$ is H; and R$^4$ is —(CR$^5$R$^6$)$_t$(C$_1$-C$_{10}$)heteroaryl or (C$_6$-C$_{10}$)aryl; wherein said (C$_1$-C$_6$)alkyl of said R$^1$ substituent is optionally substituted with 1 to 5 (C$_1$-C$_6$)alkyl groups; and said —(CR$^5$R$^6$)$_t$(C$_1$-C$_{20}$)heteroaryl and (C$_6$-C$_{10}$)aryl of said R$^4$ substituent are optionally independently substituted with 1 to 5 R$^9$ groups.

Other embodiments of the invention include those compounds of the formula 1D wherein L is —N(R)—; wherein R is H or (C$_1$-C$_6$)alkyl, wherein said C$_1$-C$_6$ alkyl is optionally substituted with 1 to 5 substituents independently selected from halogen, (C$_1$-C$_6$)alkyl and (C$_1$-C$_6$)alkoxy.

Other embodiments of the invention include those compounds of the formula 1D wherein L is —N(R)—; wherein R is H or (C$_1$-C$_6$)alkyl, wherein said C$_1$-C$_6$ alkyl is optionally substituted with 1-5 substituents independently selected from halogen, (C$_1$-C$_6$)alkyl and (C$_1$-C$_6$)alkoxy; R$^1$ is (C$_1$-C$_6$)alkyl; and R$^2$, R$^3$ and R$^4$ are all H; wherein said (C$_1$-C$_6$)alkyl of said R$^1$ substituent is optionally independently substituted with 1 to 5 (C$_1$-C$_6$)alkyl groups.

Other embodiments of the invention include those compounds of the formula 1D wherein L is —N═.

Other embodiments of the invention include those compounds of the formula 1D wherein L is —N═; R$^1$ is (C$_1$-C$_6$)alkyl; R$^2$ and R$^3$ are H; and R$^4$ is CR$^7$R$^8$ wherein R$^7$ and R$^8$ are independently —(CR$^5$R$^6$)$_t$(C$_6$-C$_{10}$)aryl.

Other embodiments of the invention include those compounds of the formula 1D wherein L is —N(C(O)R)—.

Other embodiments of the invention include those compounds of the formula 1D wherein L is —N(C(O)R)—; R$^1$ is (C$_1$-C$_6$)alkyl; R$^2$ is H; R$^3$ is H; and R$^4$ is (C$_6$-C$_{10}$)aryl; wherein said (C$_1$-C$_6$)alkyl is optionally substituted with 1 to 5 (C$_1$-C$_6$)alkyl groups and said (C$_6$-C$_{10}$)aryl is optionally substituted with 1 to 5 R$^9$ groups.

Specific preferred compound of formula 1 are selected from the group consisting of:

N-[5-(4-Amino-7-isopropyl-7H-pyrrolo[2,3-d]pyrimidine-5-carbonyl)-pyridin-3-yl]-3-trifluoromethyl-benzenesulfonamide;

1-[5-(4-Amino-7-isopropyl-7H-pyrrolo[2,3-d]pyrimidine-5-carbonyl)-pyridin-3-yl]-3-(3-chloro-phenyl)-urea;

1-[5-(4-Amino-7-isopropyl-7H-pyrrolo[2,3-d]pyrimidine-5-carbonyl)-pyridin-3-yl]-3-(3,5-dimethoxy-phenyl)-urea;

N-[5-(4-Amino-7-isopropyl-7H-pyrrolo[2,3-d]pyrimidine-5-carbonyl)-pyridin-3-yl]-3,5-dichloro-benzenesulfonamide;

N-[5-(4-Amino-7-isopropyl-7H-pyrrolo[2,3-d]pyrimidine-5-carbonyl)-pyridin-3-yl]-2,4-dichloro-benzenesulfonamide;

1-[5-(4-Amino-7-isopropyl-7H-pyrrolo[2,3-d]pyrimidine-5-carbonyl)-pyridin-3-yl]-3-cyclohexyl-urea;

1-[5-(4-Amino-7-isopropyl-7H-pyrrolo[2,3-d]pyrimidine-5-carbonyl)-pyridin-3-yl]-3-(2-fluoro-phenyl)-urea;

1-[5-(4-Amino-7-isopropyl-7H-pyrrolo[2,3-d]pyrimidine-5-carbonyl)-pyridin-3-yl]-3-(2-methoxy-5-methyl-phenyl)-urea;

1-[5-(4-Amino-7-methyl-7H-pyrrolo[2,3-d]pyrimidine-5-carbonyl)-pyridin-3-yl]-3-(2,4-dimethyl-phenyl)-urea;

1-[5-(4-Amino-7-methyl-7H-pyrrolo[2,3-d]pyrimidine-5-carbonyl)-pyridin-3-yl]-3-(4-methoxy-phenyl)-urea;

1-[5-(4-Amino-7-methyl-7H-pyrrolo[2,3-d]pyrimidine-5-carbonyl)-pyridin-3-yl]-3-(2-fluoro-5-methyl-phenyl)-urea;

1-[5-(4-Amino-7-methyl-7H-pyrrolo[2,3-d]pyrimidine-5-carbonyl)-pyridin-3-yl]-3-(2-chloro-phenyl)-urea;

1-[5-(4-Amino-7-methyl-7H-pyrrolo[2,3-d]pyrimidine-5-carbonyl)-pyridin-3-yl]-3-(3-chloro-phenyl)-urea;

N-[5-(4-Amino-7-methyl-7H-pyrrolo[2,3-d]pyrimidine-5-carbonyl)-pyridin-3-yl]-3-chloro-4-methyl-benzenesulfonamide;

1-[5-(4-Amino-7-methyl-7H-pyrrolo[2,3-d]pyrimidine-5-carbonyl)-pyridin-3-yl]-3-(4-chloro-phenyl)-urea;

N-[5-(4-Amino-7-methyl-7H-pyrrolo[2,3-d]pyrimidine-5-carbonyl)-pyridin-3-yl]-3-chloro-4-fluoro-benzenesulfonamide;
1-[5-(4-Amino-7-methyl-7H-pyrrolo[2,3-d]pyrimidine-5-carbonyl)-pyridin-3-yl]-3-(3,5-difluoro-phenyl)-urea;
N-[5-(4-Amino-7-methyl-7H-pyrrolo[2,3-d]pyrimidine-5-carbonyl)-pyridin-3-yl]-3-trifluoromethyl-benzenesulfonamide;
1-[5-(4-Amino-7-methyl-7H-pyrrolo[2,3-d]pyrimidine-5-carbonyl)-pyridin-3-yl]-3-(3,4-difluoro-phenyl)-urea;
N-[5-(4-Amino-7-methyl-7H-pyrrolo[2,3-d]pyrimidine-5-carbonyl)-pyridin-3-yl]-2,5-dichloro-benzenesulfonamide;
1-[5-(4-Amino-7-isopropyl-7H-pyrrolo[2,3-d]pyrimidine-5-carbonyl)-pyridin-3-yl]-3-(2,3-dichloro-phenyl)-urea;
1-[5-(4-Amino-7-methyl-7H-pyrrolo[2,3-d]pyrimidine-5-carbonyl)-pyridin-3-yl]-3-(2,6-difluoro-phenyl)-urea;
N-[5-(4-Amino-7-methyl-7H-pyrrolo[2,3-d]pyrimidine-5-carbonyl)-pyridin-3-yl]-3,5-dichloro-benzenesulfonamide;
N-[5-(4-Amino-7-isopropyl-7H-pyrrolo[2,3-d]pyrimidine-5-carbonyl)-pyridin-3-yl]-3,5-difluoro-benzenesulfonamide;
1-[5-(4-Amino-7-isopropyl-7H-pyrrolo[2,3-d]pyrimidine-5-carbonyl)-pyridin-3-yl]-3-(2-fluoro-5-methyl-phenyl)-urea;
1-[5-(4-Amino-7-isopropyl-7H-pyrrolo[2,3-d]pyrimidine-5-carbonyl)-pyridin-3-yl]-3-(2-chloro-phenyl)-urea;
1-[5-(4-Amino-7-isopropyl-7H-pyrrolo[2,3-d]pyrimidine-5-carbonyl)-pyridin-3-yl]-3-(3,4-difluoro-phenyl)-urea;
1-[5-(4-Amino-7-isopropyl-7H-pyrrolo[2,3-d]pyrimidine-5-carbonyl)-pyridin-3-yl]-3-m-tolyl-urea;
(4-Amino-7-isopropyl-7H-pyrrolo[2,3-d]pyrimidin-5-yl)-[5-(benzhydrylidene-amino)-pyridin-3-yl]-methanone;
1-[5-(4-Amino-7-methyl-7H-pyrrolo[2,3-d]pyrimidine-5-carbonyl)-pyridin-3-yl]-3-isopropyl-urea;
1-[5-(4-Amino-7-methyl-7H-pyrrolo[2,3-d]pyrimidine-5-carbonyl)-pyridin-3-yl]-3-propyl-urea;
1-[5-(4-Amino-7-methyl-7H-pyrrolo[2,3-d]pyrimidine-5-carbonyl)-pyridin-3-yl]-3-(2,4-difluoro-phenyl)-urea;
1-[5-(4-Amino-7-methyl-7H-pyrrolo[2,3-d]pyrimidine-5-carbonyl)-pyridin-3-yl]-3-phenyl-urea;
1-[5-(4-Amino-7-methyl-7H-pyrrolo[2,3-d]pyrimidine-5-carbonyl)-pyridin-3-yl]-3-(2-methoxy-5-methyl-phenyl)-urea;
1-[5-(4-Amino-7-methyl-7H-pyrrolo[2,3-d]pyrimidine-5-carbonyl)-pyridin-3-yl]-3-cyclohexyl-urea;
1-[5-(4-Amino-7-isopropyl-7H-pyrrolo[2,3-d]pyrimidine-5-carbonyl)-pyridin-3-yl]-3-(4-chloro-2-methyl-phenyl)-urea;
1-[5-(4-Amino-7-methyl-7H-pyrrolo[2,3-d]pyrimidine-5-carbonyl)-pyridin-3-yl]-3-(3-chloro-4-methyl-phenyl)-urea;
1-[5-(4-Amino-7-isopropyl-7H-pyrrolo[2,3-d]pyrimidine-5-carbonyl)-pyridin-3-yl]-3-(4-fluoro-phenyl)-urea;
1-[5-(4-Amino-7-methyl-7H-pyrrolo[2,3-d]pyrimidine-5-carbonyl)-pyridin-3-yl]-3-(4-chloro-2-methyl-phenyl)-urea;
1-[5-(4-Amino-7-methyl-7H-pyrrolo[2,3-d]pyrimidine-5-carbonyl)-pyridin-3-yl]-3-(2,4-dimethoxy-phenyl)-urea;
1-[5-(4-Amino-7-isopropyl-7H-pyrrolo[2,3-d]pyrimidine-5-carbonyl)-pyridin-3-yl]-3-(2,4-difluoro-phenyl)-urea;
1-[5-(4-Amino-7-methyl-7H-pyrrolo[2,3-d]pyrimidine-5-carbonyl)-pyridin-3-yl]-3-(3-trifluoromethyl-phenyl)-urea;
1-[5-(4-Amino-7-methyl-7H-pyrrolo[2,3-d]pyrimidine-5-carbonyl)-pyridin-3-yl]-3-(2,3-dichloro-phenyl)-urea;
1-[5-(4-Amino-7-isopropyl-7H-pyrrolo[2,3-d]pyrimidine-5-carbonyl)-pyridin-3-yl]-3-(2,6-difluoro-phenyl)-urea;
1-[5-(4-Amino-7-methyl-7H-pyrrolo[2,3-d]pyrimidine-5-carbonyl)-pyridin-3-yl]-3-(2,4-dichloro-phenyl)-urea;
N-[5-(4-Amino-7-isopropyl-7H-pyrrolo[2,3-d]pyrimidine-5-carbonyl)-pyridin-3-yl]-4-fluoro-benzenesulfonamide;
1-[5-(4-Amino-7-isopropyl-7H-pyrrolo[2,3-d]pyrimidine-5-carbonyl)-pyridin-3-yl]-3-(3,5-difluoro-phenyl)-urea;
1-[5-(4-Amino-7-isopropyl-7H-pyrrolo[2,3-d]pyrimidine-5-carbonyl)-pyridin-3-yl]-3-(4-methoxy-phenyl)-urea;
1-[5-(4-Amino-7-isopropyl-7H-pyrrolo[2,3-d]pyrimidine-5-carbonyl)-pyridin-3-yl]-3-(2,4-dichloro-phenyl)-urea;
1-[5-(4-Amino-7-isopropyl-7H-pyrrolo[2,3-d]pyrimidine-5-carbonyl)-pyridin-3-yl]-3-p-tolyl-urea;
1-[5-(4-Amino-7-methyl-7H-pyrrolo[2,3-d]pyrimidine-5-carbonyl)-pyridin-3-yl]-3-p-tolyl-urea;
1-[5-(4-Amino-7-methyl-7H-pyrrolo[2,3-d]pyrimidine-5-carbonyl)-pyridin-3-yl]-3-o-tolyl-urea;
1-[5-(4-Amino-7-methyl-7H-pyrrolo[2,3-d]pyrimidine-5-carbonyl)-pyridin-3-yl]-3-m-tolyl-urea;
1-[5-(4-Amino-7-methyl-7H-pyrrolo[2,3-d]pyrimidine-5-carbonyl)-pyridin-3-yl]-3-benzyl-urea;
1-[5-(4-Amino-7-methyl-7H-pyrrolo[2,3-d]pyrimidine-5-carbonyl)-pyridin-3-yl]-3-(2-fluoro-phenyl)-urea;
1-[5-(4-Amino-7-methyl-7H-pyrrolo[2,3-d]pyrimidine-5-carbonyl)-pyridin-3-yl]-3-(3-fluoro-phenyl)-urea;
1-[5-(4-Amino-7-methyl-7H-pyrrolo[2,3-d]pyrimidine-5-carbonyl)-pyridin-3-yl]-3-(4-fluoro-phenyl)-urea;
1-[5-(4-Amino-7-methyl-7H-pyrrolo[2,3-d]pyrimidine-5-carbonyl)-pyridin-3-yl]-3-(3-cyano-phenyl)-urea;
1-[5-(4-Amino-7-methyl-7H-pyrrolo[2,3-d]pyrimidine-5-carbonyl)-pyridin-3-yl]-3-(4-cyano-phenyl)-urea;
1-[5-(4-Amino-7-isopropyl-7H-pyrrolo[2,3-d]pyrimidine-5-carbonyl)-pyridin-3-yl]-3-(3-chloro-4-methyl-phenyl)-urea;
1-[5-(4-Amino-7-methyl-7H-pyrrolo[2,3-d]pyrimidine-5-carbonyl)-pyridin-3-yl]-3-benzoyl-urea;
N-[5-(4-Amino-7-methyl-7H-pyrrolo[2,3-d]pyrimidine-5-carbonyl)-pyridin-3-yl]-4-methyl-benzenesulfonamide;
N-[5-(4-Amino-7-isopropyl-7H-pyrrolo[2,3-d]pyrimidine-5-carbonyl)-pyridin-3-yl]-2-chloro-benzenesulfonamide;
N-[5-(4-Amino-7-methyl-7H-pyrrolo[2,3-d]pyrimidine-5-carbonyl)-pyridin-3-yl]-2-methyl-benzenesulfonamide;
N-[5-(4-Amino-7-methyl-7H-pyrrolo[2,3-d]pyrimidine-5-carbonyl)-pyridin-3-yl]-3-methyl-benzenesulfonamide;
N-[5-(4-Amino-7-methyl-7H-pyrrolo[2,3-d]pyrimidine-5-carbonyl)-pyridin-3-yl]-4-fluoro-benzenesulfonamide;
(4-Amino-7-isopropyl-7H-pyrrolo[2,3-d]pyrimidin-5-yl)-(5-amino-pyridin-3-yl)-methanone;

N-[5-(4-Amino-7-isopropyl-7H-pyrrolo[2,3-d]pyrimidine-5-carbonyl)-pyridin-3-yl]-2-fluoro-benzenesulfonamide;

N-[5-(4-Amino-7-isopropyl-7H-pyrrolo[2,3-d]pyrimidine-5-carbonyl)-pyridin-3-yl]-3-fluoro-benzenesulfonamide;

3,5-Dimethyl-isoxazole-4-sulfonic acid [5-(4-amino-7-isopropyl-7H-pyrrolo[2,3-d]pyrimidine-5-carbonyl)-pyridin-3-yl]-amide;

N-[5-(4-Amino-7-isopropyl-7H-pyrrolo[2,3-d]pyrimidine-5-carbonyl)-pyridin-3-yl]-4-chloro-benzenesulfonamide;

N-[5-(4-Amino-7-isopropyl-7H-pyrrolo[2,3-d]pyrimidine-5-carbonyl)-pyridin-3-yl]-3-chloro-benzenesulfonamide;

1-[5-(4-Amino-7-isopropyl-7 H-pyrrolo[2,3-d]pyrimidine-5-carbonyl)-pyridin-3-yl]-3-(3-fluoro-phenyl)-urea;

N-[5-(4-Amino-7-isopropyl-7H-pyrrolo[2,3-d]pyrimidine-5-carbonyl )-pyridin-3-yl]-2,4-difluoro-benzenesulfonamide;

N-[5-(4-Amino-7-isopropyl-7H-pyrrolo[2,3-d]pyrimidine-5-carbonyl)-pyridin-3-yl]-2,6-difluoro-benzenesulfonamide;

N-[5-(4-Amino-7-isopropyl-7H-pyrrolo[2,3-d]pyrimidine-5-carbonyl)-pyridin-3-yl]-3-chloro-4-methyl-benzenesulfonamide;

N-[5-(4-Amino-7-isopropyl-7H-pyrrolo[2,3-d]pyrimidine-5-carbonyl)-pyridin-3-yl]-3-chloro-4-fluoro-benzenesulfonamide;

1-[5-(4-Amino-7-methyl-7H-pyrrolo[2,3-d]pyrimidine-5-arbonyl)-pyridin-3-yl]-3-(3-methyl-benzyl)-urea;

1-[5-(4-Amino-7-methyl-7H-pyrrolo[2,3-d]pyrimidine-5-carbonyl)-pyridin-3-yl]-3-(4-methyl-benzyl)-urea;

1-[5-(4-Amino-7-methyl-7H-pyrrolo[2,3-d]pyrimidine-5-carbonyl)-pyridin-3-yl]-3-(2-methyl-benzyl)-urea;

1-[5-(4-Amino-7-methyl-7H-pyrrolo[2,3-d]pyrimidine-5-carbonyl)-pyridin-3-yl]-3-(2,6-dimethyl-phenyl)-urea;

1-[5-(4-Amino-7-isopropyl-7H-pyrrolo[2,3-d]pyrimidine-5-carbonyl)-pyridin-3-yl]-3-(3-trifluoromethyl-phenyl)-urea;

1-[5-(4-Amino-7-methyl-7H-pyrrolo[2,3-d]pyrimidine-5-carbonyl)-pyridin-3-yl]-3-(4-ethyl-phenyl)-urea;

N-[5-(4-Amino-7-methyl-7H-pyrrolo[2,3-d]pyrimidine-5-carbonyl)-pyridin-3-yl]-2-fluoro-benzenesulfonamide;

1-[5-(4-Amino-7-methyl-7H-pyrrolo[2,3-d]pyrimidine-5-carbonyl)-pyridin-3-yl]-3-(3,5-dimethyl-phenyl)-urea;

1-[5-(4-Amino-7-methyl-7H-pyrrolo[2,3-d]pyrimidine-5-carbonyl)-pyridin-3-yl]-3-(3,4-dimethyl-phenyl)-urea;

N-[5-(4-Amino-7-methyl-7H-pyrrolo[2,3-d]pyrimidine-5-carbonyl )-pyridin-3-yl]-3-fluoro-benzenesulfonamide;

1-[5-(4-Amino-7-methyl-7H-pyrrolo[2,3-d]pyrimidine-5-carbonyl)-pyridin-3-yl]-3-(2,5-dimethyl-phenyl)-urea;

3,5-Dimethyl-isoxazole-4-sulfonic acid [5-(4-amino-7-methyl-7H-pyrrolo[2,3-d]pyrimidine-5-carbonyl)-pyridin-3-yl]-amide;

1-[5-(4-Amino-7-methyl-7H-pyrrolo[2,3-d]pyrimidine-5-carbonyl)-pyridin-3-yl]-3-(2,3-dimethyl-phenyl)-urea;

N-[5-(4-Amino-7-methyl-7H-pyrrolo[2,3-d]pyrimidine-5-carbonyl )-pyridin-3-yl]-4-chloro-benzenesulfonamide;

1-[5-(4-Amino-7-methyl-7H-pyrrolo[2,3-d]pyrimidine-5-carbonyl)-pyridin-3-yl]-3-(2-ethyl-phenyl)-urea;

N-[5-(4-Amino-7-methyl-7H-pyrrolo[2,3-d]pyrimidine-5-carbonyl)-pyridin-3-yl]-2-chloro-benzenesulfonamide;

N-[5-(4-Amino-7-methyl-7H-pyrrolo[2,3-d]pyrimidine-5-carbonyl)-pyridin-3-yl]-3-chloro-benzenesulfonamide;

1-[5-(4-Amino-7-isopropyl-7H-pyrrolo[2,3-d]pyrimidine-5-carbonyl)-pyridin-3-yl]-3-(4-chloro-phenyl)-urea;

N-[5-(4-Amino-7-methyl-7H-pyrrolo[2,3-d]pyrimidine-5-carbonyl )-pyridin-3-yl]-3,5-difluoro-benzenesulfonamide;

N-[5-(4-Amino-7-methyl-7H-pyrrolo[2,3-d]pyrimidine-5-carbonyl )-pyridin-3-yl]-2,6-difluoro-benzenesulfonamide;

N-[5-(4-Amino-7-methyl-7H-pyrrolo[2,3-d]pyrimidine-5-carbonyl )-pyridin-3-yl]-2,4-difluoro-benzenesulfonamide;

1-[5-(4-Amino-7-isopropyl-7H-pyrrolo[2,3-d]pyrimidine-5-carbonyl)-pyridin-3-yl]-3-(3,5-dimethyl-phenyl)-urea;

1-[4-(4-Amino-7-isopropyl-7H-pyrrolo[2,3-d]pyrimidine-5-carbonyl)-pyridin-2-yl]-3-(4-chloro-2-methyl-phenyl)-urea;

N-[4-(4-Amino-7-isopropyl-7H-pyrrolo[2,3-d]pyrimidine-5-carbonyl)-pyridin-2-yl]-4-chloro-benzenesulfonamide;

1-[4-(4-Amino-7-isopropyl-7H-pyrrolo[2,3-d]pyrimidine-5-carbonyl)-6-methyl-pyridin-2-yl]-3-(3-fluoro-phenyl)-urea;

1-[4-(4-Amino-7-isopropyl-7H-pyrrolo[2,3-d]pyrimidine-5-carbonyl)-6-methyl-pyridin-2-yl]-3-(4-fluoro-phenyl)-urea;

(4-Amino-7-isopropyl-7H-pyrrolo[2,3-d]pyrimidin-5-yl)-(2-amino-pyridin-4-yl)-methanone;

1-[4-(4-Amino-7-isopropyl-7H-pyrrolo[2,3-d]pyrimidine-5-carbonyl)-pyridin-2-yl]-3-(2-fluoro-phenyl)-urea;

1-[4-(4-Amino-7-isopropyl-7H-pyrrolo[2,3-d]pyrimidine-5-carbonyl)-pyridin-2-yl]-3-(3-fluoro-phenyl)-urea;

1-[4-(4-Amino-7-isopropyl-7H-pyrrolo[2,3-d]pyrimidine-5-carbonyl)-pyridin-2-yl]-3-(4-fluoro-phenyl)-urea;

1-[4-(4-Amino-7-isopropyl-7H-pyrrolo[2,3-d]pyrimidine-5-carbonyl)-pyridin-2-yl]-3-(2-chloro-phenyl)-urea;

1-[4-(4-Amino-7-isopropyl-7H-pyrrolo[2,3-d]pyrimidine-5-carbonyl)-pyridin-2-yl]-3-(3-chloro-phenyl)-urea;

N-[4-(4-Amino-7-isopropyl-7H-pyrrolo[2,3-d]pyrimidine-5-carbonyl)-pyridin-2-yl]-2-fluoro-benzenesulfonamide;

1-[4-(4-Amino-7-isopropyl-7 H-pyrrolo[2,3-d]pyrimidine-5-carbonyl)-pyridin-2-yl]-3-(4-chloro-phenyl)-urea;

1-[4-(4-Amino-7-isopropyl-7 H-pyrrolo[2,3-d]pyrimidine-5-carbonyl)-6-methyl-pyridin-2-yl]-3-(2-fluoro-phenyl)-urea;

1-[4-(4-Amino-7-isopropyl-7H-pyrrolo[2,3-d]pyrimidine-5-carbonyl)-pyridin-2-yl]-3-m-tolyl-urea;

1-[4-(4-Amino-7-isopropyl-7H-pyrrolo[2,3-d]pyrimidine-5-arbonyl)-pyridin-2-yl]-3-(2-trifluoromethyl-phenyl)-urea;

N-[4-(4-Amino-7-isopropyl-7H-pyrrolo[2,3-d]pyrimidine-5-arbonyl)-pyridin-2-yl]-4-fluoro-benzenesulfonamide;

(4-Amino-7-isopropyl-7H-pyrrolo[2,3-d]pyrimidin-5-yl)-(2-amino-6-methyl-pyridin-4-yl)-methanone;

1-[4-(4-Amino-7-isopropyl-7H-pyrrolo[2,3-d]pyrimidine-5-arbonyl)-pyridin-2-yl]-3-(2,4-dichloro-phenyl)-urea;

1-[4-(4-Amino-7-isopropyl-7H-pyrrolo[2,3-d]pyrimidine-5-carbonyl)-pyridin-2-yl]-3-(2,4-difluoro-phenyl)-urea;

1-[4-(4-Amino-7-isopropyl-7H-pyrrolo[2,3-d]pyrimidine-5-carbonyl)-pyridin-2-yl]-3-(2-fluoro-5-methyl-phenyl)-urea;

1-[4-(4-Amino-7-isopropyl-7H-pyrrolo[2,3-d]pyrimidine-5-carbonyl)-pyridin-2-yl]-3-(3,5-difluoro-phenyl)-urea;

(4-Amino-7-isopropyl-7H-pyrrolo[2,3-d]pyrimidin-5-yl)-(6-amino-pyridin-2-yl)-methanone;

1-[6-(4-Amino-7-isopropyl-7 H-pyrrolo[2,3-d]pyrimidine-5-carbonyl)-pyridin-2-yl]-3-(3-fluoro-phenyl)-urea;

1-[6-(4-Amino-7-isopropyl-7H-pyrrolo[2,3-d]pyrimidine-5-carbonyl )-pyridin-2-yl]-3-(4-fluoro-phenyl)-urea;

1-[6-(4-Amino-7-isopropyl-7H-pyrrolo[2,3-d]pyrimidine-5-carbonyl )-pyridin-2-yl]-3-(2-chloro-phenyl)-urea;

1-[6-(4-Amino-7-isopropyl-7H-pyrrolo[2,3-d]pyrimidine-5-carbonyl)-pyridin-2-yl]-3-(3-chloro-phenyl)-urea;

1-[6-(4-Amino-7-isopropyl-7H-pyrrolo[2, 3-d]pyrimidine-5-carbonyl)-pyridin-2-yl]-3-(4-chloro-phenyl)-urea;

1-[6-(4-Amino-7-isopropyl-7 H-pyrrolo[2,3-d]pyrimidine-5-carbonyl)-pyridin-2-yl]-3-(2,4-dichloro-phenyl)-urea;

1-[6-(4-Amino-7-isopropyl-7 H-pyrrolo[2,3-d]pyrimidine-5-carbonyl)-pyridin-2-yl]-3-(2,4-difluoro-phenyl)-urea;

1-[6-(4-Amino-7-isopropyl-7H-pyrrolo[2,3-d]pyrimidine-5-carbonyl)-pyridin-2-yl]-3-m-tolyl-urea;

1-[6-(4-Amino-7-isopropyl-7H-pyrrolo[2,3-d]pyrimidine-5-carbonyl)-pyridin-2-yl]-3-(3-trifluoromethyl-phenyl)-urea;

N-[6-(4-Amino-7-isopropyl-7H-pyrrolo[2,3-d]pyrimidine-5-carbonyl )-pyridin-2-yl]-2-fluoro-benzenesulfonamide;

N-[6-(4-Amino-7-isopropyl-7H-pyrrolo[2,3-d]pyrimidine-5-carbonyl)-pyridin-2-yl]4-fluoro-benzenesulfonamide;

N-[6-(4-Amino-7-isopropyl-7H-pyrrolo[2,3-d]pyrimidine-5-carbonyl )-pyridin-2-yl]-4-chloro-benzenesulfonamide;

1-[6-(4-Amino-7-isopropyl-7 H-pyrrolo[2,3-d]pyrimidine-5-carbonyl)-pyridin-2-yl]-3-(2-fluoro-phenyl)-urea;

1-[2-(4-Amino-7-isopropyl-7H-pyrrolo[2,3-d]pyrimidine-5-carbonyl)-pyridin-4-yl]-3-(2,4-difluoro-phenyl)-urea;

1-[2-(4-Amino-7-isopropyl-7 H-pyrrolo[2,3-d]pyrimidine-5-carbonyl)-pyridin-4-yl]-3-(2,4-dichloro-phenyl)-urea;

1-[2-(4-Amino-7-isopropyl-7H-pyrrolo[2,3-d]pyrimidine-5-carbonyl)-pyridin-4-yl]-3-(2-fluoro-5-methyl-phenyl)-urea;

1-[2-(4-Amino-7-isopropyl-7 H-pyrrolo[2,3-d]pyrimidine-5-carbonyl)-pyridin-4-yl]-3-(3,5-difluoro-phenyl)-urea;

1-[2-(4-Amino-7-isopropyl-7H-pyrrolo[2,3-d]pyrimidine-5-carbonyl)-pyridin-4-yl]-3-(4-chloro-2-methyl-phenyl)-urea;

N-[2-(4-Amino-7-isopropyl-7H-pyrrolo[2,3-d]pyrimidine-5-carbonyl )-pyridin-4-yl]-2-fluoro-benzenesulfonamide;

N-[2-(4-Amino-7-isopropyl-7H-pyrrolo[2,3-d]pyrimidine-5-carbonyl)-pyridin-4-yl]-4-fluoro-benzenesulfonamide;

N-[2-(4-Amino-7-isopropyl-7H-pyrrolo[2,3-d]pyrimidine-5-carbonyl )-pyridin-4-yl]-4-chloro-benzenesulfonamide;

(4-Amino-7-isopropyl-7H-pyrrolo[2,3-d]pyrimidin-5-yl)-(4-amino-pyridin-2-yl)-methanone;

1-[2-(4-Amino-7-isopropyl-7 H-pyrrolo[2,3-d]pyrimidine-5-carbonyl)-pyridin-4-yl]-3-(2-fluoro-phenyl)-urea;

1-[2-(4-Amino-7-isopropyl-7H-pyrrolo[2,3-d]pyrimidine-5-carbonyl)-pyridin-4-yl]-3-(3-fluoro-phenyl)-urea;

1-[2-(4-Amino-7-isopropyl-7 H-pyrrolo[2,3-d]pyrimidine-5-carbonyl)-pyridin-4-yl]-3-(4-fluoro-phenyl)-urea;

1-[2-(4-Amino-7-isopropyl-7H-pyrrolo[2,3-d]pyrimidine-5-carbonyl)-pyridin-4-yl]-3-(2-chloro-phenyl)-urea;

1-[2-(4-Amino-7-isopropyl-7H-pyrrolo[2,3-d]pyrimidine-5-carbonyl)-pyridin-4-yl]-3-(3-chloro-phenyl)-urea;

1-[2-(4-Amino-7-isopropyl-7H-pyrrolo[2,3-d]pyrimidine-5-carbonyl)-pyridin-4-yl]-3-(4-chloro-phenyl)-urea;

1-[2-(4-Amino-7-isopropyl-7H-pyrrolo[2,3-d]pyrimidine-5-carbonyl)-pyridin-4-yl]-3-m-tolyl-urea;

1-[2-(4-Amino-7-isopropyl-7H-pyrrolo[2,3-d]pyrimidine-5-carbonyl)-pyridin-4-yl]-3-(3-trifluoromethyl-phenyl)-urea;

and the pharmaceutically acceptable salts, prodrugs, hydrates and solvates of the aforementioned compounds.

Specific more preferred compound of formula 1 are selected from the group consisting of:

1-[5-(4-Amino-7-isopropyl-7H-pyrrolo[2,3-d]pyrimidine-5-carbonyl)-pyridin-3-yl]-3-(2-fluoro-5-methyl-phenyl)-urea;

1-[5-(4-Amino-7-isopropyl-7H-pyrrolo[2,3-d]pyrimidine-5-carbonyl)-pyridin-3-yl]-3-(4-chloro-phenyl)-urea;

1-[5-(4-Amino-7-isopropyl-7H-pyrrolo[2,3-d]pyrimidine-5-carbonyl)-pyridin-3-yl]-3-(2,4-dichloro-phenyl)-urea;

1-[5-(4-Amino-7-isopropyl-7H-pyrrolo[2,3-d]pyrimidine-5-carbonyl)-pyridin-3-yl]-3-p-tolyl-urea;

1-[5-(4-Amino-7-isopropyl-7H-pyrrolo[2,3-d]pyrimidine-5-carbonyl)-pyridin-3-yl]-3-m-tolyl-urea;

1-[5-(4-Amino-7-isopropyl-7 H-pyrrolo[2,3-d]pyrimidine-5-carbonyl)-pyridin-3-yl]-3-(2-fluoro-phenyl)-urea;

1-[5-(4-Amino-7-isopropyl-7H-pyrrolo[2,3-d]pyrimidine-5-carbonyl)-pyridin-3-yl]-3-(3-fluoro-phenyl)-urea;

1-[5-(4-Amino-7-isopropyl-7H-pyrrolo[2,3-d]pyrimidine-5-carbonyl)-pyridin-3-yl]-3-(4-fluoro-phenyl)-urea;

1-[5-(4-Amino-7-isopropyl-7H-pyrrolo[2,3-d]pyrimidine-5-carbonyl)-pyridin-3-yl]-3-(3,5-dimethyl-phenyl)-urea;

1-[5-(4-Amino-7-isopropyl-7H-pyrrolo[2,3-d]pyrimidine-5-carbonyl)-pyridin-3-yl]-3-(4-methoxy-phenyl)-urea;
1-[5-(4-Amino-7-isopropyl-7H-pyrrolo[2,3-d]pyrimidine-5-carbonyl)-pyridin-3-yl]-3-(2-chloro-phenyl)-urea;
1-[5-(4-Amino-7-isopropyl-7 H-pyrrolo[2,3-d]pyrimidine-5-carbonyl)-pyridin-3-yl]-3-(3-chloro-phenyl)-urea;
1-[5-(4-Amino-7-isopropyl-7H-pyrrolo[2,3-d]pyrimidine-5-carbonyl)-pyridin-3-yl]-3-(3,5-difluoro-phenyl)-urea;
1-[5-(4-Amino-7-isopropyl-7H-pyrrolo[2,3-d]pyrimidine-5-carbonyl)-pyridin-3-yl]-3-(3,4-difluoro-phenyl)-urea;
1-[5-(4-Amino-7-isopropyl-7H-pyrrolo[2,3-d]pyrimidine-5-carbonyl)-pyridin-3-yl]-3-(2,6-difluoro-phenyl)-urea;
1-[5-(4-Amino-7-isopropyl-7H-pyrrolo[2,3-d]pyrimidine-5-carbonyl)-pyridin-3-yl]-3-(2,4-difluoro-phenyl)-urea;
1-[5-(4-Amino-7-isopropyl-7H-pyrrolo[2,3-d]pyrimidine-5-carbonyl)-pyridin-3-yl]-3-(2-methoxy-5-methyl-phenyl)-urea;
1-[5-(4-Amino-7-isopropyl-7H-pyrrolo[2,3-d]pyrimidine-5-carbonyl)-pyridin-3-yl]-3-(3-chloro-4-methyl-phenyl)-urea;
1-[5-(4-Amino-7-isopropyl-7 H-pyrrolo[2,3-d]pyrimidine-5-carbonyl)-pyridin-3-yl]-3-(4-chloro-2-methyl-phenyl)-urea;
1-[5-(4-Amino-7-isopropyl-7H-pyrrolo[2,3-d]pyrimidine-5-carbonyl )-pyridin-3-yl]-3-(3,5-dimethoxy-phenyl)-urea;
1-[5-(4-Amino-7-isopropyl-7H-pyrrolo[2,3-d]pyrimidine-5-carbonyl)-pyridin-3-yl]-3-(3-trifluoromethyl-phenyl)-urea;
1-[5-(4-Amino-7-isopropyl-7H-pyrrolo[2,3-d]pyrimidine-5-carbonyl)-pyridin-3-yl]-3-(2,3-dichloro-phenyl)-urea;
1-[5-(4-Amino-7-methyl-7H-pyrrolo[2,3-d]pyrimidine-5-carbonyl)-pyridin-3-yl]-3-phenyl-urea;
1-[5-(4-Amino-7-methyl-7H-pyrrolo[2,3-d]pyrimidine-5-carbonyl)-pyridin-3-yl]-3-p-tolyl-urea;
1-[5-(4-Amino-7-methyl-7H-pyrrolo[2,3-d]pyrimidine-5-carbonyl)-pyridin-3-yl]-3-o-tolyl-urea;
1-[5-(4-Amino-7-methyl-7H-pyrrolo[2,3-d]pyrimidine-5-carbonyl )-pyridin-3-yl]-3-m-tolyl-urea;
1-[5-(4-Amino-7-methyl-7H-pyrrolo[2,3-d]pyrimidine-5-carbonyl)-pyridin-3-yl]-3-(2-fluoro-phenyl)-urea;
1-[5-(4-Amino-7-methyl-7H-pyrrolo[2,3-d]pyrimidine-5-carbonyl)-pyridin-3-yl]-3-(3-fluoro-phenyl)-urea;
1-[5-(4-Amino-7-methyl-7H-pyrrolo[2,3-d]pyrimidine-5-carbonyl )-pyridin-3-yl]-3-(4-fluoro-phenyl)-urea;
1-[5-(4-Amino-7-methyl-7H-pyrrolo[2,3-d]pyrimidine-5-carbonyl)-pyridin-3-yl]-3-(3-cyano-phenyl)-urea;
1-[5-(4-Amino-7-methyl-7H-pyrrolo[2,3-d]pyrimidine-5-carbonyl)-pyridin-3-yl]-3-(4-cyano-phenyl)-urea;
1-[5-(4-Amino-7-methyl-7H-pyrrolo[2,3-d]pyrimidine-5-carbonyl)-pyridin-3-yl]-3-(2,6-dimethyl-phenyl)-urea;
1-[5-(4-Amino-7-methyl-7H-pyrrolo[2,3-d]pyrimidine-5-carbonyl)-pyridin-3-yl]-3-(4-ethyl-phenyl)-urea;
1-[5-(4-Amino-7-methyl-7H-pyrrolo[2,3-d]pyrimidine-5-carbonyl)-pyridin-3-yl]-3-(3,5-dimethyl-phenyl)-urea;
1-[5-(4-Amino-7-methyl-7H-pyrrolo[2,3-d]pyrimidine-5-carbonyl)-pyridin-3-yl]-3-(3,4-dimethyl-phenyl)-urea;
1-[5-(4-Amino-7-methyl-7H-pyrrolo[2,3-d]pyrimidine-5-carbonyl)-pyridin-3-yl]-3-(2,5-dimethyl-phenyl)-urea;
1-[5-(4-Amino-7-methyl-7H-pyrrolo[2,3-d]pyrimidine-5-carbonyl)-pyridin-3-yl]-3-(2,3-dimethyl-phenyl)-urea;
1-[5-(4-Amino-7-methyl-7H-pyrrolo[2,3-d]pyrimidine-5-carbonyl)-pyridin-3-yl]-3-(2-ethyl-phenyl)-urea;
1-[5-(4-Amino-7-methyl-7H-pyrrolo[2,3-d]pyrimidine-5-carbonyl)-pyridin-3-yl]-3-(2,4-dimethyl-phenyl)-urea;
1-[5-(4-Amino-7-methyl-7H-pyrrolo[2,3-d]pyrimidine-5-carbonyl)-pyridin-3-yl]-3-(4-methoxy-phenyl)-urea;
1-[5-(4-Amino-7-methyl-7H-pyrrolo[2,3-d]pyrimidine-5-carbonyl)-pyridin-3-yl]-3-(2-fluoro-5-methyl-phenyl)-urea;
1-[5-(4-Amino-7-methyl-7H-pyrrolo[2,3-d]pyrimidine-5-carbonyl)-pyridin-3-yl]-3-(2-chloro-phenyl)-urea;
1-[5-(4-Amino-7-methyl-7H-pyrrolo[2,3-d]pyrimidine-5-carbonyl)-pyridin-3-yl]-3-(3-chloro-phenyl)-urea;
1-[5-(4-Amino-7-methyl-7H-pyrrolo[2,3-d]pyrimidine-5-carbonyl )-pyridin-3-yl]-3-(4-chloro-phenyl)-urea;
1-[5-(4-Amino-7-methyl-7H-pyrrolo[2,3-d]pyrimidine-5-carbonyl)-pyridin-3-yl]-3-(3,5-difluoro-phenyl)-urea;
1-[5-(4-Amino-7-methyl-7H-pyrrolo[2,3-d]pyrimidine-5-carbonyl)-pyridin-3-yl]-3-(3,4-difluoro-phenyl)-urea;
1-[5-(4-Amino-7-methyl-7H-pyrrolo[2,3-d]pyrimidine-5-carbonyl)-pyridin-3-yl]-3-(2,6-difluoro-phenyl)-urea;
1-[5-(4-Amino-7-methyl-7H-pyrrolo[2,3-d]pyrimidine-5-carbonyl)-pyridin-3-yl]-3-(2,4-difluoro-phenyl)-urea;
1-[5-(4-Amino-7-methyl-7H-pyrrolo[2,3-d]pyrimidine-5-carbonyl)-pyridin-3-yl]-3-(2-methoxy-5-methyl-phenyl)-urea;
1-[5-(4-Amino-7-methyl-7H-pyrrolo[2,3-d]pyrimidine-5-carbonyl)-pyridin-3-yl]-3-(3-chloro-4-methyl-phenyl)-urea;
1-[5-(4-Amino-7-methyl-7H-pyrrolo[2,3-d]pyrimidine-5-carbonyl)-pyridin-3-yl]-3-(4-chloro-2-methyl-phenyl)-urea;
1-[5-(4-Amino-7-methyl-7H-pyrrolo[2,3-d]pyrimidine-5-carbonyl)-pyridin-3-yl]-3-(2,4-dimethoxy-phenyl)-urea;
1-[5-(4-Amino-7-methyl-7H-pyrrolo[2,3-d]pyrimidine-5-carbonyl)-pyridin-3-yl]-3-(3-trifluoromethyl-phenyl)-urea;
1-[5-(4-Amino-7-methyl-7H-pyrrolo[2,3-d]pyrimidine-5-carbonyl)-pyridin-3-yl]-3-(2,3-dichloro-phenyl)-urea;
1-[5-(4-Amino-7-methyl-7H-pyrrolo[2,3-d]pyrimidine-5-carbonyl)-pyridin-3-yl]-3-(2,4-dichloro-phenyl)-urea;
1-[5-(4-Amino-7-methyl-7H-pyrrolo[2,3-d]pyrimidine-5-carbonyl)-pyridin-3-yl]-3-phenyl-urea;
1-[5-(4-Amino-7-methyl-7H-pyrrolo[2,3-d]pyrimidine-5-carbonyl)-pyridin-3-yl]-3-p-tolyl-urea;
1-[5-(4-Amino-7-methyl-7H-pyrrolo[2,3-d]pyrimidine-5-carbonyl)-pyridin-3-yl]-3-m-tolyl-urea;
1-[5-(4-Amino-7-methyl-7H-pyrrolo[2,3-d]pyrimidine-5-carbonyl)-pyridin-3-yl]-3-(4-cyano-phenyl)-urea;
1-[5-(4-Amino-7-methyl-7H-pyrrolo[2,3-d]pyrimidine-5-carbonyl)-pyridin-3-yl]-3-(3-fluoro-phenyl)-urea;
1-[5-(4-Amino-7-methyl-7H-pyrrolo[2,3-d]pyrimidine-5-carbonyl)-pyridin-3-yl]-3-o-tolyl-urea;
1-[5-(4-Amino-7-methyl-7H-pyrrolo[2,3-d]pyrimidine-5-carbonyl)-pyridin-3-yl]-3-(4-fluoro-phenyl)-urea;
1-[5-(4-Amino-7-methyl-7H-pyrrolo[2,3-d]pyrimidine-5-carbonyl)-pyridin-3-yl]-3-(2-fluoro-phenyl)-urea;
1-[5-(4-Amino-7-methyl-7H-pyrrolo[2,3-d]pyrimidine-5-carbonyl)-pyridin-3-yl]-3-(3-cyano-phenyl)-urea;
1-[5-(4-Amino-7-methyl-7H-pyrrolo[2,3-d]pyrimidine-5-carbonyl)-pyridin-3-yl]-3-(4-methoxy-phenyl)-urea;
1-[5-(4-Amino-7-methyl-7H-pyrrolo[2,3-d]pyrimidine-5-carbonyl)-pyridin-3-yl]-3-(3,5-dimethyl-phenyl)-urea;

1-[5-(4-Amino-7-methyl-7H-pyrrolo[2,3-d]pyrimidine-5-carbonyl)-pyridin-3-yl]-3-(2,6-dimethyl-phenyl)-urea;
1-[5-(4-Amino-7-methyl-7H-pyrrolo[2,3-d]pyrimidine-5-carbonyl)-pyridin-3-yl]-3-(2-fluoro-5-methyl-phenyl)-urea;
1-[5-(4-Amino-7-methyl-7H-pyrrolo[2,3-d]pyrimidine-5-carbonyl)-pyridin-3-yl]-3-(2,3-dimethyl-phenyl)-urea;
1-[5-(4-Amino-7-methyl-7H-pyrrolo[2,3-d]pyrimidine-5-carbonyl)-pyridin-3-yl]-3-(2-chloro-phenyl)-urea;
1-[5-(4-Amino-7-methyl-7H-pyrrolo[2,3-d]pyrimidine-5-carbonyl)-pyridin-3-yl]-3-(3,4-dimethyl-phenyl)-urea;
1-[5-(4-Amino-7-methyl-7H-pyrrolo[2,3-d]pyrimidine-5-carbonyl)-pyridin-3-yl]-3-(3,4-difluoro-phenyl)-urea;
1-[5-(4-Amino-7-methyl-7H-pyrrolo[2,3-d]pyrimidine-5-carbonyl)-pyridin-3-yl]-3-(4-ethyl-phenyl)-urea;
1-[5-(4-Amino-7-methyl-7H-pyrrolo[2,3-d]pyrimidine-5-carbonyl)-pyridin-3-yl]-3-(2,6-difluoro-phenyl)-urea;
1-[5-(4-Amino-7-methyl-7H-pyrrolo[2,3-d]pyrimidine-5-carbonyl)-pyridin-3-yl]-3-(2-ethyl-phenyl)-urea;
1-[5-(4-Amino-7-methyl-7H-pyrrolo[2,3-d]pyrimidine-5-carbonyl )-pyridin-3-yl]-3-(2,5-dimethyl-phenyl)-urea;
1-[5-(4-Amino-7-methyl-7H-pyrrolo[2,3-d]pyrimidine-5-carbonyl)-pyridin-3-yl]-3-(2,4-difluoro-phenyl)-urea;
1-[5-(4-Amino-7-methyl-7H-pyrrolo[2,3-d]pyrimidine-5-carbonyl )-pyridin-3-yl]-3-(3-chloro-phenyl)-urea;
1-[5-(4-Amino-7-methyl-7H-pyrrolo[2,3-d]pyrimidine-5-carbonyl)-pyridin-3-yl]-3-(2,4-dimethoxy-phenyl)-urea;
1-[5-(4-Amino-7-methyl-7H-pyrrolo[2,3-d]pyrimidine-5-carbonyl )-pyridin-3-yl]-3-(4-chloro-phenyl)-urea;
1-[5-(4-Amino-7-methyl-7H-pyrrolo[2,3-d]pyrimidine-5-carbonyl)-pyridin-3-yl]-3-(2,4-dimethyl-phenyl)-urea;
1-[5-(4-Amino-7-methyl-7H-pyrrolo[2,3-d]pyrimidine-5-carbonyl)-pyridin-3-yl]-3-(2-methoxy-5-methyl-phenyl)-urea;
1-[5-(4-Amino-7-methyl-7H-pyrrolo[2,3-d]pyrimidine-5-carbonyl)-pyridin-3-yl]-3-(3-trifluoromethyl-phenyl)-urea;
1-[5-(4-Amino-7-methyl-7H-pyrrolo[2,3-d]pyrimidine-5-carbonyl)-pyridin-3-yl]-3-(3,5-difluoro-phenyl)-urea;
1-[5-(4-Amino-7-methyl-7H-pyrrolo[2,3-d]pyrimidine-5-carbonyl)-pyridin-3-yl]-3-(2,4-dichloro-phenyl)-urea;
1-[5-(4-Amino-7-methyl-7H-pyrrolo[2,3-d]pyrimidine-5-carbonyl)-pyridin-3-yl]-3-(3-chloro-4-methyl-phenyl)-urea;
1-[5-(4-Amino-7-methyl-7H-pyrrolo[2,3-d]pyrimidine-5-carbonyl)-pyridin-3-yl]-3-(2,3-dichloro-phenyl)-urea;
1-[5-(4-Amino-7-methyl-7H-pyrrolo[2,3-d]pyrimidine-5-carbonyl)-pyridin-3-yl]-3-(4-chloro-2-methyl-phenyl)-urea;
and the pharmaceutically acceptable salts, prodrugs, hydrates and solvates of the aforementioned compounds.

Specific more preferred compounds of formula 1 are selected from the group consisting of:
1-[5-(4-Amino-7-isopropyl-7H-pyrrolo[2,3-d]pyrimidine-5-carbonyl)-pyridin-3-yl]-3-(2-fluoro-5-methyl-phenyl)-urea;
1-[5-(4-Amino-7-isopropyl-7H-pyrrolo[2,3-d]pyrimidine-5-carbonyl)-pyridin-3-yl]-3-(4-chloro-phenyl)-urea;
1-[5-(4-Amino-7-isopropyl-7H-pyrrolo[2,3-d]pyrimidine-5-carbonyl)-pyridin-3-yl]-3-(2,4-dichloro-phenyl)-urea;
1-[5-(4-Amino-7-isopropyl-7H-pyrrolo[2,3-d]pyrimidine-5-carbonyl)-pyridin-3-yl]-3-p-tolyl-urea;
1-[5-(4-Amino-7-isopropyl-7H-pyrrolo[2,3-d]pyrimidine-5-carbonyl)-pyridin-3-yl]-3-m-tolyl-urea;
1-[5-(4-Amino-7-isopropyl-7H-pyrrolo[2,3-d]pyrimidine-5-carbonyl)-pyridin-3-yl]-3-(2-fluoro-phenyl)-urea;
1-[5-(4-Amino-7-isopropyl-7H-pyrrolo[2,3-d]pyrimidine-5-carbonyl)-pyridin-3-yl]-3-(3-fluoro-phenyl)-urea;
1-[5-(4-Amino-7-isopropyl-7H-pyrrolo[2,3-d]pyrimidine-5-carbonyl)-pyridin-3-yl]-3-(4-fluoro-phenyl)-urea;
1-[5-(4-Amino-7-isopropyl-7H-pyrrolo[2,3-d]pyrimidine-5-carbonyl)-pyridin-3-yl]-3-(3,5-dimethyl-phenyl)-urea;
1-[5-(4-Amino-7-isopropyl-7H-pyrrolo[2,3-d]pyrimidine-5-carbonyl)-pyridin-3-yl]-3-(4-methoxy-phenyl)-urea;
1-[5-(4-Amino-7-isopropyl-7H-pyrrolo[2,3-d]pyrimidine-5-carbonyl)-pyridin-3-yl]-3-(2-chloro-phenyl)-urea;
1-[5-(4-Amino-7-isopropyl-7 H-pyrrolo[2,3-d]pyrimidine-5-carbonyl)-pyridin-3-yl]-3-(3-chloro-phenyl)-urea;
1-[5-(4-Amino-7-isopropyl-7 H-pyrrolo[2,3-d]pyrimidine-5-carbonyl)-pyridin-3-yl]-3-(3,5-difluoro-phenyl)-urea;
1-[5-(4-Amino-7-isopropyl-7H-pyrrolo[2,3-d]pyrimidine-5-carbonyl)-pyridin-3-yl]-3-(3,4-difluoro-phenyl)-urea;
1-[5-(4-Amino-7-isopropyl-7H-pyrrolo[2,3-d]pyrimidine-5-carbonyl)-pyridin-3-yl]-3-(2,6-difluoro-phenyl)-urea;
1-[5-(4-Amino-7-isopropyl-7H-pyrrolo[2,3-d]pyrimidine-5-carbonyl)-pyridin-3-yl]-3-(2,4-difluoro-phenyl)-urea;
1-[5-(4-Amino-7-isopropyl-7H-pyrrolo[2,3-d]pyrimidine-5-carbonyl)-pyridin-3-yl]-3-(2-methoxy-5-methyl-phenyl)-urea;
1-[5-(4-Amino-7-isopropyl-7H-pyrrolo[2,3-d]pyrimidine-5-carbonyl)-pyridin-3-yl]-3-(3-chloro-4-methyl-phenyl)-urea;
1-[5-(4-Amino-7-isopropyl-7H-pyrrolo[2,3-d]pyrimidine-5-carbonyl)-pyridin-3-yl]-3-(4-chloro-2-methyl-phenyl)-urea;
1-[5-(4-Amino-7-isopropyl-7 H-pyrrolo[2,3-d]pyrimidine-5-carbonyl)-pyridin-3-yl]-3-(3,5-dimethoxy-phenyl)-urea;
1-[5-(4-Amino-7-isopropyl-7H-pyrrolo[2,3-d]pyrimidine-5-carbonyl)-pyridin-3-yl]-3-(3-trifluoromethyl-phenyl)-urea;
1-[5-(4-Amino-7-isopropyl-7H-pyrrolo[2,3-d]pyrimidine-5-carbonyl)-pyridin-3-yl]-3-(2,3-dichloro-phenyl)-urea;
1-[5-(4-Amino-7-methyl-7H-pyrrolo[2,3-d]pyrimidine-5-carbonyl)-pyridin-3-yl]-3-phenyl-urea;
1-[5-(4-Amino-7-methyl-7H-pyrrolo[2,3-d]pyrimidine-5-carbonyl)-pyridin-3-yl]-3-p-tolyl-urea;
1-[5-(4-Amino-7-methyl-7H-pyrrolo[2,3-d]pyrimidine-5-carbonyl)-pyridin-3-yl]-3-o-toly-urea;
1-[5-(4-Amino-7-methyl-7H-pyrrolo[2,3-d]pyrimidine-5-carbonyl)-pyridin-3-yl]-3-m-tolyl-urea;
1-[5-(4-Amino-7-methyl-7H-pyrrolo[2,3-d]pyrimidine-5-carbonyl)-pyridin-3-yl]-3-(2-fluoro-phenyl)-urea;
1-[5-(4-Amino-7-methyl-7H-pyrrolo[2,3-d]pyrimidine-5-carbonyl )-pyridin-3-yl]-3-(3-fluoro-phenyl)-urea;
1-[5-(4-Amino-7-methyl-7H-pyrrolo[2,3-d]pyrimidine-5-carbonyl)-pyridin-3-yl]-3-(4-fluoro-phenyl)-urea;

1-[5-(4-Amino-7-methyl-7H-pyrrolo[2,3-d]pyrimidine-5-carbonyl)-pyridin-3-yl]-3-(3-cyano-phenyl)-urea;
1-[5-(4-Amino-7-methyl-7H-pyrrolo[2,3-d]pyrimidine-5-carbonyl )-pyridin-3-yl]-3-(4-cyano-phenyl)-urea;
1-[5-(4-Amino-7-methyl-7H-pyrrolo[2,3-d]pyrimidine-5-carbonyl)-pyridin-3-yl]-3-(2,6-dimethyl-phenyl)-urea;
1-[5-(4-Amino-7-methyl-7H-pyrrolo[2,3-d]pyrimidine-5-carbonyl)-pyridin-3-yl]-3-(4-ethyl-phenyl)-urea;
1-[5-(4-Amino-7-methyl-7H-pyrrolo[2,3-d]pyrimidine-5-carbonyl)-pyridin-3-yl]-3-(3,5-dimethyl-phenyl)-urea;
1-[5-(4-Amino-7-methyl-7H-pyrrolo[2,3-d]pyrimidine-5-carbonyl)-pyridin-3-yl]-3-(3,4-dimethyl-phenyl)-urea;
1-[5-(4-Amino-7-methyl-7H-pyrrolo[2,3-d]pyrimidine-5-carbonyl)-pyridin-3-yl]-3-(2,5-dimethyl-phenyl)-urea;
1-[5-(4-Amino-7-methyl-7H-pyrrolo[2,3-d]pyrimidine-5-carbonyl)-pyridin-3-yl]-3-(2,3-dimethyl-phenyl)-urea;
1-[5-(4-Amino-7-methyl-7H-pyrrolo[2,3-d]pyrimidine-5-carbonyl)-pyridin-3-yl]-3-(2-ethyl-phenyl)-urea;
1-[5-(4-Amino-7-methyl-7H-pyrrolo[2,3-d]pyrimidine-5-carbonyl)-pyridin-3-yl]-3-(2,4-dimethyl-phenyl)-urea;
1-[5-(4-Amino-7-methyl-7H-pyrrolo[2,3-d]pyrimidine-5-carbonyl)-pyridin-3-yl]-3-(4-methoxy-phenyl)-urea;
1-[5-(4-Amino-7-methyl-7H-pyrrolo[2,3-d]pyrimidine-5-carbonyl)-pyridin-3-yl]-3-(2-fluoro-5-methyl-phenyl)-urea;
1-[5-(4-Amino-7-methyl-7H-pyrrolo[2,3-d]pyrimidine-5-carbonyl)-pyridin-3-yl]-3-(2-chloro-phenyl)-urea;
1-[5-(4-Amino-7-methyl-7H-pyrrolo[2,3-d]pyrimidine-5-carbonyl)-pyridin-3-yl]-3-(3-chloro-phenyl)-urea;
1-[5-(4-Amino-7-methyl-7H-pyrrolo[2,3-d]pyrimidine-5-carbonyl)-pyridin-3-yl]-3-(4-chloro-phenyl)-urea;
1-[5-(4-Amino-7-methyl-7H-pyrrolo[2,3-d]pyrimidine-5-carbonyl)-pyridin-3-yl]-3-(3,5-difluoro-phenyl)-urea;
1-[5-(4-Amino-7-methyl-7H-pyrrolo[2,3-d]pyrimidine-5-carbonyl)-pyridin-3-yl]-3-(3,4-difluoro-phenyl)-urea;
1-[5-(4-Amino-7-methyl-7H-pyrrolo[2,3-d]pyrimidine-5-carbonyl)-pyridin-3-yl]-3-(2,6-difluoro-phenyl)-urea;
1-[5-(4-Amino-7-methyl-7H-pyrrolo[2,3-d]pyrimidine-5-carbonyl)-pyridin-3-yl]-3-(2,4-difluoro-phenyl)-urea;
1-[5-(4-Amino-7-methyl-7H-pyrrolo[2,3-d]pyrimidine-5-carbonyl)-pyridin-3-yl]-3-(2-methoxy-5-methyl-phenyl)-urea;
1-[5-(4-Amino-7-methyl-7H-pyrrolo[2,3-d]pyrimidine-5-carbonyl)-pyridin-3-yl]-3-(3-chloro-4-methyl-phenyl)-urea;
1-[5-(4-Amino-7-methyl-7H-pyrrolo[2,3-d]pyrimidine-5-carbonyl)-pyridin-3-yl]-3-(4-chloro-2-methyl-phenyl)-urea;
1-[5-(4-Amino-7-methyl-7H-pyrrolo[2,3-d]pyrimidine-5-carbonyl)-pyridin-3-yl]-3-(2,4-dimethoxy-phenyl)-urea;
1-[5-(4-Amino-7-methyl-7H-pyrrolo[2,3-d]pyrimidine-5-carbonyl)-pyridin-3-yl]-3-(3-trifluoromethyl-phenyl)-urea;
1-[5-(4-Amino-7-methyl-7H-pyrrolo[2,3-d]pyrimidine-5-carbonyl)-pyridin-3-yl]-3-(2,3-dichloro-phenyl)-urea;
1-[5-(4-Amino-7-methyl-7 H-pyrrolo[2,3-d]pyrimidine-5-carbonyl)-pyridin-3-yl]-3-(2,4-dichloro-phenyl)-urea;
1-[5-(4-Amino-7-methyl-7H-pyrrolo[2,3-d]pyrimidine-5-carbonyl)-pyridin-3-yl]-3-phenyl-urea;
1-[5-(4-Amino-7-methyl-7H-pyrrolo[2,3-d]pyrimidine-5-carbonyl)-pyridin-3-yl]-3-p-tolyl-urea;
1-[5-(4-Amino-7-methyl-7H-pyrrolo[2,3-d]pyrimidine-5-carbonyl)-pyridin-3-yl]-3-m-tolyl-urea;
1-[5-(4-Amino-7-methyl-7H-pyrrolo[2,3-d]pyrimidine-5-carbonyl)-pyridin-3-yl]-3-(4-cyano-phenyl)-urea;
1-[5-(4-Amino-7-methyl-7H-pyrrolo[2,3-d]pyrimidine-5-carbonyl)-pyridin-3-yl]-3-(3-fluoro-phenyl)-urea;
1-[5-(4-Amino-7-methyl-7H-pyrrolo[2,3-d]pyrimidine-5-carbonyl)-pyridin-3-yl]-3-o-tolyl-urea;
1-[5-(4-Amino-7-methyl-7H-pyrrolo[2,3-d]pyrimidine-5-carbonyl)-pyridin-3-yl]-3-(4-fluoro-phenyl)-urea;
1-[5-(4-Amino-7-methyl-7H-pyrrolo[2,3-d]pyrimidine-5-carbonyl)-pyridin-3-yl]-3-(2-fluoro-phenyl)-urea;
1-[5-(4-Amino-7-methyl-7H-pyrrolo[2,3-d]pyrimidine-5-carbonyl)-pyridin-3-yl]-3-(3-cyano-phenyl)-urea;
1-[5-(4-Amino-7-methyl-7H-pyrrolo[2,3-d]pyrimidine-5-carbonyl)-pyridin-3-yl]-3-(4-methoxy-phenyl)-urea;
1-[5-(4-Amino-7-methyl-7H-pyrrolo[2,3-d]pyrimidine-5-carbonyl)-pyridin-3-yl]-3-(3,5-dimethyl-phenyl)-urea;
1-[5-(4-Amino-7-methyl-7H-pyrrolo[2,3-d]pyrimidine-5-carbonyl)-pyridin-3-yl]-3-(2,6-dimethyl-phenyl)-urea;
1-[5-(4-Amino-7-methyl-7H-pyrrolo[2,3-d]pyrimidine-5-carbonyl)-pyridin-3-yl]-3-(2-fluoro-5-methyl-phenyl)-urea;
1-[5-(4-Amino-7-methyl-7H-pyrrolo[2,3-d]pyrimidine-5-carbonyl)-pyridin-3-yl]-3-(2,3-dimethyl-phenyl)-urea;
1-[5-(4-Amino-7-methyl-7H-pyrrolo[2,3-d]pyrimidine-5-carbonyl)-pyridin-3-yl]-3-(2-chloro-phenyl)-urea;
1-[5-(4-Amino-7-methyl-7H-pyrrolo[2,3-d]pyrimidine-5-carbonyl)-pyridin-3-yl]-3-(3,4-dimethyl-phenyl)-urea;
1-[5-(4-Amino-7-methyl-7H-pyrrolo[2,3-d]pyrimidine-5-carbonyl)-pyridin-3-yl]-3-(3,4-difluoro-phenyl)-urea;
1-[5-(4-Amino-7-methyl-7H-pyrrolo[2,3-d]pyrimidine-5-carbonyl)-pyridin-3-yl]-3-(4-ethyl-phenyl)-urea;
1-[5-(4-Amino-7-methyl-7H-pyrrolo[2,3-d]pyrimidine-5-carbonyl)-pyridin-3-yl]-3-(2,6-difluoro-phenyl)-urea;
1-[5-(4-Amino-7-methyl-7H-pyrrolo[2,3-d]pyrimidine-5-carbonyl)-pyridin-3-yl]-3-(2-ethyl-phenyl)-urea;
1-[5-(4-Amino-7-methyl-7H-pyrrolo[2,3-d]pyrimidine-5-carbonyl)-pyridin-3-yl]-3-(2,5-dimethyl-phenyl)-urea;
1-[5-(4-Amino-7-methyl-7H-pyrrolo[2,3-d]pyrimidine-5-carbonyl)-pyridin-3-yl]-3-(2,4-difluoro-phenyl)-urea;
1-[5-(4-Amino-7-methyl-7H-pyrrolo[2,3-d]pyrimidine-5-carbonyl)-pyridin-3-yl]-3-(3-chloro-phenyl)-urea;
1-[5-(4-Amino-7-methyl-7H-pyrrolo[2,3-d]pyrimidine-5-carbonyl)-pyridin-3-yl]-3-(2,4-dimethoxy-phenyl)-urea;
1-[5-(4-Amino-7-methyl-7H-pyrrolo[2,3-d]pyrimidine-5-carbonyl)-pyridin-3-yl]-3-(4-chloro-phenyl)-urea;
1-[5-(4-Amino-7-methyl-7H-pyrrolo[2,3-d]pyrimidine-5-carbonyl)-pyridin-3-yl]-3-(2,4-dimethyl-phenyl)-urea;
1-[5-(4-Amino-7-methyl-7H-pyrrolo[2,3-d]pyrimidine-5-carbonyl)-pyridin-3-yl]-3-(2-methoxy-5-methyl-phenyl)-urea;
1-[5-(4-Amino-7-methyl-7H-pyrrolo[2,3-d]pyrimidine-5-carbonyl)-pyridin-3-yl]-3-(3-trifluoromethyl-phenyl)-urea;
1-[5-(4-Amino-7-methyl-7H-pyrrolo[2,3-d]pyrimidine-5-carbonyl)-pyridin-3-yl]-3-(3,5-difluoro-phenyl)-urea;
1-[5-(4-Amino-7-methyl-7H-pyrrolo[2,3-d]pyrimidine-5-carbonyl)-pyridin-3-yl]-3-(2,4-dichloro-phenyl)-urea;
1-[5-(4-Amino-7-methyl-7H-pyrrolo[2,3-d]pyrimidine-5-carbonyl)-pyridin-3-yl]-3-(3-chloro-4-methyl-phenyl)-urea;
1-[5-(4-Amino-7-methyl-7H-pyrrolo[2,3-d]pyrimidine-5-carbonyl)-pyridin-3-yl]-3-(2,3-dichloro-phenyl)-urea;
1-[5-(4-Amino-7-methyl-7H-pyrrolo[2,3-d]pyrimidine-5-carbonyl)-pyridin-3-yl]-3-(4-chloro-2-methyl-phenyl)-urea;
and the pharmaceutically acceptable salts, prodrugs, hydrates and solvates of the aforementioned compounds.

Specific most preferred compounds of formula 1 are selected from the group consisting of:

1-[5-(4-Amino-7-isopropyl-7H-pyrrolo[2,3-d]pyrimidine-5-carbonyl)-pyridin-3-yl]-3-(2-fluoro-5-methyl-phenyl)-urea;

1-[5-(4-Amino-7-isopropyl-7H-pyrrolo[2,3-d]pyrimidine-5-carbonyl)-pyridin-3-yl]-3-(4-chloro-phenyl)-urea;

1-[5-(4-Amino-7-isopropyl-7H-pyrrolo[2,3-d]pyrimidine-5-carbonyl)-pyridin-3-yl]-3-(2,4-dichloro-phenyl)-urea;

1-[5-(4-Amino-7-isopropyl-7 H-pyrrolo[2,3-d]pyrimidine-5-carbonyl)-pyridin-3-yl]-3-p-tolyl-urea;

1-[5-(4-Amino-7-isopropyl-7H-pyrrolo[2,3-d]pyrimidine-5-carbonyl)-pyridin-3-yl]-3-m-tolyl-urea;

1-[5-(4-Amino-7-isopropyl-7H-pyrrolo[2,3-d]pyrimidin-3-yl]-3-(2-fluoro-phenyl)-urea;

1-[5-(4-Amino-7-isopropyl-7H-pyrrolo[2,3-d]pyrimidine-5-carbonyl )-pyridin-3-yl]-3-(3-fluoro-phenyl)-urea;

1-[5-(4-Amino-7-isopropyl-7H-pyrrolo[2,3-d]pyrimidine-5-carbonyl)-pyridin-3-yl]-3-(4-fluoro-phenyl)-urea;

1-[5-(4-Amino-7-isopropyl-7H-pyrrolo[2,3-d]pyrimidine-5-carbonyl)-pyridin-3-yl]-3-(3,5-dimethyl-phenyl)-urea;

1-[5-(4-Amino-7-isopropyl-7H-pyrrolo[2,3-d]pyrimidine-5-carbonyl)-pyridin-3-yl]-3-(4-methoxy-phenyl)-urea;

1-[5-(4-Amino-7-isopropyl-7H-pyrrolo[2,3-d]pyrimidine-5-carbonyl)-pyridin-3-yl]-3-(2-chloro-phenyl)-urea;

1-[5-(4-Amino-7-isopropyl-7 H-pyrrolo[2,3-d]pyrimidine-5-carbonyl )-pyridin-3-yl]-3-(3-chloro-phenyl)-urea;

1-[5-(4-Amino-7-isopropyl-7H-pyrrolo[2, 3-d]pyrimidine-5-carbonyl )-pyridin-3-yl]-3-(3,5-difluoro-phenyl)-urea;

1-[5-(4-Amino-7-isopropyl-7H-pyrrolo[2,3-d]pyrimidine-5-carbonyl)-pyridin-3-yl] -3-(3,4-difluoro-phenyl)-urea;

1-[5-(4-Amino-7-isopropyl-7 H-pyrrolo[2,3-d]pyrimidine-5-carbonyl)-pyridin-3-yl]-3-(2,6-difluoro-phenyl)-urea;

1-[5-(4-Amino-7-isopropyl-7H-pyrrolo[2,3-d]pyrimidine-5-carbonyl)-pyridin-3-yl]-3-(2,4-difluoro-phenyl)-urea;

1-[5-(4-Amino-7-isopropyl-7H-pyrrolo[2,3-d]pyrimidine-5-arbonyl)-pyridin-3-yl]-3-(2-methoxy-5-methyl-phenyl)-urea;

1-[5-(4-Amino-7-isopropyl-7H-pyrrolo[2,3-d]pyrimidine-5-carbonyl)-pyridin-3-yl]-3-(3-chloro4-methyl-phenyl)-urea;

1-[5-(4-Amino-7-isopropyl-7 H-pyrrolo[2,3-d]pyrimidine-5-carbonyl)-pyridin-3-yl]-3-(4-chloro-2-methyl-phenyl)-urea;

1-[5-(4-Amino-7-isopropyl-7H-pyrrolo[2,3-d]pyrimidine-5-carbonyl)-pyridin-3-yl]-3-(3,5-dimethoxy-phenyl)-urea;

1-[5-(4-Amino-7-isopropyl-7H-pyrrolo[2,3-d]pyrimidine-5-carbonyl)-pyridin-3-yl]-3-(3-trifluoromethyl-phenyl)-urea;

1-[5-(4-Amino-7-isopropyl-7H-pyrrolo[2,3-d]pyrimidine-5-carbonyl )-pyridin-3-yl]-3-(2,3-dichloro-phenyl)-urea;

and the pharmaceutically acceptable salts, prodrugs, hydrates and solvates of the aforementioned compounds.

The present invention also relates to a pharmaceutical composition for the treatment of abnormal cell growth in a mammal comprising an amount of a compound of formula 1 or a pharmaceutically acceptable salt, prodrug, solvate or hydrate thereof that is effective in treating abnormal cell growth, and a pharmaceutically acceptable carrier.

The present invention also relates to a pharmaceutical composition for the treatment of abnormal cell growth in a mammal comprising an amount of a compound of formula 1 or a pharmaceutically acceptable salt, prodrug, solvate or hydrate thereof that is effective in treating abnormal cell growth, and at least one anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

The present invention also relates to a pharmaceutical composition for the treatment of abnormal cell growth in a mammal comprising an amount of a compound of formula 1 or a pharmaceutically acceptable salt, prodrug, solvate or hydrate thereof, in combination with an amount of one or more substances selected from anti-angiogenesis agents, signal transduction inhibitors, and antiproliferative agents, which amounts are together effective in treating said abnormal cell growth.

An embodiment of the present invention includes those pharmaceutical compositions for the treatment of abnormal growth wherein the abnormal cell growth is cancer.

Other embodiments of the present invention include those pharmaceutical compositions for the treatment of abnormal cell growth, wherein the cell growth is a non-cancerous hyperproliferative disorder, such as benign hyperplasia of the skin or prostrate.

The present invention also relates to pharmaceutical composition for the treatment of pancreatitis or kidney disease in a mammal comprising an amount of a compound of formula 1 or a pharmaceutically acceptable salt, prodrug, solvate or hydrate thereof that is effective in treating said pancreatitis or kidney disease, and a pharmaceutically acceptable carrier. Examples of kidney disease include proliferative gloremerulonephritis or diabetes-induced renal disease.

The present invention also relates to a pharmaceutical composition for the prevention of blastocyte implantation in a mammal comprising an amount of a compound of formula 1 or a pharmaceutically acceptable salt, prodrug, solvate or hydrate thereof that is effective in preventing said blastocyte implantation, and a pharmaceutically acceptable carrier.

The present invention also relates to a pharmaceutical composition for the treatment of a disease relating to vasculogenesis or angiogenesis in a mammal comprising an amount of a compound of formula 1 or a pharmaceutically acceptable salt, prodrug, solvate or hydrate thereof that is effective in treating said disease, and a pharmaceutically acceptable carrier. Examples of said disease include tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The present invention also relates to a method for the treatment of abnormal cell growth in a mammal comprising administering to said mammal an amount of a compound of claim 1 or a pharmaceutically acceptable salt, prodrug, solvate or hydrate thereof that is effective in treating said abnormal cell growth. Examples of abnormal cell growth include cancer and non-cancerous cell growths such as benign hyperplasia of the skin or prostrate.

In one embodiment of the invention, the present method for the treatment of cancer includes those cancers selected from the group consisting of lung cancer, bone cancer, pancreatic cancer, gastric, skin cancer, cancer of the head or neck, cutaneous or intraocular melanoma, uterine cancer, ovarian cancer, gynecological, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, squamous cell, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain, pituitary adenoma, or a combination of one or more of the foregoing cancers.

Other embodiments of the invention include those methods for the treatment of cancer wherein the cancer is selected from the group consisting of brain, squamous cell, bladder, gastric, pancreatic, breast, head, neck, oesophageal, prostate, colorectal, lung, renal, kidney, ovarian, gynecological and thyroid cancer.

Other embodiments of the invention include those methods for the treatment of cancer wherein the cancer is selected from the group consisting of prostate, breast, lung, colon and ovarian cancer.

Other embodiments of the invention include those methods for the treatment of cancer wherein the cancer is selected from the group consisting of prostate, breast, and lung cancer.

Other embodiments of the invention include those methods for the treatment of cancer wherein the cancer is metastatic breast cancer.

Other embodiments of the invention include those methods for the treatment of cancer wherein the cancer is non-small cell lung cancer.

The present invention also relates to a method for the treatment of vasculogenesis, restenosis, atherosclerosis or angiogenesis in a mammal comprising administering to said mammal a therapeutically effective amount of a compound of formula 1 or a pharmaceutically acceptable salt, prodrug, solvate or hydrate thereof that is effective in treating said vasculogenesis, restenosis, atherosclerosis or angiogenesis. Examples of such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi*, *Yersinia* spp., *Bordetella pertussis*, and group A *Streptococcus*.

An embodiment of the present invention includes those methods of treatment wherein the treatment is for vasculogenesis or angiogenesis.

An embodiment of the present invention includes those methods of treatment wherein the treatment is for angiogenesis.

The present invention also relates to a method for the treatment of a hyperproliferative disorder in a mammal which comprises administering to said mammal a therapeutically effective amount of a compound of formula 1 or a pharmaceutically acceptable salt, prodrug, solvate or hydrate thereof in combination with at least one anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

The present invention also relates to a method for the treatment of a hyperproliferative disorder in a mammal which comprises administering to said mammal an amount of a compound of formula 1 or a pharmaceutically acceptable salt, prodrug, solvate or hydrate thereof in combination with an amount of one or more substances selected from anti-angiogenesis agents, signal transduction inhibitors, and antiproliferative agents, which amounts are together effective in treating said hyperproliferative disorder.

The present invention also relates to a method for the treatment of pancreatitis or kidney disease in a mammal which comprises administering to said mammal a therapeutically effective amount of a compound of formula 1, or a pharmaceutically acceptable salt, prodrug or hydrate thereof.

The present invention also relates to a method for the prevention of blastocyte implantation in a mammal comprising administering to said mammal an amount of a compound of formula 1, or a pharmaceutically acceptable salt, prodrug or hydrate thereof that is effective for said prevention of blastocyte implantation.

The present invention also relates to a process for preparing a compound of the formula 1

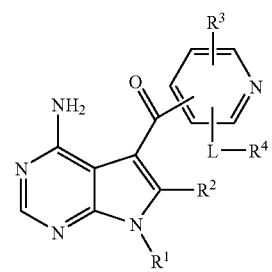

wherein:

L is —O—; —S—; —S(O)—; —S(O)$_2$—; —N(R)—; —N(C(O)OR)—; —N(C(O)R)—; —N(S(O)$_2$R)—; —C(O)N(R)—; —N(R)C(O)—; —N(R)S(O)—; —N(R)S(O)$_2$—; —OC(O)N(R)—; —N(R)C(O)N(R)—; —N(R)C(O)O—; —S(O)N(R)—; —S(O)$_2$N(R)—; or —N═; wherein each R independently is H, (C$_1$-C$_6$)alkylC(O), (C$_1$-C$_6$)alkyl, (C$_6$-C$_{10}$)aryl or (C$_1$-C$_{10}$)heteroaryl; wherein each of the aforesaid (C$_1$-C$_6$) alkylC(O), (C$_1$-C$_6$)alkyl, (C$_6$-C$_{10}$)aryl, and (C$_1$-C$_{10}$) heteroaryl groups is independently optionally substituted with 1 to 5 substituents independently selected from halogen, (C$_1$-C$_6$)alkyl and (C$_1$-C$_6$)alkoxy;

each of R$^1$ and R$^2$ is independently H, (C$_1$-C$_6$)alkyl, (C$_3$-C$_8$)cycloalkyl, (C$_6$-C$_{10}$)aryl, (C$_1$-C$_{10}$)heteroaryl, or (C$_1$-C$_{10}$)heterocycloalkyl; wherein each of the aforesaid ($C_1$-$C_6$)alkyl, ($C_3$-$C_8$)cycloalkyl, ($C_6$-$C_{10}$)aryl, ($C_1$-$C_{10}$)heteroaryl, and ($C_1$-$C_{10}$)heterocycloalkyl groups is independently optionally substituted with 1 to 5 ($C_1$-$C_6$) alkyl groups;

$R^3$ is H, ($C_1$-$C_6$)alkyl, ($C_3$-$C_8$)cycloalkyl, ($C_1$-$C_6$)alkoxy, —$NH_2$, —NH($C_1$-$C_6$)alkyl, —N[($C_1$-$C_6$)alkyl]$_2$, ($C_6$-$C_{10}$)aryl, ($C_1$-$C_{10}$)heteroaryl, or ($C_1$-$C_{10}$)heterocycloalkyl; wherein each of the aforesaid ($C_1$-$C_6$)alkyl, ($C_3$-$C_8$)cycloalkyl, ($C_6$-$C_{10}$)aryl, ($C_1$-$C_{10}$)heteroaryl, and ($C_1$-$C_{10}$)heterocycloalkyl groups is independently optionally substituted with 1 to 5 ($C_1$-$C_6$) alkyl groups;

$R^4$ is H, ($C_1$-$C_6$)alkyl, ($C_3$-$C_8$)cycloalkyl, -($CR^5R^6$)$_t$($C_6$-$C_{10}$)aryl, —($CR^5R^6$)$_t$($C_1$-$C_{10}$)heteroaryl, ($C_3$-$C_8$)heterocycloalkyl, or $CR^7R^8$; wherein $R^4$ is $CR^7R^8$ only when L is —N=; wherein t is an integer from 0 to 6; and each of the aforesaid ($C_1$-$C_6$)alkyl, ($C_3$-$C_8$)cycloalkyl, —($CR^5R^6$)$_t$($C_6$-$C_{10}$)aryl, —($CR^5R^6$)$_t$($C_1$-$C_{10}$)heteroaryl, and ($C_3$-$C_8$)heterocycloalkyl groups is independently optionally substituted with 1 to 5 $R^9$ groups;

each of $R^5$ and $R^6$ is independently selected from H and ($C_1$-$C_6$)alkyl;

each of $R^7$ and $R^8$ is independently ($C_1$-$C_6$)alkyl, ($C_3$-$C_8$)cycloalkyl, —($CR^5R^6$)$_t$($C_6$-$C_{10}$)aryl, —($CR^5R^6$)$_t$($C_1$-$C_{10}$)heteroaryl, or ($C_3$-$C_8$)heterocycloalkyl; or $R^7$ and $R^8$ may be taken together with the carbon atom to which they are attached form a ($C_3$-$C_8$)cycloalkyl, ($C_1$-$C_{10}$)heteroaryl, or a ($C_3$-$C_8$)heterocycloalkyl group; wherein t is an integer from 0 to 6; and each of the aforesaid ($C_1$-$C_6$)alkyl, ($C_3$-$C_8$)cycloalkyl, —($CR^5R^6$)$_t$($C_6$-$C_{10}$)aryl, ($C_1$-$C_{10}$)heteroaryl, —($CR^5R^6$)$_t$($C_1$-$C_{10}$)heteroaryl, and ($C_3$-$C_8$)heterocycloalkyl groups is optionally independently substituted with 1 to 5 $R^9$ groups;

each $R^9$ is independently halo, cyano, trifluoromethoxy, trifluoromethyl, ($C_1$-$C_6$)alkyl, ($C_2$-$C_6$)alkenyl, ($C_2$-$C_6$)alkynyl, or —($CR^5R^6$)$_t$$OR^{10}$; t is independently an integer from 0 to 6; any of the aforesaid —($CR^5R^6$)$_t$— moiety may optionally include a carbon-carbon double or triple bond where t is an integer from 2 to 6; and each $R^{10}$ is independently hydrogen or ($C_1$-$C_6$)alkyl; which comprises treating a compound of formula 2 wherein Z is halo

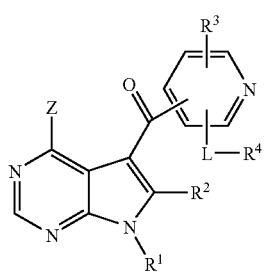

2 with ammonia or ammonium hydroxide.

In one embodiment of the present invention, the process for preparing the compound of formula 1 from the compound of formula 2 includes those compounds wherein Z is chlorine.

The present invention also relates to a process for preparing a compound of the formula 3

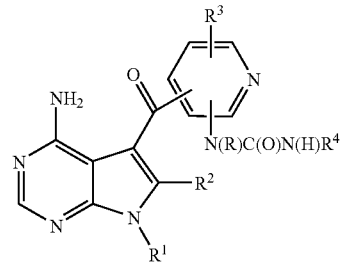

3 wherein:
R is H, ($C_1$-$C_6$)alkylcarbonyl, ($C_1$-$C_6$)alkyl, ($C_6$-$C_{10}$)aryl or ($C_1$-$C_{10}$)heteroaryl; wherein each of the aforesaid ($C_1$-$C_6$)alkylcarbonyl, ($C_1$-$C_6$)alkyl, ($C_6$-$C_{10}$)aryl, and ($C_1$-$C_{10}$)heteroaryl groups is independently optionally substituted with 1-3 substituents independently selected from halogen, ($C_1$-$C_6$)alkyl and ($C_1$-$C_6$)alkoxy;

each of $R^1$ and $R^2$ is independently H, ($C_1$-$C_6$)alkyl, ($C_3$-$C_8$)cycloalkyl, ($C_6$-$C_{10}$)aryl, ($C_1$-$C_{10}$)heteroaryl, or ($C_1$-$C_{10}$)heterocycloalkyl; wherein each of the aforesaid ($C_1$-$C_6$)alkyl, ($C_3$-$C_8$)cycloalkyl, ($C_6$-$C_{10}$)aryl, ($C_1$-$C_{10}$)heteroaryl, and ($C_1$-$C_{10}$)heterocycloalkyl groups is independently optionally substituted with 1 to 5 ($C_1$-$C_6$) alkyl groups;

$R^3$ is H, ($C_1$-$C_6$)alkyl, ($C_3$-$C_8$)cycloalkyl, ($C_1$-$C_6$)alkoxy, —$NH_2$, —NH($C_1$-$C_6$)alkyl, —N[($C_1$-$C_6$)alkyl]$_2$, ($C_6$-$C_{10}$)aryl, ($C_1$-$C_{10}$)heteroaryl, or ($C_1$-$C_{10}$)heterocycloalkyl; wherein each of the aforesaid ($C_1$-$C_6$)alkyl, ($C_3$-$C_8$)cycloalkyl, ($C_6$-$C_{10}$)aryl, ($C_1$-$C_{10}$)heteroaryl, and ($C_1$-$C_{10}$)heterocycloalkyl groups is independently optionally substituted with 1 to 5 ($C_1$-$C_6$)alkyl groups;

$R^4$ is H, ($C_1$-$C_6$)alkyl, ($C_3$-$C_8$)cycloalkyl, —($CR^5R^6$)$_t$($C_6$-$C_{10}$)aryl, —($CR^5R^6$)$_t$($C_1$-$C_{10}$)heteroaryl, or ($C_3$-$C_8$)heterocycloalkyl; wherein t is independently an integer from 0 to 6; and each of the aforesaid ($C_1$-$C_6$)alkyl, ($C_3$-$C_8$)cycloalkyl, —($CR^5R^6$)$_t$($C_6$-$C_{10}$)aryl, —($CR^5R^6$)$_t$($C_1$-$C_{10}$)heteroaryl, and ($C_3$-$C_8$)heterocycloalkyl groups is optionally independently substituted with 1 to 5 $R^9$ groups;

each of $R^5$ and $R^6$ is independently selected from H and ($C_1$-$C_6$)alkyl;

each $R^9$ is independently halo, cyano, trifluoromethoxy, trifluoromethyl, ($C_1$-$C_6$)alkyl, ($C_2$-$C_6$)alkenyl, ($C_2$-$C_6$)alkynyl, —($CR^5R^6$)$_t$$OR^{10}$; t is independently an integer from 0 to 6; the —($CR^5R^6$)$_t$— moiety may optionally include a carbon-carbon double or triple bond where t is an integer from 2 to 6; and each $R^{10}$ is independently hydrogen or ($C_1$-$C_6$)alkyl; which comprises treating a compound of the formula 4

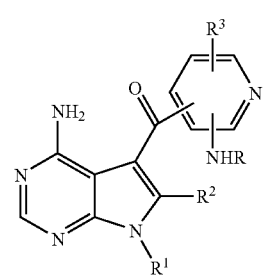

4 wherein R, $R^1$, $R^2$, $R^3$ and $R^4$ have the same meaning as set forth above for formula 3; with a compound of formula $R^4$—N═C═O wherein $R^4$ has the same meaning as set forth above for formula 3.

The present invention also relates to a process for preparing a compound of the formula 5

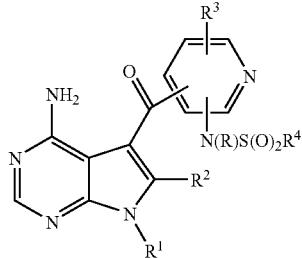

wherein:
- R is H, $(C_1-C_6)$alkylcarbonyl, $(C_1-C_6)$alkyl, $(C_6-C_{10})$aryl or $(C_1-C_{10})$heteroaryl; wherein each of the aforesaid $(C_1-C_6)$alkylcarbonyl, $(C_1-C_6)$alkyl, $(C_6-C_{10})$aryl, and $(C_1-C_{10})$heteroaryl groups is independently optionally substituted with 1 to 3 substituents independently selected from halogen, $(C_1-C_6)$alkyl and $(C_1-C_6)$alkoxy;
- each of $R^1$ and $R^2$ is independently H, $(C_1-C_6)$alkyl, $(C_3-C_8)$cycloalkyl, $(C_6-C_{10})$aryl, $(C_1-C_{10})$heteroaryl, or $(C_1-C_{10})$heterocycloalkyl; wherein each of the aforesaid $(C_1-C_6)$alkyl, $(C_3-C_8)$cycloalkyl, $(C_6-C_{10})$aryl, $(C_1-C_{10})$heteroaryl, and $(C_1-C_{10})$heterocycloalkyl groups is independently optionally substituted with 1 to 5 $(C_1-C_6)$ alkyl groups;
- $R^3$ is H, $(C_1-C_6)$alkyl, $(C_3-C_8)$cycloalkyl, $(C_1-C_6)$alkoxy, —$NH_2$, —NH$(C_1-C_6)$alkyl, —N[$(C_1-C_6)$alkyl]$_2$, $(C_6-C_{10})$aryl, $(C_1-C_{10})$heteroaryl, or $(C_1-C_{10})$heterocycloalkyl; wherein each of the aforesaid $(C_1-C_6)$alkyl, $(C_3-C_8)$cycloalkyl, $(C_6-C_{10})$aryl, $(C_1-C_{10})$heteroaryl, and $(C_1-C_{10})$heterocycloalkyl groups is independently optionally substituted with 1 to 5 $(C_1-C_6)$alkyl groups;
- $R^4$ is H, $(C_1-C_6)$alkyl, $(C_3-C_8)$cycloalkyl, —$(CR^5R^6)_t(C_6-C_{10})$aryl, —$(CR^5R^6)_t(C_1-C_{10})$heteroaryl, or $(C_3-C_8)$heterocycloalkyl; wherein t is independently an integer from 0 to 6; and each of the aforesaid $(C_1-C_6)$alkyl, $(C_3-C_8)$cycloalkyl, —$(CR^5R^6)_t(C_6-C_{10})$aryl, —$(CR^5R^6)_t(C_1-C_{10})$heteroaryl, and $(C_3-C_8)$heterocycloalkyl groups is optionally independently substituted with 1 to 5 $R^9$ groups;
- each of $R^5$ and $R^6$ is independently selected from H and $(C_1-C_6)$alkyl;
- each $R^9$ is independently halo, cyano, trifluoromethoxy, trifluoromethyl, $(C_1-C_6)$alkyl, $(C_2-C_6)$alkenyl, $(C_2-C_6)$alkynyl, —$(CR^5R^6)_tOR^{10}$; t is independently an integer from 0 to 6; the —$(CR^5R^6)_t$— moiety may optionally include a carbon-carbon double or triple bond where t is an integer from 2 to 6; and
- each $R^{10}$ is independently hydrogen or $(C_1-C_6)$alkyl;

which comprises treating a compound of the formula 4

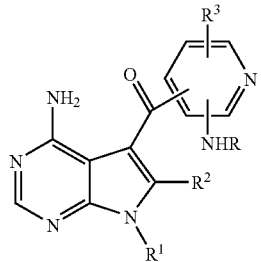

wherein R, $R^1$, $R^2$, $R^3$ and $R^4$ have the same meaning as set forth above for formula 5; with a compound of formula $R^4$—S$(O)_2$Cl wherein $R^4$ has the same meaning as set forth above for formula 5.

A compound of formula 1 can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), ABX-EGF (Abgenix/Cell Genesys), EMD-7200 (Merck KgaA), EMD-5590 (Merck KgaA), MDX-447/H-477 (Medarex Inc. of Annandale, N.J., USA and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co. of Whitehouse Station, N.J., USA), VRCTC-310 (Ventech Research), EGF fusion toxin (Seragen Inc. of Hopkinton, Mass.), DAB-389 (Seragen/Lilgand), ZM-252808 (Imperical Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGFR Vaccine (York Medical/Centro de Immunologia Molecular (CIM)). These and other EGFR-inhibiting agents can be used in the present invention.

VEGF inhibitors, for example CP-547,632 and AG-13736, SU-11246, SU-5416 and SU-6668 (Pfizer Inc.), SH-268 (Schering), and NX-1838 (NeXstar) can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Patent No. US 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as CP -724,714 (Pfizer, Inc.), GW-2016, GW-282974, and GW-572016 (Glaxo Wellcome plc), TAK-165 (Takeda) and the monoclonal antibodies AR-209 (Aronex Pharmaceuticals Inc. of The Woodlands, Tex., USA) and 2B-1 (Chiron), can furthermore be combined with the compound of the invention. Such erbB2 inhibitors include Herceptin™, 2C4, and pertuzumab. Such erbB2 include those described in WO 98/02434 (published Jan. 22, 1998), WO 99/35 146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO/00/44728 (published Aug. 3, 2000), EP 1029853A1 (published Aug. 23, 2000), and WO01/ 98277 (published Dec. 12, 2001) all of which are incorporated herein by reference in their entirety.

The compound of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and inhibitors of inhibitors of the receptor tyrosine kinase PDGFr, including the compounds disclosed and claimed in the following U.S. patent applications: Ser. No. 09/221946 (filed Dec. 28, 1998); Ser. No. 09/454058 (filed Dec. 2, 1999); Ser. No. 09/501163 (filed Feb. 9, 2000); Ser. No. 09/539930 (filed Mar. 31, 2000); Ser. No. 09/202796 (filed May 22, 1997); Ser. No. 09/384339 (filed Aug. 26, 1999); and Ser. No. 09/383755 (filed Aug. 26, 1999); and the compounds disclosed and claimed in the following U.S. provisional patent applications: No. 60/168207 (filed Nov. 30, 1999); No. 60/170119 (filed Dec. 10, 1999); No. 60/177718 (filed Jan. 21, 2000); No. 60/168217 (filed Nov. 30, 1999), and No. 60/200834 (filed May 1, 2000). Each of the foregoing patent applications and provisional patent applications is herein incorporated by reference in their entirety. Specific CTLA4 antibodies that can be used in the present invention include those described in U.S. Provisional Application No. 60/113,647 (filed Dec. 23, 1998) which is incorporated by reference in its entirety; however other CTLA4 antibodies can be used in the present invention.

Other anti-angiogenesis agents, including, but not limited to, CI-1040, CI-1030 and CI-994 (all of the foregoing of Pfizer, Inc.) other COX-II (cyclooxygenase II) inhibitors, other MMP (matrix-metalloproteinase) inhibitors, such as MMP-2 and MMP-9 inhibitors, other anti-VEGF antibodies or inhibitors of other effectors of vascularization can also be used in conjunction with the compound of formula 1 in the present invention.

Examples of useful COX-II inhibitors include CELEBREX™ (celecoxib), Bextra™ (valdecoxib), paracoxib, Vioxx™ (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety.

Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxy-carbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran4-carboxylic acid hydroxyamide;

3-[[4-(4-fluoro-phenoxy)-benzenesulfonyl]-(1-hydroxy-carbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxy-carbamoyl-1-methyl-ethyl)-amino]-propionic acid;

3-[[4-(4-fluoro-phenoxy)-benzenesulfonyl]-(4-hydroxy-carbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1 ]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

The compounds of the present invention may be used alone or in combination with one or more of a variety of anti-cancer agents or supportive care agents. For example, the compounds of the present invention may be used with cytotoxic agents, e.g., one or more selected from the group consisting of a camptothecin, irinotecan HCI (Camptosar™), edotecarin, SU-11248, epirubicin (Ellence™), docetaxel (Taxotere™), paclitaxel, rituximab (Rituxan™) bevacizumab (Avastin™), imatinib mesylate (Gleevec™), Erbitux, gefitinib (Iressa™), and combinations thereof. The invention also contemplates the use of the compounds of the present invention together with hormonal therapy, e.g., exemestane (Aromasin™), Lupron, anastrozole (Arimidex), tamoxifen citrate (Nolvadex), triptorelin pamoate (Trelstar™), and combinations thereof. Further, the invention provides a compound of the present invention alone or in combination with one or more supportive care products, e.g., a product selected from the group consisting of Filgrastim (Neupogen™), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds of the invention may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds of the invention.

Alkylating agents include, but are not limited to: AMD-473, altretamine, AP-5280, apaziquone, brostallicin, bendamustine, busulfan, carboquone, carmustine, cyclophosphamide, estramustine, fotemustine, glufosfamide, ifosfamide, KW-2170, mafosfamide, melphalan, mitobronitol, mitolactol, nimustine, nitrogen mustard N-oxide, temozolomide, thiotepa and ranimustine. Platinum-coordinated alkylating compounds include but are not limited to, cisplatin, carboplatin, eptaplatin, lobaplatin, nedaplatin, oxaliplatin or satrplatin.

Antimetabolites include but are not limited to: 5-azacitidine, capecitabine, carmofur, cladribine, clofarabine, cytarabine, decitabine, doxifluridine, eflornithine, enocitabine, ethynylcytidine, 5-fluorouracil (5-FU) alone or in combination with leucovorin, leucovorin, cytosine arabinoside, hydroxyurea, fludarabine, TS-1, gemcitabine, methotrexate, melphalan, 6-mercaptopurine, mercaptopurine, nelarabine, nolatrexed, ocfosfate, disodium premetrexed, pentostatin, pelitrexol, raltitrexed, riboside, tegafur, triapine, trimetrexate, UFT, vidarabine, vincristine, vinorelbine,; or for example, one of the preferred anti-metabolites disclosed in European Patent Application No. 239362 such as $\underline{N}$-(5-[$\underline{N}$-(3,4-dihydro-2-methyl4-oxoquinazolin-6-ylmethyl)-$\underline{N}$-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubcin, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride, fotemustine, ibandronic acid, miltefosine, mitoxantrone, I-asparaginase, procarbazine, dacarbazine, hydroxycarbamide, pegaspargase, pentostatin, tazarotne, TLK-286 or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin;

The subject invention also includes isotopically-labelled compounds, which are identical to those recited in formula 1 but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula 1 of this invention and prodrugs thereof can generally be prepared by carrying out the procedures disclosed in the Schemes and/or in the Examples below, by substituting a readily available isotopically labeled reagent for a non-isotopically labeled reagent.

The compounds of formula 1 and their pharmaceutically acceptable salts and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

A "suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl); optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_4)$alkyl, most preferably methyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1-2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred cycloalkyls include cyclobutyl, cyclopentyl and cyclohexyl.

As used herein, the term "halogen" includes fluoro, chloro, bromo or iodo or fluoride, chloride, bromide or iodide.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "$(C_2-C_6)$alkynyl" is used herein to mean straight or branched hydrocarbon chain radicals having one triple bond including, but not limited to, ethynyl, propynyl, butynyl, and the like; optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(C=O)" (as used in phrases such as alkylcarbonyl, alkyl-(C=O)- or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "aryl" means aromatic radicals such as phenyl, naphthyl, tetrahydronaphthyl, indanyl and the like; optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^4$ heteroaryls).

The term "heterocycloalkyl" as used herein means a nonaromatic monovalent ring (which can include bicyclo ring systems) having from 4 to 10 members, of which, up to 4 are heteroatoms such as N, O and S for example. The heterocycloalkyl groups of this invention can also include ring systems substituted with one or more oxo moieties. Heterocycloalkyl groups may be unsubstituted or substituted with those substituents enumerated for cycloalkyl. Examples of heterocycloalkyl groups include, but are not limited to, 2- or 3-tetrahydrothieno, 2- or 3-tetrahydrofurano, 1-, 2- or 3-pyrrolidino, 2-, 4-, or 5-thiazolidino, 2-, 4-, or 5-oxazolidino, 2-, 3-, or 4-piperidino, N-morpholinyl, N-thiamorpholinyl, 3-azabicyclo[3.1.0]hexanyl, 3-azabicyclo[4.1.0]heptanyl, 1,4-dioxaspiro[4.5]decyl, 1,4-dioxaspiro[4.4]nonyl, 1,4-dioxaspiro[4.3]octyl, and 1,4-dioxaspiro[4.2]heptyl. Examples of substituted heterocycloalkyl groups include, but are not limited to, 1-methyl-pyrrolidin-3-yl, 1-acetyl-pyrrolidin-3-yl, 1-methyl-piperidin-4-yl, 1-acetyl-piperidin-4-yl, 1-methyl-azetidin-3-yl, 1-acetyl-azetidin-3-yl, 2-oxo-piperidin-1-yl, and 2,3-Dimethyl-1,4-dioxa-spiro[4.4]nonyl.

As used herein, the phrase "heterocyclic ring" in the context of the phrase "$R^6$ and $R^7$ taken together on the same $R^8$ or on the same $R^{12}$ can form a heterocyclic ring" refers to a nonaromatic ring having from 4 to 8 members, of which at least 1 is a N atom, and up to 4 of which are heteroatoms such as N, O and S for example. The heterocyclic ring may be unsubstituted or substituted on a carbon atom with those substituents enumerated for cycloalkyl. Examples of such heterocyclic rings include pyrrolidine, piperidine, piperazine, morpholine, and thiamorpholine.

The term "alkoxy", as used herein, unless otherwise indicated, means O-alkyl groups wherein "alkyl" is as defined above.

The term "acyl", as used herein, refers to a species containing a carbon-oxygen double bond.

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature are capable of forming base salts with various pharmacologically acceptable cations. Examples of such salts include the alkali metal or alkaline earth metal salts and particularly, the sodium and potassium salts.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I may also exist as tautomers. This invention relates to the use of all such tautomers and mixtures thereof.

This invention also encompasses pharmaceutical compositions containing and methods of treating proliferative disorders or abnormal cell growth through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Each of the patents, patent applications, published International applications, and scientific publications referred to in this patent application is incorporated herein by reference in its entirety.

DETAILED DESCRIPTION OF THE INVENTION

The compounds of the present invention are readily prepared according to synthetic methods familiar to those skilled in the art. Scheme 1 illustrates a general synthetic sequence for preparing compounds of the present invention where $R_2$ is a hydrogen atom (H).

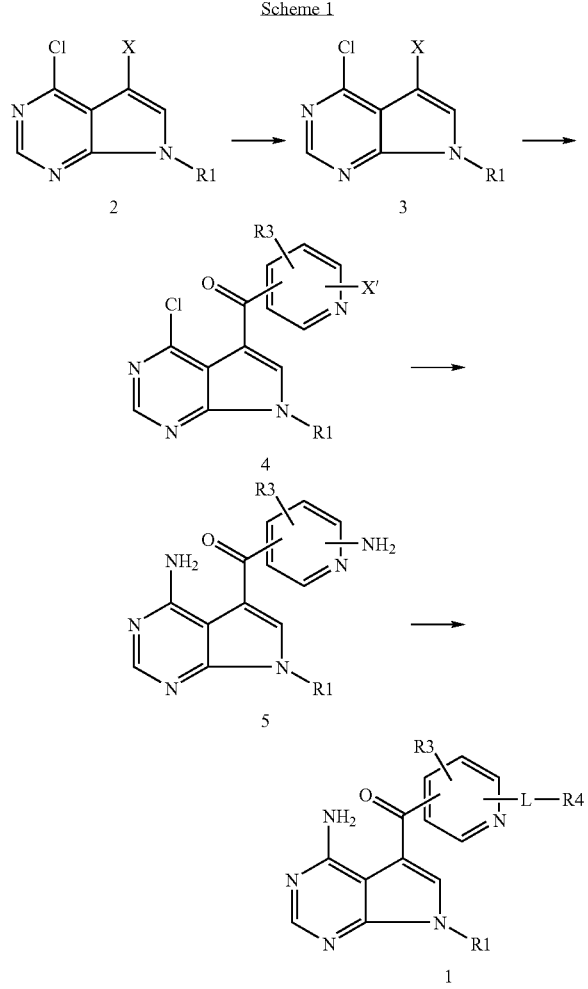

Compound 2 (X=H, Br or I) may be prepared according to literature procedures, for example, described by Townsend et al: J. Med. Chem. 1990, 33(7), 1984-1992 or by Ugarkar et al: J. Med. Chem. 2000, 43(15), 2883. The group $R^1$ in compound 3 may be H, alkyl, cycloalkyl, heteroalkyl, heterocyclic, aromatic or heteroaromatic moieties with or without additional substituents chosen from one or more of the following entities: hydroxyl, alkoxy, amino, substituted amino, alkyl, cycloalkyl, or heterocyclic moieties. Compound 3 is usually obtained via a simple alkylation of 2, using for example, $Cs_2CO_3$/DMF in the presence of alkyl halide, or via a Mitsunobu reaction. Introduction of halogen atoms can be performed on either 2 or 3 using literature procedures, for example, described by Townsend et al: J. Med. Chem. 1990, 33(7), 1984-1992.

Compound 3 (X=Br) may be converted to 4 by treatment of 3 with, for example, n-butyllithium in a solvent, such as ethyl ether ($Et_2O$), at a temperature of about $-78°$ C. for a period of 0.5 to 1 h and followed by treatment with an acyl chloride (BCOCl) or Wenreib amide. The preferred acyl chlorides or Wenreib amides usually have the acyl group attached directly to a pyridine moiety. Furthermore, a halogen group or protected amino group may be attached directly to the pyridyl moiety at various positions. The pyridyl moiety of the acyl chloride usually is an unsubstituted six membered aromatic ring, or substituted with halogen, alkoxy, or small alkyl groups at various positions on the ring.

The chlorine atom and X' (Br or Cl) of compound 4 may be replaced with an amino group by treatment of the compound with ammonia hydroxide at elevated temperature and pressure. Alternatively, the X' (protected amino) of compound 4 may be deprotected. For example, when X' equals benzophenone imine, this compound may be treated with acid such as HCl or TFA, to reveal the amino group. Compounds of the present invention may be obtained by treatment of 5 with acid chloride, sulfonyl chloride, isocyanate, or subjecting 5 under reductive alkylation condition with aldehyde or ketone, or coupling conditions with carboxylic acid. Protocols for all such chemical treatment/conversions are well established and are familiar to those practiced in the field. The reagents used in these procedures may have their reactive functional group attached directly to an aromatic moiety, or indirectly through a C1 to C3 saturated or unsaturated carbon chain, or may be attached to a non-aromatic moiety. In cases where an aromatic moiety is part of these reagents, the aromatic moiety may be a five or six membered ring, with one or more substituents of halogen, lower alkyl, lower alkoxy, additionally substituted or unsubstituted aryls. This aromatic moiety may also be fused with other aromatic ring structures. In cases where these reagents are not readily commercially available, the reagents may be prepared using protocols well established in the field, or the compounds of the present invention may be specifically synthesized using alternative methods familiar to those practice in the field, for example by converting 5 to its phenyl carbamate, and subsequently converting the carbamate into ureas.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the later back to the free base compound by treatment with an alkaline reagent and subsequently convert the latter free base to a pharmaceutically acceptable acid addition salt. The acid addition salt of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those, which form non-toxic, base salts with the acidic compounds of formula 1. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are inhibitors/antagonists of various enzymes/receptors. They are active against a variety of kinase targets which are involved in angiogenesis/vasculogenesis, oncogenic and protooncogenic signal transduction and cell cycle regulations. As such, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant ligand/receptor expression, interaction, activation or signal events related to various protein kinases, are involved. Such disorders may include those of neuronal, glial, astrocytal, hypothalamic, and other glandular macrophagal, epithelia, stromal, and blastocoelic naturein which aberrant function, expression, activation or signaling of a protein kinase are involved. In addition, the compounds of the present invention may have therapeutic utility in inflammatory, angiogenic and immunologic disorders involving both identified and as yet unidentified kinases that are inhibited by the compounds of this invention.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The compounds of the present invention have been found to be selective inhibitors of the tyrosine kinases, Tie-2, TrkA and related family member TrkB. The potentcy of the compounds of the present invention at the tyrosine kinases may be determined using the following assays.

The in vitro activity of the compounds of formula 1 in inhibiting the Tie-2 receptor may be determined by the following procedure.

Inhibition of Tie-2 tyrosine kinase activity was measured in 96-well Maxisorp plates (Nunc) coated with poly-Glu-Tyr (PGT 4:1, Sigma) by the addition of 100 µL/well of a 25 µg/mL solution of PGT in PBS. Plates were incubated at 37° C. overnight, and transferred to 4° C. until use. Prior to compound testing, appropriate dilutions of compounds were made in 96-well polypropylene plates. The compounds were diluted to 60-fold the desired final concentrations in DMSO, and subsequently diluted to 4-fold the desired final concentrations in phosphorylation buffer-DTT (PB-DTT), a buffer composed of 50 mM HEPES, pH 7.4, 125 mM NaCl, 24 mM $MgCl_2$, and 2 mM of freshly added dithiothreitol (DTT; Sigma). The PGT-coated plates were removed from 4° C., and washed 5 times with TBST, a wash buffer composed of 1×Tris-buffered saline made from powder (Sigma) containing 0.1% polyoxyethylenesorbitan monolaurate (Tween-20, Sigma). Twenty-five µL of each compound dilution per well was added to the washed PGT-coated plate. Plates then received 50 µL/well of a solution of 200 mM ATP (Sigma), freshly diluted in PB-DTT from a frozen 50 mM stock solution. Control wells received 50 µL/well PB-DTT lacking ATP. Reactions were initiated by the addition of 25 µL of purified GST-Tie2 fusion protein in PB-DTT. GST-Tie2 was previously isolated from insect cells infected with GST-Tie2 baculoviruses, and used at concentrations determined to provide $OD_{450}$ signals of approximately 1.0 in the presence of ATP and the absence of chemical inhibitors. Reactions were allowed to proceed for 15 minutes at ambient temperatures with shaking, and terminated by washing 5 times with TBST. To detect phosphotyrosine, the wash buffer was removed, and each well received 75 µL of a horseradish peroxidase-conjugated monoclonal antibody to phosphotyrosine (HRP-PY20; Signal Transduction Labs), diluted 1:2000 in block buffer, a buffer composed of wash buffer and 5% bovine serum albumin (BSA: Sigma). Plates were incubated for 30 minutes with shaking at ambient temperature, and washed 5 times with wash buffer. The bound HRP-PY20 antibody was detected by the addition of 70 µL/well TMB microwell substrate (KPL), and color development was terminated by the addition of an equal volume of 0.9 M $H_2SO_4$. The background signal from wells lacking ATP was subtracted from all ATP-stimulated wells, and $IC_{50}$ values were calculated.

The cell assay utilized NIH/3T3 fibroblasts expressing a chimeric receptor composed of the extracellular domain of the human EGFR, and the intracellular domain of human Tie-2. To measure cellular activity, fifteen thousand cells were seeded into 96-well U-bottom plates (Falcon) in Dulbecco's Modified Essential Medium (DMEM) containing 2 mM L-glutamine, 0.1 U/mL penicillin, 0.1 µg/mL streptomycin and 10% fetal calf serum (FCS; all supplements from Gibco). Cells were allowed to attach for six hours at 37° C., 5% $CO_2$, at which time the medium was replaced with 190

μL/well starvation medium (fresh medium containing 0.1% FCS). The cell plates were returned to the incubator until the next day. Prior to compound testing, appropriate dilutions of compounds were made in 96-well polypropylene plates. The initial dilution series began with the addition of 15 μL of a 4 mM compound stock solution in DMSO to 45 μL DMSO; the resulting concentration of 1 mM was diluted in a serial 1:4 fashion in DMSO to give concentrations of 1000, 250, 62.5, 15.63, 3.91, 0.98, 0.25 and 0 μM. In a separate 96-well plate, 20 μL of each compound dilution was then added to 80 μL of starvation medium to give compound concentrations of 200, 50, 12.5, 3.13, 0.78, 0.20, 0.049 and 0 μM in a final DMSO concentration of 20%. To dose cells, 10 μL of the various compound dilutions were added to the plates containing cells, to give final compound concentrations of 10, 2.5, 0.63, 0.16, 0.039, 0.01, 0.002 and 0 μM in 1% DMSO. Cell plates were allowed to incubate with compounds for 60 minutes at 37° C., 5% $CO_2$. To activate the chimeric receptors, recombinant EGF (Sigma) was added to a final concentration of 200 ng/mL, and plates were incubated for an additional 10 minutes at 37° C., 5% $CO_2$. Medium was then removed, and the cells were fixed for 5 minutes on ice with 100 μL/well cold methanol containing 200 μM $NaVO_4$. The fixative was removed and plates were allowed to dry at ambient temperature. Phosphotyrosine levels were measured in a time-resolved immunoassay with DELFIA Eu-N[1]-labeled Anti-Phosphotyrosine Antibody (PT66) from Perkin Elmer™. The antibody was diluted to a final concentration of 0.5 μg/mL in DELFIA Assay Buffer (Perkin Elmer™), and 100 μL/well was added for 60 minutes at ambient temperature with shaking. The antibody solution was removed, and plates were washed six times using 300 μL/well DELFIA Wash Buffer (Perkin Elmer™). After the final wash, 100 μL/well of DELFIA Enhancement Solution (Perkin Elmer™) was added to each well. The DELFIA Enhancement Solution (Perkin Elmer™) acts to dissociate the Europium ions, which form highly fluorescent chelates. After incubation at ambient temperatures for 5 minutes with shaking, the plates are read on a Victor 2 Multilabel HTS Counter (Perkin Elmer™). The background signal from mock-stimulated wells is subtracted from the EGF-stimulated wells, and $IC_{50}$ values are calculated.

The in vitro activity of the compounds of formula 1 in inhibiting the TrkA receptor may be determined by the following procedure.

The ability of the compounds of the present invention to inhibit tyrosine kinase activity of TrkA may be measured using a recombinant enzyme in an assay that measures the ability of compounds to inhibit the phosphorylation of the exogenous substrate, polyGluTyr (PGT, Sigma™, 4:1). The kinase domain of the human NGF/TrkA receptor is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (1.0 ug PGT per well). The final concentration of ATP in the plates is 40 uM. Test compounds are first diluted in dimethylsulfoxide (DMSO) and then serial-diluted in a 96-well plate. When added to the PGT plates, the final concentration of DMSO in the assay is 0.06%. The recombinant enzyme is diluted in phosphorylation buffer (50 mM HEPES, pH 7.4, 0.14M NaCl, 2.2 mM $MgCl_2$, 2.5 mM $MnCl_2$, 0.1 mM DTT, 0.2 mM $Na_3VO_4$). The reaction is initiated by the addition of the recombinant enzyme to the ATP and to the test compounds. After a 30 minute incubation at room temperature with shaking, the reaction is stopped with 0.5M EDTA, pH 8.0, and then aspirated. The plates are washed with wash buffer (1×imidazole wash buffer). The amount of phosphorylated PGT is quantitated by incubation with a HRP-conjugated (HRP is horseradish peroxidase) PY-54 antibody (Transduction Labs), developed with ABTS substrate, and the reaction is quantitated on a Wallac Victor[2] plate reader at 405 nm. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit TrkA tyrosine kinase activity for the full length protein that exists in a cellular context, the porcine aortic endothelial (PAE) cells transfected with the human TrkA may be used. Cells are plated and allowed to attach to 96-well dishes in the same media (Ham's F12) with 10% FBS (fetal bovine serum). Test compounds, dissolved in DMSO, are serial-diluted in 96-well assay blocks with serum free media containing 0.1% fatty-acid free bovine serum albumin (BSA). The cells are then washed, re-fed with serum free media with and without test compounds, and allowed to incubate for 2 hr. At the end of the 2 hr. incubation, NGF (150 ng/ml final) is added to the media for a 10 minute incubation. The cells are washed and lysed in Tris-lysis buffer (50 mM Tris, pH 7.4, 150 mM NaCl, 1% NP40, 10% glycerol, 2 mM $Na_3VO_4$, 0.5 mM EDTA, complete protease inhibitor cocktail tablets without EDTA). TBS is used as a diluter solution to mix the cell lysates. The extent of phosphorylation of TrkA is measured using an ELISA assay. The black, Maxisorb 96-well plates are custom-coated with goat anti-rabbit antibody (Pierce). The Trk(C-14)sc-11 antibody (Santa Cruz) at 0.4 μg/well is bound to the plates for 2 hr. in SuperBlock Blocking Buffer in TBS (Pierce). Any unbound antibody is washed off the plates prior to addition of the cell lysate. After a 2 hr. incubation of the lysates with the Trk(C-14)sc-11 antibody, the TrkA associated phosphotyrosine is quantitated by development with the HRP-conjugated PY54 antibody and SuperSignal ELISA Femto substrate (Pierce). The ability of the compounds to inhibit the NGF-stimulated autophosphorylation reaction by 50%, relative to NGF-stimulated controls, is reported as the $IC_{50}$ value for the test compound.

The in vitro activity of the compounds of formula 1 in inhibiting the TrkB receptor may be determined by the following procedure.

The ability of the compounds of the present invention to inhibit tyrosine kinase activity of TrkB may be measured using a recombinant enzyme in an assay that measures the ability of compounds to inhibit the phosphorylation of the exogenous substrate, polyGluTyr (PGT, Sigma™, 4:1). The kinase domain of the human BDNF/TrkB receptor is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (1.0 ug PGT per well). The ATP is diluted in phosphorylation buffer (50 mM HEPES, pH 7.4, 0.14M NaCl, 0.56 mM $MnCl_2$, 0.1 mM DTT, 0.2mM $Na_3VO_4$). The final concentration of ATP in the plates is 300 uM. Test compounds are first diluted in dimethylsulfoxide (DMSO) and then serial-diluted in a 96-well plate. When added to the PGT plates, the final concentration of DMSO in the assay is 0.06%. The recombinant enzyme is diluted in phosphorylation buffer without $MnCl_2$. The reaction is initiated by the addition of the recombinant enzyme to the ATP and to the test compounds. After a 2.5 hr. incubation at 30° C. with shaking, the reaction is stopped with 0.5M EDTA, pH 8.0, and then aspirated. The plates are washed with wash buffer (1×imidazole wash buffer). The amount of phosphorylated PGT is quantitated by incubation with a HRP-conjugated antiphosphotyrosine antibody, developed with ABTS substrate, and the reaction is quantitated on a Wallac Victor$^2$ plate reader at 405 nm. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit TrkB tyrosine kinase activity for the full-length protein that exists in a cellular context, the porcine aortic endothelial (PAE) cells transfected with the human TrkB may be used. Cells are plated and allowed to attach to 96-well dishes in the same media (Ham's F12) with 10% FBS (fetal bovine serum). Test compounds, dissolved in DMSO, are serial-diluted in 96-well assay blocks with serum free media containing 0.1% fatty-acid free bovine serum albumin (BSA). The cells are then washed, re-fed with serum free media with and without test compounds, and allowed to incubate for 2 hr. At the end of the 2 hr. incubation, BDNF (100 ng/ml final) is added to the media for a 10 minute incubation. The cells are washed and lysed in Tris-lysis buffer (50 mM Tris, pH 7.4, 150 mM NaCl, 1% NP-40, 10% glycerol, 2 mM $Na_3VO_4$, 0.5 mM EDTA, complete protease inhibitor cocktail tablets without EDTA). TBS is used as a diluter solution to mix the cell lysates. The extent of phosphorylation of TrkB is measured using an ELISA assay. The black, Maxisorb 96-well plates are custom-coated with goat anti-rabbit antibody (Pierce). The □-Trk(C-14)sc-11 antibody (Santa Cruz) at 0.4 □g/well is bound to the plates for 2 hr. in SuperBlock Blocking Buffer in TBS (Pierce). Any unbound antibody is washed off the plates prior to addition of the cell lysate. After a 2 hr. incubation of the lysates with the Trk(C-14)sc-11 antibody, the TrkB associated phosphotyrosine is quantitated by development with a HRP-conjugated antiphosphotyrosine antibody and SuperSignal ELISA Femto substrate (Pierce). The ability of the compounds to inhibit the BDNF-stimulated autophosphorylation reaction by 50%, relative to BDNF-stimulated controls, is reported as the $IC_{50}$ value for the test compound.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgment of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-(N-(3,4-dihydro-2-methyl-4-oxoquinazolin-6-ylmethyl)-N-methylamino]-2-thenoyl)-L-glutamic acid; growth factor inhibitor; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-trifluoromethyl) propionanilide). Such conjoint treatment may be achieved by way of simultaneous, sequential or separate dosing of the individual components of the treatment.

The pharmaceutical composition may, for example, be in a form suitable for oral administration as a tablet, capsule, pill, powder, sustained release formulations, solution, and suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled n this art. For example, see Remington's Pharmaceutical Sciences, Mack Publishing Company, Easter, Pa., 15$^{th}$ Edition (1975).

The examples and preparations provided below further illustrate and exemplify the compounds of the present invention and methods of preparing such compounds. It is to be understood that the scope of the present invention is not limited in any way by the scope of the following examples and preparations.

Detailed analytical and preparative HPLC chromatography methods referred to in the preparations and examples below are outlined as follows.

Analytical HPLC method 1, 2 and 3: Gilson HPLC equipped with a diode array detector and a MetaChem Polaris 5 um C18-A 20×2.0 mm column; peak detection reported usually in total intensity chromatogram and 210 nm wavelength; solvent A: water with 2% acetonitrile and 0.01% formic acid, solvent B: acetonitrile with 0.05% formic acid; flow rate at 1 mL/min.

Method 1 gradient: 5% to 20% solvent B in 1 min., ramp up to 100% solvent B at 2.25 min., stay at 100% B until 2.5 min., and back to 5% B at 3.75 min.

Method 2 gradient: 5% to 20% solvent B in 1.25 min., ramp up to 50% at 2.5 min., and up to 100% B at 3.25 min., stay at 100% B until 4.25 min., and back to 5% B at 4.5 min.

Method 3 gradient: stay at 0% solvent B until 1.0 min., ramp up to 20% at 2.0 min., up to 100% B at 3.5 min., back to 0% B at 3.75 min.

Analytical HPLC method 4: Hewlett Packard-1050 equipped with a diode array detector and a 150×4 mm Hewlett Packard ODS Hypersil column; peak detection reported at 254 and 300 nm wavelength; solvent A: water with ammonium acetate/acetic acid buffer (0.2 M), solvent B: acetonitrile; flow rate at 3 mL/min.

Method 4 gradient: 0% to 100% B in 10 min., hold at 100% B for 1.5 min.

Preparative HPLC method: Shimadzu HPLC equipped with a diode array detector and a Waters Symmetry or Extera C8 column, 19×50 mm or 30×50 mm; peak detection reported usually at 210 nm wavelength; solvent A: water with 2% acetonitrile and 0.1% formic acid, solvent B: acetonitrile with 0.1% formic acid; flow rate between 18 to 40 mL/min.

General preparative HPLC gradient methods are usually a linear 0 to 5% B to 100% B over 10 to 25 min. Special gradient methods with a narrower gradient window, customized using methods familiar to those skilled in the art, are used for some compounds.

EXAMPLE 1

1A.
4-Chloro-7-isopropyl-7H-pyrrolo[2,3-d]pyrimidine $Cs_2CO_3$ (382 g, 1.2 mol) was added to a solution of 4-Chloro-7H-pyrrolo[2,3-d]pyrimidine (120 g, 0.78 mol) in DMF (1.0 L) at room temperature. The resulting mixture was stirred for 30 min. 2-Iodopropane (267 g, 1.6 mol) was added and the reaction and stirred for 5 h at room temperature. The reaction mixture was filtered and the solid was washed with EtOAc (3×500 mL). The combined filtrates were washed with water (3×500 mL) and brine (3×250 mL), dried ($Na_2SO_4$), filtered, and concentrated in vacuo to afford the title compound as a yellow solid (151 g, 94%). MS: 19.6 (MH+); HPLC Rf: 4.89 min. (HPLC method 4).

1B.  5-Bromo4-chloro-7-isopropyl-7H-pyrrolo[2,3-d]pyrimidine

N-Bromosuccinimide (165 g, 926 mmol) was added to a solution of 4-Chloro-7-isopropyl-7H-pyrrolo[2,3-d]pyrimidine (151 g, 772 mmol) in $CH_2Cl_2$ (1 L). After 12 h the reaction was quenched with saturated aqueous $NaHCO_3$ (500 mL). The layers were separated and the aqueous layer was extracted with $CH_2Cl_2$ (2×500 mL). The combined organic layers were washed with water (3×500 mL) and brine (1×500 mL), dried ($Na_2SO_4$), filtered, and concentrated in vacuo to afford the title compound as a white solid (198 g, 94%). MS: 275.5 (MH+); HPLC Rf: 5.99 min. (HPLC method 4).

1C. (5-Bromo-pyridin-3-yl)-(4-chloro-7-isopropyl-7H-pyrrolo[2,3-d]pyrimidin-5-yl)-methanone n-BuLi (15.3 mL, 2.5 M in Hexane, 38.2 mmol) was added dropwise to a solution of 5-Bromo-4-chloro-7-isopropyl-7H-pyrrolo[2,3-d]pyrimidine (10.0 g, 36.4 mmol) in $Et_2O$ (300 mL) at −78° C. and stirred for 1 h. 5-Bromo-N-methoxy-N-methyl-nicotinamide (8.9 g, 36.4 mmol) was added to the reaction mixture slowly and stirred for 3 h, warmed to room temperature, and stirred for an additional 1 h. The reaction mixture was quenched with saturated aqueous $NH_4Cl$ (200 mL) and stirred for 20 min. The aqueous layer was extracted with EtOAc (3×300 mL) and the combined organic layers were washed with brine (500 mL), dried ($Na_2SO_4$), filtered, and concentrated in vacuo to provide a crude brown solid. Trituration with 2-propanol provided the title compound as a pure off-white solid (7.0 g, 51%). MS: 380.7 (MH+); HPLC Rf: 5.5 min. (HPLC method 4).

1D. (4-Amino-7-isopropyl-7H-pyrrolo[2,3-d]pyrimidin-5-yl)-(5-amino-pyridin-3-yl)-methanone $CuSO_4 \times 5H_2O$ (0.39 g, 1.6 mmol) was added to a suspension of (5-Bromo-pyridin-3-yl)-(4-chloro-7-isopropyl-7H-pyrrolo[2,3-d]pyrimidin-5-yl)-methanone (2.0 g, 5.3 mmol) and $NH_4OH$ (50 mL) and heated to 150° C. and 250 psi in a pressure reactor for 5 h. The reaction mixture was cooled to room temperature and concentrated in vacuo. The crude solid was extracted with hot EtOAc (3×200 mL), filtered, and the combined filtrates were washed with brine (400 mL), dried (MgSO4), filtered, and concentrated in vacuo. Purification by flash column chromatography [(10% $NH_4OH$/MeOH)/ethyl acetate 15:85] afforded the title compound as a pale yellow solid (1.13 g, 73%). MS: 297.2 (MH+); HPLC Rf: 3.1 min. (HPLC method 4).

EXAMPLE 2

N-[5-(4-Amino-7-isopropyl-7H-pyrrolo[2,3-d]pyrimidine-5-carbonyl)-pyridin-3-yl]-3,5-difluoro-benzenesulfonamide 3,5-Difluoro-benzenesulfonyl chloride (19.7 mg, 0.093 mmol) was added to a solution of (4-Amino-7-isopropyl-7H-pyrrolo[2,3-d]pyrimidin-5-yl)-(5-amino-pyridin-3-yl)-methanone (25 mg, 0.084 mmol) in pyridine (0.7 mL). The resulting solution was heated to 40° C. for 16 h. The reaction mixture was concentrated in vacuo and the residue dissolved in DMSO (2 mL) and purified using reverse phase preparative HPLC to furnish the title compound as a white solid. MS: 473.2 (MH+); HPLC Rf: 4.91 min. (HPLC method 4).

EXAMPLE 3

N-[5-(4-Amino-7-isopropyl-7H-pyrrolo[2,3-d]pyrimidine-5-carbonyl)-pyridin-3-yl]-2-chloro-benzenesulfonamide The title compound was prepared from 2-Chloro-benzenesulfonyl chloride (19.6 mg, 0.093 mmol) and (4-Amino-7-isopropyl-7H-pyrrolo[2,3-d]pyrimidin-5-yl)-(5-amino-pyridin-3-yl)-methanone (25 mg, 0.084 mmol) by procedures analogous to those described for the preparation of N-[5-(4-Amino-7-isopropyl-7H-pyrrolo[2,3-d]pyrimidine-5-carbonyl)-pyridin-3-yl]-3,5-difluoro-benzenesulfonamide. MS: 471.2 (MH+); HPLC Rf: 4.71 min. (HPLC method 4).

EXAMPLES 4-16

Example 4-16 listed in the following table were prepared using procedures analogous to those described in Example 2.

| Example | Compound Name | MH+ | HPLC Rf (min) | HPLC method |
|---|---|---|---|---|
| 4 | N-[5-(4-Amino-7-isopropyl-7H-pyrrolo[2,3-d]pyrimidine-5-carbonyl)-pyridin-3-yl]-4-fluoro-benzenesulfonamide | 455.3 | 4.74 | 4 |
| 5 | N-[5-(4-Amino-7-isopropyl-7H-pyrrolo[2,3-d]pyrimidine-5-carbonyl)-pyridin-3-yl]-2-fluoro-benzenesulfonamide | 455.3 | 4.58 | 4 |
| 6 | N-[5-(4-Amino-7-isopropyl-7H-pyrrolo[2,3-d]pyrimidine-5-carbonyl)-pyridin-3-yl]-3-fluoro-benzenesulfonamide | 455.3 | 4.70 | 4 |
| 7 | 3,5-Dimethyl-isoxazole-4-sulfonic acid [5-(4-amino-7-isopropyl-7H-pyrrolo[2,3-d]pyrimidine-5-carbonyl)-pyridin-3-yl]-amide | 456.3 | 4.44 | 4 |
| 8 | N-[5-(4-Amino-7-isopropyl-7H-pyrrolo[2,3-d]pyrimidine-5-carbonyl)-pyridin-3-yl]-4-chloro-benzenesulfonamide | 471.2 | 5.10 | 4 |
| 9 | N-[5-(4-Amino-7-isopropyl-7H-pyrrolo[2,3-d]pyrimidine-5-carbonyl)-pyridin-3-yl]-3-chloro-benzenesulfonamide | 471.2 | 5.06 | 4 |
| 10 | N-[5-(4-Amino-7-isopropyl-7H-pyrrolo[2,3-d]pyrimidine-5-carbonyl)-pyridin-3-yl]-2,4-difluoro-benzenesulfonamide | 473.2 | 4.75 | 4 |
| 11 | N-[5-(4-Amino-7-isopropyl-7H-pyrrolo[2,3-d]pyrimidine-5-carbonyl)-pyridin-3-yl]-2,6-difluoro-benzenesulfonamide | 473.2 | 4.54 | 4 |
| 12 | N-[5-(4-Amino-7-isopropyl-7H-pyrrolo[2,3-d]pyrimidine-5-carbonyl)-pyridin-3-yl]-3-chloro-4-methyl-benzenesulfonamide | 485.2 | 5.40 | 4 |
| 13 | N-[5-(4-Amino-7-isopropyl-7H-pyrrolo[2,3-d]pyrimidine-5-carbonyl)-pyridin-3-yl]-3-chloro-4-fluoro-benzenesulfonamide | 489.2 | 5.20 | 4 |
| 14 | N-[5-(4-Amino-7-isopropyl-7H-pyrrolo[2,3-d]pyrimidine-5-carbonyl)-pyridin-3-yl]-3-trifluoromethyl-benzenesulfonamide | 505.3 | 5.29 | 4 |
| 15 | N-[5-(4-Amino-7-isopropyl-7H-pyrrolo[2,3-d]pyrimidine-5-carbonyl)-pyridin-3-yl]-3,5-dichloro-benzenesulfonamide | 505.2 | 5.51 | 4 |
| 16 | N-[5-(4-Amino-7-isopropyl-7H-pyrrolo[2,3-d]pyrimidine-5-carbonyl)-pyridin-3-yl]-2,4-dichloro-benzenesulfonamide | 505.2 | 5.30 | 4 |

EXAMPLE 17

1-[5-(4-Amino-7-isopropyl-7H-pyrrolo[2,3-d]pyrimidine-5-carbonyl)-pyridin-3-yl]-3-(4-chloro-2-methyl-phenyl)-urea 4-Chloro-1-isocyanato-2-methyl-benzene (93.3 mg, 0.56 mmol) was added to a solution of (4-Amino-7-isopropyl-7H-pyrrolo[2,3-d]pyrimidin-5-yl)-(5-amino-pyridin-3-yl)-methanone (150 mg, 0.51 mmol) in pyridine (5 mL). The mixture was heated to 45° C. for 12 h. The reaction mixture was concentrated in vacuo and the resulting yellow solid was triturated with $CH_2Cl_2$, filtered, and washed with $CH_2Cl_2$. Purification by flash column chromatography [(10% $NH_4OH$/MeOH)/ethyl acetate 2:98] afforded the title compound as a white solid (197 mg, 83%). MS: 464.1 (MH+); HPLC Rf: 5.55 min. (HPLC method 4).

EXAMPLE 18

1-[5-(4-Amino-7-isopropyl-7 H-pyrrolo[2,3-d]pyrimidine-5-carbonyl)-pyridin-3-yl]-3-(2-fluoro-5-methenyl-phenyl)-urea 1-Fluoro-2-isocyanato-4-methyl-benzene (14.1 mg, 0.093 mmol) was added to a solution of (4-Amino-7-isopropyl-7H-pyrrolo[2,3-d]pyrimidin-5-yl)-(5-amino-pyridin-3-yl)-methanone (25 mg, 0.084 mmol) in pyridine (0.7 mL). The mixture was heated to 40° C. for 16 h. The reaction mixture was concentrated in vacuo and the residue was dissolved in DMSO (2 mL) and purified using reverse phase preparative HPLC to furnish the title compound as a white solid (24.1 mg, 63%). MS: 448.2 (MH+); HPLC Rf: 5.38 min. (HPLC method 4).

EXAMPLES 19-39

Example 19-39 listed in the following table were prepared using procedures analogous to those described in Example 18.

| Example | Compound Name | MH+ | HPLC Rf (min) | method |
|---|---|---|---|---|
| 19 | 1-[5-(4-Amino-7-isopropyl-7H-pyrrolo[2,3-d]pyrimidine-5-carbonyl)-pyridin-3-yl]-3-(4-chloro-phenyl)-urea | 450.2 | 5.39 | 4 |
| 20 | 1-[5-(4-Amino-7-isopropyl-7H-pyrrolo[2,3-d]pyrimidine-5-carbonyl)-pyridin-3-yl]-3-(2,4-dichloro-phenyl)-urea | 484.2 | 5.96 | 4 |
| 21 | 1-[5-(4-Amino-7-isopropyl-7H-pyrrolo[2,3-d]pyrimidine-5-carbonyl)-pyridin-3-yl]-3-cyclohexyl-urea | 422.2 | 4.83 | 4 |
| 22 | 1-[5-(4-Amino-7-isopropyl-7H-pyrrolo[2,3-d]pyrimidine-5-carbonyl)-pyridin-3-yl]-3-p-tolyl-urea | 430.2 | 5.12 | 4 |
| 23 | 1-[5-(4-Amino-7-isopropyl-7H-pyrrolo[2,3-d]pyrimidine-5-carbonyl)-pyridin-3-yl]-3-m-tolyl-urea | 430.2 | 5.15 | 4 |
| 24 | 1[5-(4-Amino-7-isopropyl-7H-pyrrolo[2,3-d]pyrimidine-5-carbonyl)-pyridin-3-yl]-3-(2-fluoro-phenyl)-urea | 434.3 | 4.93 | 4 |
| 25 | 1-[5-(4-Amino-7-isopropyl-7H-pyrrolo[2,3-d]pyrimidine-5-carbonyl)-pyridin-3-yl]-3-(3-fluoro-phenyl)-urea | 434.3 | 5.05 | 4 |
| 26 | 1-[5-(4-Amino-7-isopropyl-7H-pyrrolo[2,3-d]pyrimidine-5-carbonyl)-pyridin-3-yl]-3-(4-fluoro-phenyl)-urea | 434.3 | 4.89 | 4 |
| 27 | 1-[5-(4-Amino-7-isopropyl-7H-pyrrolo[2,3-d]pyrimidine-5-carbonyl)-pyridin-3-yl]-3-(3,5-dimethyl-phenyl)-urea | 444.4 | 5.53 | 4 |
| 28 | 1-[5-(4-Amino-7-isopropyl-7H-pyrrolo[2,3-d]pyrimidine-5-carbonyl)-pyridin-3-yl]-3-(4-methoxy-phenyl)-urea | 446.3 | 4.63 | 4 |
| 29 | 1-[5-(4-Amino-7-isopropyl-7H-pyrrolo[2,3-d]pyrimidine-5-carbonyl)-pyridin-3-yl]-3-(2-chloro-phenyl)-urea | 450.3 | 5.28 | 4 |
| 30 | 1-[5-(4-Amino-7-isopropyl-7H-pyrrolo[2,3-d]pyrimidine-5-carbonyl)-pyridin-3-yl]-3-(3-chloro-phenyl)-urea | 450.3 | 5.42 | 4 |
| 31 | 1-[5-(4-Amino-7-isopropyl-7H-pyrrolo[2,3-d]pyrimidine-5-carbonyl)-pyridin-3-yl]-3-(3,5-difluoro-phenyl)-urea | 452.3 | 5.36 | 4 |
| 32 | 1-[5-(4-Amino-7-isopropyl-7H-pyrrolo[2,3-d]pyrimidine-5-carbonyl)-pyridin-3-yl]-3-(3,4-difluoro-phenyl)-urea | 452.3 | 5.20 | 4 |
| 33 | 1-[5-(4-Amino-7-isopropyl-7H-pyrrolo[2,3-d]pyrimidine-5-carbonyl)-pyridin-3-yl]-3-(2,6-difluoro-phenyl)-urea | 452.3 | 4.41 | 4 |
| 34 | 1-[5-(4-Amino-7-isopropyl-7H-pyrrolo[2,3-d]pyrimidine-5-carbonyl)-pyridin-3-yl]-3-(2,4-difluoro-phenyl)-urea | 452.3 | 5.02 | 4 |
| 35 | 1-[5-(4-Amino-7-isopropyl-7H-pyrrolo[2,3-d]pyrimidine-5-carbonyl)-pyridin-3-yl]-3-(2-methoxy-5-methyl-phenyl)-urea | 460.4 | 5.50 | 4 |
| 36 | 1-[5-(4-Amino-7-isopropyl-7H-pyrrolo[2,3-d]pyrimidine-5-carbonyl)-pyridin-3-yl]-3-(3-chloro-4-methyl-phenyl)-urea | 464.3 | 5.77 | 4 |
| 37 | 1-[5-(4-Amino-7-isopropyl-7H-pyrrolo[2,3-d]pyrimidine-5-carbonyl)-pyridin-3-yl]-3-(3,5-dimethoxy-phenyl)-urea | 476.0 | 4.94 | 4 |
| 38 | 1-[5-(4-Amino-7-isopropyl-7H-pyrrolo[2,3-d]pyrimidine-5-carbonyl)-pyridin-3-yl]-3-(3-trifluoromethyl-phenyl)-urea | 484.3 | 5.69 | 4 |
| 39 | 1-[5-(4-Amino-7-isopropyl-7H-pyrrolo[2,3-d]pyrimidine-5-carbonyl)-pyridin-3-yl]-3-(2,3-dichloro-phenyl)-urea | 484.3 | 5.81 | 4 |

EXAMPLE 40

40A. 4-Chloro-7-triisopropylsilanyl-7H-pyrrolo[2,3-d]pyrimidine nBuLi (143 mL, 2.5 M in Hexane, 358 mmol) was added slowly to a solution of 4-Chloro-7H-pyrrolo[2,3-d]pyrimidine (50 g, 326 mmol) in THF (1.0 L) at −78° C. and stirred for 1 h. 3-tert-Butyl-3-chloro-2,2,4,4-tetramethyl-pentane (69.1 g, 358 mmol) was slowly added and the reaction mixture, stirred for 1.5 h at −78° C., warmed to room temperature, and stirred for 3 h. The reaction mixture was quenched with 5% NH$_4$Cl (300 mL), concentrated in vacuo to remove THF, and extracted with CH$_2$Cl$_2$ (4×500 mL). The combined organic extracts were filtered through silica gel and concentrated in vacuo to afford the title compound as a brown oil (100 g, 100%). MS: 310.1 (MH+); HPLC Rf: 9.40 min. (HPLC method 4).

40B. 5-Bromo-4-chloro-7-triisopropylsilanyl-7H-pyrrolo[2,3-d]pyrimidine

N-Bromosuccinimide (60.3 g, 338 mmol) was added to a solution of 4-Chloro-7-triisopropylsilanyl-7H-pyrrolo[2,3-d]pyrimidine (100 g, 323 mmol) in CH$_2$Cl$_2$ (1 L). After 12 h 15 the reaction was quenched with saturated aqueous NaHCO$_3$ (500 mL). The layers were separated and the aqueous layer was extracted with CH$_2$Cl$_2$ (4×500 mL). The combined organic layers were filtered through silica gel and concentrated in vacuo. Purification by flash column chromatography (ethyl acetate/hexanes 1:99) afforded the title compound as a clear solid (89.5 g, 72%). MS: 388.8/390.8 (MH+); HPLC Rf: 9.84 min. (HPLC method 4).

40C. (5-Bromo-pyridin-3-yl)-(4-chloro-7H-pyrrolo[2,3-d]pyrimidin-5-yl)-methanone n-BuLi (11.3 mL, 2.5 M in Hexane, 28.3 mmol) was added dropwise to a solution of 5-Bromo-4-chloro-7-triisopropyl-silanyl-7H-pyrrolo[2,3-d]pyrimidine (10.0 g, 25.7 mmol) in Et$_2$O (250 mL) at −78° C. and stirred for 0.5 h. 5-Bromo-nicotinoyl chloride (6.8 g, 30.8 mmol) was added to the reaction mixture slowly and stirred for 3 h, warmed to room temperature, and stirred for an additional 12 h. The reaction mixture was quenched with saturated aqueous NH$_4$Cl (150 mL) and stirred for 30 min. The aqueous layer was extracted with EtOAc (3×150 mL) and the combined organic layers were washed with brine (300 mL), dried (Na$_2$SO$_4$), filtered, and concentrated in vacuo to provide a crude solid. Trituration with 2-propanol provided the title compound as a pure white solid (7.5 g, 86%). MS: 337.5/339.5 (MH+); HPLC Rf: 4.02 min. (HPLC method 4).

40D. (5-Bromo-pyridin-3-yl)-(4-chloro-7-methyl-7H-pyrrolo[2,3-d]pyrimidin-5-yl)-methanone Cs$_2$CO$_3$ (2.32 g, 7.11 mmol) was added to a suspension of (5-Bromo-pyridin-3-yl)-(4-chloro-7H-pyrrolo[2,3-d]pyrimidin-5-yl)-methanone (1.0 g, 5.93 mmol) in DMF (60 mL) at room temperature. The resulting mixture was stirred for 30 min. MeI (1.01 g, 7.11 mmol) was added and the reaction and stirred for 2 h at room temperature. The reaction mixture was quenched with water (30 mL) and extracted with hot EtOAc (3×50 mL). The combined extracts were washed with brine (100 mL), dried (Na$_2$SO$_4$), filtered, and concentrated in vacuo. Purification by flash column chromatography (ethyl acetate/hexanes 2:8-7:3) provided a solid. The solid was triturated with EtOAc to provide the title compound as an off white solid (1.52 g, 73%). MS: 351.9/353.9 (MH+); HPLC Rf: 4.45 min. (HPLC method 4).

40E. (4-Amino-7-isopropyl-7H-pyrrolo[2,3-d]pyrimidin-5-yl)-(5-amino-pyridin-3-yl)-methanone CuSO$_4$×5H$_2$O (0.92 g, 3.67 mmol) was added to a suspension of (5-Bromo-pyridin-3-yl)-(4-chloro-7-methyl-7H-pyrrolo[2,3-d]pyrimidin-5-yl)-methanone (4.3 g, 12.2 mmol) and NH$_4$OH (125 mL) and heated to 140° C. and 250 psi in a pressure reactor for 6 h. The reaction mixture was cooled to room temperature and filtered. The filtrate was concentrated in vacuo and extracted with hot EtOAc (4×200 mL). The combined organic extracts were washed with brine (500 mL), dried (Na$_2$SO4), filtered, and concentrated in vacuo. Purification by flash column chromatography [ethyl acetate/hexanes 8:2—(20% NH$_4$OH/MeOH)/ethyl acetate 5:95] afforded the title compound as a pale yellow solid (2.27 g, 70%). MS: 269.0 (MH+); HPLC Rf: 2.48 min. (HPLC method 4).

EXAMPLES 41-58

Example 41-58 listed in the following table were prepared using procedures analogous to those described in Example 2.

| Example | Compound Name | MH+ | HPLC Rf (min) | HPLC method |
|---|---|---|---|---|
| 41 | N-[5-(4-Amino-7-methyl-7H-pyrrolo[2,3-d]pyrimidine-5-carbonyl)-pyridin-3-yl]-4-methyl-benzenesulfonamide | 423.2 | 2.4 | 2 |
| 42 | N-[5-(4-Amino-7-methyl-7H-pyrrolo[2,3-d]pyrimidine-5-carbonyl)-pyridin-3-yl]-2-methyl-benzenesulfonamide | 423.2 | 2.4 | 2 |
| 43 | N-[5-(4-Amino-7-methyl-7H-pyrrolo[2,3-d]pyrimidine-5-carbonyl)-pyridin-3-yl]-3-methyl-benzenesulfonamide | 423.2 | 2.4 | 2 |
| 44 | N-[5-(4-Amino-7-methyl-7H-pyrrolo[2,3-d]pyrimidine-5-carbonyl)-pyridin-3-yl]-4-fluoro-benzenesulfonamide | 427.2 | 2.2 | 2 |
| 45 | N-[5-(4-Amino-7-methyl-7H-pyrrolo[2,3-d]pyrimidine-5-carbonyl)-pyridin-3-yl]-2-fluoro-benzenesulfonamide | 427.3 | 2.3 | 2 |
| 46 | N-[5-(4-Amino-7-methyl-7H-pyrrolo-[2,3-d]pyrimidine-5-carbonyl)-pyridin-3-yl]-3-fluoro-benzenesulfonamide | 427.2 | 2.4 | 2 |
| 47 | 3,5-Dimethyl-isoxazole-4-sulfonic acid [5-(4-amino-7-methyl-7H-pyrrolo[2,3-d]pyrimidine-5-carbonyl)-pyridin-3-yl]amide | 428.2 | 2.4 | 2 |
| 48 | N-[5-(4-Amino-7-methyl-7H-pyrrolo[2,3-d]pyrimidine-5-carbonyl)-pyridin-3-yl]-4-chloro-benzenesulfonamide | 443.2 | 2.5 | 2 |

-continued

| Example | Compound Name | MH+ | HPLC Rf (min) | method |
|---|---|---|---|---|
| 49 | N-[5-(4-Amino-7-methyl-7H-pyrrolo[2,3-d]pyrimidine-5-carbonyl)-pyridin-3-yl]-2-chloro-benzenesulfonamide | 443.2 | 2.4 | 2 |
| 50 | N-[5-(4-Amino-7-methyl-7H-pyrrolo[2,3-d]pyrimidine-5-carbonyl)-pyridin-3-yl]-3-chloro-benzenesulfonamide | 443.2 | 2.5 | 2 |
| 51 | N-[5-(4-Amino-7-methyl-7H-pyrrolo[2,3-d]pyrimidine-5-carbonyl)-pyridin-3-yl]-3,5-difluoro-benzenesulfonamide | 445.2 | 2.4 | 2 |
| 52 | N-[5-(4-Amino-7-methyl-7H-pyrrolo[2,3-d]pyrimidine-5-carbonyl)-pyridin-3-yl]-2,6-difluoro-benzenesulfonamide | 445.2 | 2.3 | 2 |
| 53 | N-[5-(4-Amino-7-methyl-7H-pyrrolo[2,3-d]pyrimidine-5-carbonyl)-pyridin-3-yl]-2,4-difluoro-benzenesulfonamide | 445.2 | 2.4 | 2 |
| 54 | N-[5-(4-Amino-7-methyl-7H-pyrrolo[2,3-d]pyrimidine-5-carbonyl)-pyridin-3-yl]-3-chloro-4-methyl-benzenesulfonamide | 457.3 | 2.5 | 2 |
| 55 | N-[5-(4-Amino-7-methyl-7H-pyrrolo[2,3-d]pyrimidine-5-carbonyl)-pyridin-3-yl]-3-chloro-4-fluoro-benzenesulfonamide | 461.2 | 2.5 | 2 |
| 56 | N-[5-(4-Amino-7-methyl-7H-pyrrolo[2,3-d]pyrimidine-5-carbonyl)-pyridin-3-yl]-3-trifluoromethyl-benzenesulfonamide | 477.3 | 2.5 | 2 |
| 57 | N-[5-(4-Amino-7-methyl-7H-pyrrolo[2,3-d]pyrimidine-5-carbonyl)-pyridin-3-yl]-2,5-dichloro-benzenesulfonamide | 478.3 | 2.5 | 2 |
| 58 | N-[5-(4-Amino-7-methyl-7H-pyrrolo[2,3-d]pyrimidine-5-carbonyl)-pyridin-3-yl]-3,5-dichloro-benzenesulfonamide | 478.2 | 2.6 | 2 |

EXAMPLES 59-99

Example 59-99 listed in the following table were prepared using procedures analogous to those described in Example 18.

| Example | Compound Name | MH+ | HPLC Rf (min) | method |
|---|---|---|---|---|
| 59 | 1-[5-(4-Amino-7-methyl-7H-pyrrolo[2,3-d]pyrimidine-5-carbonyl)-pyridin-3-yl]-3-isopropyl-urea | 354.3 | 2.0 | 2 |
| 60 | 1-[5-(4-Amino-7-methyl-7H-pyrrolo[2,3-d]pyrimidine-5-carbonyl)-pyridin-3-yl]-3-propyl-urea | 354.3 | 2.0 | 2 |
| 61 | 1-[5-(4-Amino-7-methyl-7H-pyrrolo[2,3-d]pyrimidine-5-carbonyl)-pyridin-3-yl]-3-phenyl-urea | 388.3 | 2.4 | 2 |
| 62 | 1-[5-(4-Amino-7-methyl-7H-pyrrolo[2,3-d]pyrimidine-5-carbonyl)-pyridin-3-yl]-3-cyclohexyl-urea | 394.4 | 2.4 | 2 |
| 63 | 1-[5-(4-Amino-7-methyl-7H-pyrrolo[2,3-d]pyrimidine-5-carbonyl)-pyridin-3-yl]-3-p-tolyl-urea | 402.3 | 2.5 | 2 |
| 64 | 1-[5-(4-Amino-7-methyl-7H-pyrrolo[2,3-d]pyrimidine-5-carbonyl)-pyridin-3-yl]-3-o-tolyl-urea | 402.4 | 2.4 | 2 |
| 65 | 1-[5-(4-Amino-7-methyl-7H-pyrrolo[2,3-d]pyrimidine-5-carbonyl)-pyridin-3-yl]-3-m-tolyl-urea | 402.4 | 2.5 | 2 |
| 66 | 1-[5-(4-Amino-7-methyl-7H-pyrrolo[2,3-d]pyrimidine-5-carbonyl)-pyridin-3-yl]-3-benzyl-urea | 402.3 | 2.3 | 2 |
| 67 | 1-[5-(4-Amino-7-methyl-7H-pyrrolo[2,3-d]pyrimidine-5-carbonyl)-pyridin-3-yl]-3-(2-fluoro-phenyl)-urea | 406.3 | 2.4 | 2 |
| 68 | 1-[5-(4-Amino-7-methyl-7H-pyrrolo[2,3-d]pyrimidine-5-carbonyl)-pyridin-3-yl]-3-(3-fluoro-phenyl)-urea | 406.2 | 2.4 | 2 |
| 69 | 1-[5-(4-Amino-7-methyl-7H-pyrrolo[2,3-d]pyrimidine-5-carbonyl)-pyridin-3-yl]-3-(4-fluoro-phenyl)-urea | 406.2 | 2.4 | 2 |

-continued

| Example | Compound Name | MH+ | HPLC Rf (min) | method |
|---|---|---|---|---|
| 70 | 1-[5-(4-Amino-7-methyl-7H-pyrrolo[2,3-d]pyrimidine-5-carbonyl)-pyridin-3-yl]-3-(3-cyano-phenyl)-urea | 413.2 | 2.4 | 2 |
| 71 | 1-[5-(4-Amino-7-methyl-7H-pyrrolo[2,3-d]pyrimidine-5-carbonyl)-pyridin-3-yl]-3-(4-cyano-phenyl)-urea | 413.2 | 2.4 | 2 |
| 72 | 1-[5-(4-Amino-7-methyl-7H-pyrrolo[2,3-d]pyrimidine-5-carbonyl)-pyridin-3-yl]-3-benzoyl-urea | 416.2 | 2.4 | 2 |
| 73 | 1-[5-(4-Amino-7-methyl-7H-pyrrolo[2,3-d]pyrimidine-5-carbonyl)-pyridin-3-yl]-3-(3-methyl-benzyl)-urea | 416.2 | 2.4 | 2 |
| 74 | 1-[5-(4-Amino-7-methyl-7H-pyrrolo[2,3-d]pyrimidine-5-carbonyl)-pyridin-3-yl]-3-(4-methyl-benzyl)-urea | 416.3 | 2.4 | 2 |
| 75 | 1-[5-(4-Amino-7-methyl-7H-pyrrolo[2,3-d]pyrimidine-5-carbonyl)-pyridin-3-yl]-3-(2-methyl-benzyl)-urea | 416.3 | 2.4 | 2 |
| 76 | 1-[5-(4-Amino-7-methyl-7H-pyrrolo[2,3-d]pyrimidine-5-carbonyl)-pyridin-3-yl]-3-(2,6-dimethyl-phenyl)-urea | 416.3 | 2.4 | 2 |
| 77 | 1-[5-(4-Amino-7-methyl-7H-pyrrolo[2-3-d]pyrimidine-5-carbonyl)-pyridin-3-yl]-3-(4-ethyl-phenyl)-urea | 416.3 | 2.5 | 2 |
| 78 | 1-[5-(4-Amino-7-methyl-7H-pyrrolo[2,3-d]pyrimidine-5-carbonyl)-pyridin-3-yl]-3-(3,5-dimethyl-phenyl)-urea | 416.4 | 2.5 | 2 |
| 79 | 1-[5-(4-Amino-7-methyl-7H-pyrrolo[2,3-d]pyrimidine-5-carbonyl)-pyridin-3-yl]-3-(3,4-dimethyl-phenyl)-urea | 416.4 | 2.5 | 2 |
| 80 | 1-[5-(4-Amino-7-methyl-7H-pyrrolo[2,3-d]pyrimidine-5-carbonyl)-pyridin-3-yl]-3-(2,5-dimethyl-phenyl)-urea | 416.4 | 2.5 | 2 |
| 81 | 1-[5-(4-Amino-7-methyl-7H-pyrrolo[2,3-d]pyrimidine-5-carbonyl)-pyridin-3-yl]-3-(2,3-dimethyl-phenyl)-urea | 416.3 | 2.4 | 2 |
| 82 | 1-[5-(4-Amino-7-methyl-7H-pyrrolo[2,3-d]pyrimidine-5-carbonyl)-pyridin-3-yl]-3-(2-ethyl-phenyl)-urea | 416.4 | 2.5 | 2 |
| 83 | 1-[5-(4-Amino-7-methyl-7H-pyrrolo[2,3-d]pyrimidine-5-carbonyl)-pyridin-3-yl]-3-(2,4-dimethyl-phenyl)-urea | 416.3 | 2.5 | 2 |
| 84 | 1-[5-(4-Amino-7-methyl-7H-pyrrolo[2,3-d]pyrimidine-5-carbonyl)-pyridin-3-yl]-3-(4-methoxy-phenyl)-urea | 418.3 | 2.4 | 2 |
| 85 | 1-[5-(4-Amino-7-methyl-7H-pyrrolo[2,3-d]pyrimidine-5-carbonyl)-pyridin-3-yl]-3-(2-fluoro-5-methyl-phenyl)-urea | 420.3 | 2.5 | 2 |
| 86 | 1-[5-(4-Amino-7-methyl-7H-pyrrolo[2,3-d]pyrimidine-5-carbonyl)-pyridin-3-yl]-3-(2-chloro-phenyl)-urea | 422.3 | 2.5 | 2 |
| 87 | 1-[5-(4-Amino-7-methyl-7H-pyrrolo[2,3-d]pyrimidine-5-carbonyl)-pyridin-3-yl]-3-(3-chloro-phenyl)-urea | 422.3 | 2.5 | 2 |
| 88 | 1-[5-(4-Amino-7-methyl-7H-pyrrolo[2,3-d]pyrimidine-5-carbonyl)-pyridin-3-yl]-3-(4-chloro-phenyl)-urea | 422.3 | 2.5 | 2 |
| 89 | 1-[5-(4-Amino-7-methyl-7H-pyrrolo[2,3-d]pyrimidine-5-carbonyl)-pyridin-3-yl]-3-(3,5-difluoro-phenyl)-urea | 424.3 | 2.5 | 2 |
| 90 | 1-[5-(4-Amino-7-methyl-7H-pyrrolo[2,3-d]pyrimidine-5-carbonyl)-pyridin-3-yl]-3-(3,4-difluoro-phenyl)-urea | 424.3 | 2.5 | 2 |
| 91 | 1-[5-(4-Amino-7-methyl-7H-pyrrolo[2,3-d]pyrimidine-5-carbonyl)-pyridin-3-yl]-3-(2,6-difluoro-phenyl)-urea | 424.3 | 2.2 | 2 |
| 92 | 1-[5-(4-Amino-7-methyl-7H-pyrrolo[2,3-d]pyrimidine-5-carbonyl)-pyridin-3-yl]-3-(2,4-difluoro-phenyl)-urea | 424.3 | 2.4 | 2 |
| 93 | 1-[5-(4-Amino-7-methyl-7H-pyrrolo[2,3-d]pyrimidine-5-carbonyl)-pyridin-3-yl]-3-(2-methoxy-5-methyl-phenyl)-urea | 432.3 | 2.5 | 2 |
| 94 | 1-[5-(4-Amino-7-methyl-7H-pyrrolo[2,3-d]pyrimidine-5-carbonyl)-pyridin-3-yl]-3-(3-chloro-4-methyl-phenyl)-urea | 436.3 | 2.6 | 2 |

-continued

| Example | Compound Name | MH+ | HPLC Rf (min) | method |
|---|---|---|---|---|
| 95 | 1-[5-(4-Amino-7-methyl-7H-pyrrolo[2,3-d]pyrimidine-5-carbonyl)-pyridin-3-yl]-3-(4-chloro-2-methyl-phenyl)-urea | 436.3 | 2.6 | 2 |
| 96 | 1-[5-(4-Amino-7-methyl-7H-pyrrolo[2,3-d]pyrimidine-5-carbonyl)-pyridin-3-yl]-3-(2,4-dimethoxy-phenyl)-urea | 448.4 | 2.4 | 2 |
| 97 | 1-[5-(4-Amino-7-methyl-7H-pyrrolo[2,3-d]pyrimidine-5-carbonyl)-pyridin-3-yl]-3-(3-trifluoromethyl-phenyl)-urea | 456.3 | 2.6 | 2 |
| 98 | 1-[5-(4-Amino-7-methyl-7H-pyrrolo[2,3-d]pyrimidine-5-carbonyl)-pyridin-3-yl]-3-(2,3-dichloro-phenyl)-urea | 457.3 | 2.6 | 2 |
| 99 | 1-[5-(4-Amino-7-methyl-7H-pyrrolo[2,3-d]pyrimidine-5-carbonyl)-pyridin-3-yl]-3-(2,4-dichloro-phenyl)-urea | 457.3 | 2.6 | 2 |

EXAMPLE 100

100A. (6-Bromo-pyridin-2-yl)-(4-chloro-7-isopropyl-7H-pyrrolo[2,3-d]pyrimidin-5-yl)-methanone The title compound (34.0 g, 69%) was prepared from 5-Bromo-4-chloro-7-isopropyl-7H-pyrrolo[2,3-d]pyrimidine (35.8 g, 130.5 mmol) and 6-Bromo-pyridine-2-carboxylic acid methoxy-methyl-amide (32.0 g, 130.5 mmol) by procedures analogous to those described for the preparation (5-Bromo-pyridin-3-yl)-(4-chloro-7-isopropyl-7H-pyrrolo[2,3-d]pyrimidin-5-yl)-methanone. MS: 380.6 (MH+); HPLC $R_f$: 6.05 min. (HPLC method 4); HPLC purity: 100%.

100B. (4-Amino-7-isopropyl-7H-pyrrolo[2,3-d]pyrimidin-5-yl)-(6-amino-pyridin-2-yl)-methanone The title compound (5.30 g, 85%) was prepared from (6-Bromo-pyridin-2-yl)-(4-chloro-7-isopropyl-7H-pyrrolo[2,3-d]pyrimidin-5-yl)-methanone (8.0 g, 21.3 mmol) by procedures analogous to those described for the preparation of (4-Amino-7-isopropyl-7H-pyrrolo[2,3-d]pyrimidin-5-yl)-(5-amino-pyridin-3-yl)-methanone. MS: 297.1 (MH+); HPLC $R_f$: 370 min. (HPLC method 4); HPLC purity: 100%.

EXAMPLE 101

1-[6-(4-Amino-7-isopropyl-7-H-pyrrolo[2,3-d]pyrimidine-5-carbonyl-2-yl]-3-(2-fluoro-phenyl)-urea 1-Fluoro-2-isocyanato-benzene (83.2 mg, 0.61 mmol) was added to a solution of (4-Amino-7-isopropyl-7H-pyrrolo[2,3-d]pyrimidin-5-yl)-(6-amino-pyridin-2-yl)-methanone (150 mg, 0.51 mmol) in pyridine (2 mL). The mixture was heated to 40° C. in a sealed tube for 12 h. 1-Fluoro-2-isocyanato-benzene (34.7 mg, 0.25 mmol) was added to the reaction mixture and heated to 80° C. in a sealed tube for 1 hour. The reaction mixture was concentrated in vacuo and the resulting solid was triturated with MeOH and filtered to provide a crude yellow solid. Purification by flash column chromatography (hexanes/ethyl acetate 5:5-1:9) afforded the title compound as a yellow solid (197 mg, 83%). MS: 434.4 (MH+); HPLC Rf: 5.08 min. (HPLC method 4); HPLC purity: 100%.

EXAMPLES 102-112

Example 102-112 listed in the following table were prepared using procedures analogous to those described in Example 101.

| Example | Compound Name | MH+ | HPLC Rf (min) | method |
|---|---|---|---|---|
| 102 | 1-[6-(4-Amino-7-isopropyl-7H-pyrrolo[2,3-d]pyrimidine-5-carbonyl)-pyridin-2-yl]-3-(3-fluoro-phenyl)-urea | 434.2 | 5.27 | 4 |
| 103 | 1-[6-(4-Amino-7-isopropyl-7H-pyrrolo[2,3-d]pyrimidine-5-carbonyl)-pyridin-2-yl]-3-(4-fluoro-phenyl)-urea | 434.4 | 5.17 | 4 |
| 104 | 1-[6-(4-Amino-7-isopropyl-7H-pyrrolo[2,3-d]pyrimidine-5-carbonyl)-pyridin-2-yl]-3-(2-chloro-phenyl)-urea | 451.0 | 5.21 | 4 |
| 105 | 1-[6-(4-Amino-7-isopropyl-7H-pyrrolol[2,3-d]pyrimidine-5-carbonyl)-pyridin-2-yl]-3-(3-chloro-phenyl)-urea | 451.0 | 5.50 | 4 |
| 106 | 1-[6-(4-Amino-7-isopropyl-7H-pyrrolo[2,3-d]pyrimidine-5-carbonyl)-pyridin-2-yl]-3-(4-chloro-phenyl)-urea | 451.0 | 5.63 | 4 |
| 107 | 1-[6-(4-Amino-7-isopropyl-7H-pyrrolo[2,3-d]pyrimidine-5-carbonyl)-pyridin-2-yl]-3-(2,4-dichloro-phenyl)-urea | 485.8 | 5.80 | 4 |

-continued

| Example | Compound Name | MH+ | HPLC Rf (min) | method |
|---|---|---|---|---|
| 108 | 1-[6-(4-Amino-7-isopropyl-7H-pyrrolo[2,3-d]pyrimidine-5-carbonyl)-pyridin-2-yl]-3-(2,4-difluoro-phenyl)-urea | 452.3 | 5.22 | 4 |
| 109 | 1-[6-(4-Amino-7-isopropyl-7H-pyrrolo[2,3-d]pyrimidine-5-carbonyl)-pyridin-2-yl]-3-m-tolyl-urea | 430.2 | 5.26 | 4 |
| 110 | 1-[6-(4-Amino-7-isopropyl-7H-pyrrolo[2,3-d]pyrimidine-5-carbonyl)-pyridin-2-yl]-3-(3-trifluoromethyl-phenyl)-urea | 484.2 | 5.74 | 4 |
| 111 | 1-[6-(4-Amino-7-isopropyl-7H-pyrrolo[2,3-d]pyrimidine-5-carbonyl)-pyridin-2-yl]-3-(2-fluoro-5-methyl-phenyl)-urea | 464.2 | 5.45 | 4 |
| 112 | 1-[6-(4-Amino-7-isopropyl-7H-pyrrolo[2,3-d]pyrimidine-5-carbonyl)-pyridin-2-yl]-3-(4-chloro-2-methyl-phenyl)-urea | 464.3 | 5.72 | 4 |

EXAMPLE 113

N-[6-(4-Amino-7-isopropyl-7H-pyrrolo[2,3-d]pyrimidine-5-carbonyl)-pyridin-2-yl]-2-fluoro-benzenesulfonamide 2-Fluoro-benzenesulfonyl chloride (72 mg, 0.37 mmol) was added to a solution of (4-Amino-7-isopropyl-7H-pyrrolo[2,3-d]pyrimidin-5-yl)-(6-amino-pyridin-2-yl)-methanone (100 mg 0.34 mmol) in pyridine (2 mL). The resulting solution was heated to 40° C. in a sealed tube for 12 h. The reaction mixture was concentrated in vacuo and the residue was triturated with MeOH and filtered to provide a crude yellow solid. Purification by flash column chromatography (hexanes/ethyl acetate 5:5-1:9) afforded the title compound as a yellow solid (60 mg, 40%). MS: 455.1 (MH+); HPLC Rf: 4.67 min. (HPLC method 4); HPLC purity: 100%.

EXAMPLES 114-115

Example 114-115 listed in the following table were prepared using procedures analogous to those described in Example 113.

| Example | Compound Name | MH+ | HPLC Rf (min) | method |
|---|---|---|---|---|
| 114 | N-[6-(4-Amino-7-isopropyl-7H-pyrrolo[2,3-d]pyrimidine-5-carbonyl)-pyridin-2-yl]-4-fluoro-benzenesulfonamide | 455.2 | 4.80 | 4 |
| 115 | N-[6-(4-Amino-7-isopropyl-7H-pyrrolo[2,3-d]pyrimidine-5-carbonyl)-pyridin-2-yl]-4-chloro-benzenesulfonamide | 471.1 | 5.14 | 4 |

EXAMPLE 116

(4-Amino-7-isopropyl-7H-pyrrolo[2,3-d]pyrimidin-5-yl)-(2-amino-6-methyl-pyridin-4-yl)-methanone The title compound was prepared from 5-Bromo-4-chloro-7-isopropyl-7H-pyrrolo[2,3-d]pyrimidine (15.8 g, 50.7 mmol) and 2-Chloro-6-methyl-isonicotinoyl chloride (9.6 g, 50.7 mmol) by procedures analogous to those described for the preparation (4-Amino-7-isopropyl-7H-pyrrolo[2,3-d]pyrimidin-5-yl)-(6-amino-pyridin-2-yl)-methanone. MS: 311.2 (MH+); HPLC $R_f$: 3.23 min. (HPLC method 4); HPLC purity: 100%.

EXAMPLE 117

1-[4-(4-Amino-7-isopropyl-7H-pyrrolo[2,3-d]pyrimidine-5-carbonyl)-6-methyl-pyridin-2-yl]-3-(2-fluoro-phenyl)-urea 1-Fluoro-2-isocyanato-benzene (48.5 mg, 035 mmol) was added to a solution of (4-Amino-7-isopropyl-7H-pyrrolo[2,3-d]pyrimidin-5-yl)-(2-amino-6-methyl-pyridin-4-yl)-methanone (100 mg, 0.32 mmol) in pyridine (2 mL). The mixture was stirred for 2 h at room temperature. The reaction mixture was quenched with H$_2$O (2 mL) and concentrated in vacuo. The resulting residue was triturated with MeOH, filtered, and dried to afford the title compound as an off-white solid (104 mg, 72%). MS: 448.3 (MH+); HPLC Rf: 6.36 min. (HPLC method 4).

EXAMPLES 118-129

Example 118-129 listed in the following table were prepared using procedures analogous to those described in Example 117.

| Example | Compound Name | MH+ | HPLC Rf (min) | method |
|---|---|---|---|---|
| 118 | 1-[4-(4-Amino-7-isopropyl-7H-pyrrolo[2,3-d]pyrimidine-5-carbonyl)-6-methyl-pyridin-2-yl]-3-(3-fluoro-phenyl)-urea | 448.3 | 6.23 | 4 |

-continued

| Example | Compound Name | MH+ | HPLC Rf (min) | method |
|---|---|---|---|---|
| 119 | 1-[4-(4-Amino-7-isopropyl-7H-pyrrolo[2,3-d]pyrimidine-5-carbonyl)-6-methyl-pyridin-2-yl]-3-(4-fluoro-phenyl)-urea | 448.3 | 6.08 | 4 |
| 120 | 1-[4-(4-Amino-7-isopropyl-7H-pyrrolo[2,3-d]pyrimidine-5-carbonyl)-6-methyl-pyridin-2-yl]-3-(2-chloro-phenyl)-urea | 464.3 | 5.85 | 4 |
| 121 | 1-[4-(4-Amino-7-isopropyl-7H-pyrrolo[2,3-d]pyrimidine-5-carbonyl)-6-methyl-pyridin-2-yl]-3-(3-chloro-phenyl)-urea | 464.3 | 5.84 | 4 |
| 122 | 1-[4-(4-Amino-7-isopropyl-7H-pyrrolo[2,3-d]pyrimidine-5-carbonyl)-6-methyl-pyridin-2-yl]-3-(4-chloro-phenyl)-urea | 464.3 | 5.77 | 4 |
| 123 | 1-[4-(4-Amino-7-isopropyl-7H-pyrrolo[2,3-d]pyrimidine-5-carbonyl)-6-methyl-pyridin-2-yl]-3-(2,4-dichloro-phenyl)-urea | 498.3 | 6.54 | 4 |
| 124 | 1-[4-(4-Amino-7-isopropyl-7H-pyrrolo[2,3-d]pyrimidine-5-carbonyl)-6-methyl-pyridin-2-yl]-3-(2,4-difluoro-phenyl)-urea | 466.3 | 5.78 | 4 |
| 125 | 1-[4-(4-Amino-7-isopropyl-7H-pyrrolo[2,3-d]pyrimidine-5-carbonyl)-6-methyl-pyridin-2-yl]-3-(4-chloro-2-methyl-phenyl)-urea | 478.4 | 5.99 | 4 |
| 126 | 1-[4-(4-Amino-7-isopropyl-7H-pyrrolo[2,3-d]pyrimidine-5-carbonyl)-6-methyl-pyridin-2-yl]-3-(2-fluoro-5-methyl-phenyl)-urea | 462.4 | 5.89 | 4 |
| 127 | 1-[4-(4-Amino-7-isopropyl-7H-pyrrolo[2,3-d]pyrimidine-5-carbonyl)-6-methyl-pyridin-2-yl]-3-m-tolyl-urea | 444.4 | 6.26 | 4 |
| 128 | 1-[4-(4-Amino-7-isopropyl-7H-pyrrolo[2,3-d]pyrimidine-5-carbonyl)-6-methyl-pyridin-2-yl]-3-(3-trifluoromethyl-phenyl)-urea | 498.4 | 5.83 | 4 |
| 129 | 1-[4-(4-Amino-7-isopropyl-7H-pyrrolo[2,3-d]pyrimidine-5-carbonyl)-6-methyl-pyridin-2-yl]-3-(3,5-difluoro-phenyl)-urea | 466.3 | 6.67 | 4 |

EXAMPLE 130

N-[4-(4-Amino-7-isopropyl-7H-pyrrolo[2,3-d]pyrimidine-5-carbonyl )-6-methyl-pyridin-2-yl]-2-fluoro-benzenesulfonamide 2-Fluoro-benzenesulfonyl chloride (68.9 mg, 035 mmol) was added to a solution of (4-Amino-7-isopropyl-7H-pyrrolo [2,3-d]pyrimidin-5-yl)-(2-amino-6-methyl-pyridin-4-yl)-methanone (100 mg, 0.32 mmol) in pyridine (2 mL). The mixture was stirred for 2 h at room temperature. The reaction mixture was quenched with $H_2O$ (2 mL) and concentrated in vacuo. The resulting residue was triturated with MeOH, filtered, and dried. Purification by flash column chromatography [ethyl acetate/hexanes 3:7—(20% $NH_4OH$/MeOH)/ethyl acetate/hexanes 5:65:30] afforded the title compound as a yellow oil (94 mg, 62%). MS: 469.3 (MH+); HPLC Rf: 4.46 min. (HPLC method 4).

EXAMPLES 131-132

Example 131-132 listed in the following table were prepared using procedures analogous to those described in Example 130.

| Example | Compound Name | MH+ | HPLC Rf (min) | method |
|---|---|---|---|---|
| 131 | N-[4-(4-Amino-7-isopropyl-7H-pyrrolo[2,3-d]pyrimidine-5-carbonyl)-6-methyl-pyridin-2-yl]-4-fluoro-benzenesulfonamide | 469.3 | 4.16 | 4 |
| 132 | N-[4-(4-Amino-7-isopropyl-7H-pyrrolo[2,3-d]pyrimidine-5-carbonyl)-6-methyl-pyridin-2-yl]-2-chloro-benzenesulfonamide | 485.3 | 4.44 | 4 |

EXAMPLE 133

(4-Chloro-7-isopropyl-7H-pyrrolo[2,3-d]pyrimidin-5-yl)-(2-chloro-pyridin-4-yl)-methanone The title compound was prepared from 5-Bromo-4-chloro-7-isopropyl-7H-pyrrolo[2,3-d]pyrimidine (6.5 g, 23.7 mmol) and 2-Chloro-N-methoxy-N-methyl-isonicotinamide (5.7 g, 28.4 mmol) by procedures analogous to those described for the preparation of (5-Bromo-pyridin-3-yl)-(4-chloro-7-isopropyl-7H-pyrrolo[2,3-d]pyrimidin-5-yl)-methanone. MS: 295.8 (MH−); HPLC $R_f$: 2.0 min. (HPLC method 2); HPLC purity: 100%.

EXAMPLE 134

(4-Amino-7-isopropyl-7H-pyrrolo[2,3-d]pyrimidin-5-yl)-(2-amino-pyridin-4-yl)-methanone (4-Chloro-7-isopropyl-7H-pyrrolo[2,3-d]pyrimidin-5-yl)-(2-chloro-pyridin-4-yl)-methanone (6.22 g, 18.5 mmol) was added to a solution of ammonium hydroxide (240 mL) in dioxane (240 mL) and stirred at 45° C. in a sealed tube for 3 days. The reaction mixture was diluted with $CH_2Cl_2$ (100 mL), concentrated in vacuo, dissolved in $CH_2Cl_2$ (200 mL), and washed with water (3×100 mL). The aqueous layer was extracted with hot $CH_2Cl_2$/MeOH (95:5, 3×100 mL) and the combined organic extracts were dried ($Na_2SO_4$), filtered, and concentrated in vacuo to provide the title compound as a yellow solid (3.98 g, 73%). MS: 295.7 (MH$^-$); HPLC R$_f$: 2.0 min. (HPLC method 2).

EXAMPLE 135

1-[4-(4-Amino-7-isopropyl-7H-pyrrolo[2,3-d]pyrimidine-5-carbonyl)-pyridin-2-yl]-3-(2-fluoro-phenyl)-urea 1-Fluoro-2-isocyanato-benzene (0.09 mL, 0.81 mmol) was added to a solution of (4-Amino-7-isopropyl-7H-pyrrolo[2,3-d]pyrimidin-5-yl)-(2-amino-pyridin-4-yl)-methanone (0.20 g, 0.67 mmol) in pyridine (2 mL). The mixture was heated to 80° C. in a sealed tube for 2 h. The reaction mixture was quenched with water (10 mL) and extracted with hot EtOAc/MeOH (95:5, 3×10 mL). The combined organic extracts were dried ($Na_2SO_4$), filtered, and concentrated in vacuo. Purification by flash column chromatography (ethyl acetate/MeOH 99:1) afforded the title compound as a yellow solid (160 mg, 55%). MS: 434.2 (MH$^+$); HPLC R$_f$: 5.83 min. (HPLC method 4); HPLC purity: 98%.

EXAMPLES 136-147

Example 136-147 listed in the following table were prepared using procedures analogous to those described in Example 135.

| Example | Compound Name | MH+ | HPLC Rf (min) | HPLC method |
|---|---|---|---|---|
| 136 | 1-[4-(4-Amino-7-isopropyl-7H-pyrrolo[2,3-d]pyrimidine-5-carbonyl)-pyridin-2-yl]-3-(3-fluoro-phenyl)-urea | 434.4 | 5.83 | 4 |
| 137 | 1-[6-(4-Amino-7-isopropyl-7H-pyrrolo[2,3-d]pyrimidine-5-carbonyl)-pyridin-2-yl]-3-(4-fluoro-phenyl)-urea | 434.4 | 5.79 | 4 |
| 138 | 1-[4-(4-Amino-7-isopropyl-7H-pyrrolo[2,3-d]pyrimidine-5-carbonyl)-pyridin-2-yl]-3-(2-chloro-phenyl)-urea | 450.9 | 2.9 | 2 |
| 139 | 1-[4-(4-Amino-7-isopropyl-7H-pyrrolo[2,3-d]pyrimidine-5-carbonyl)-pyridin-2-yl]-3-(3-chloro-phenyl)-urea | 450.9 | 2.8 | 2 |
| 140 | 1-[4-(4-Amino-7-isopropyl-7H-pyrrolo[2,3-d]pyrimidine-5-carbonyl)-pyridin-2-yl]-3-(4-chloro-phenyl)-urea | 450.8 | 2.8 | 2 |
| 141 | 1-[4-(4-Amino-7-isopropyl-7H-pyrrolo[2,3-d]pyrimidine-5-carbonyl)-pyridin-2-yl]-3-m-tolyl-urea | 430.3 | 5.36 | 4 |
| 142 | 1-[4-(4-Amino-7-isopropyl-7H-pyrrolo[2,3-d]pyrimidine-5-carbonyl)-pyridin-2-yl]-3-(2-trifluoromethyl-phenyl)-urea | 484.5 | 2.7 | 2 |
| 143 | 1-[4-(4-Amino-7-isopropyl-7H-pyrrolo[2,3-d]pyrimidine-5-carbonyl)-pyridin-2-yl]-3-(2,4-dichloro-phenyl)-urea | 485.4 | 3.0 | 2 |
| 144 | 1-[4-(4-Amino-7-isopropyl-7H-pyrrolo[2,3-d]pyrimidine-5-carbonyl)-pyridin-2-yl]-3-(2,4-difluoro-phenyl)-urea | 452.4 | 2.9 | 2 |
| 145 | 1-[4-(4-Amino-7-isopropyl-7H-pyrrolo[2,3-d]pyrimidine-5-carbonyl)-pyridin-2-yl]-3-(2-fluoro-5-methyl-phenyl)-urea | 448.5 | 2.7 | 2 |
| 146 | 1-[4-(4-Amino-7-isopropyl-7H-pyrrolo[2,3-d]pyrimidine-5-carbonyl)-pyridin-2-yl]-3-(3,5-difluoro-phenyl)-urea | 452.4 | 2.9 | 2 |
| 147 | 1-[4-(4-Amino-7-isopropyl-7H-pyrrolo[2,3-d]pyrimidine-5-carbonyl)-pyridin-2-yl]-3-(4-chloro-2-methyl-phenyl)-urea | 464.0 | 2.7 | 2 |

EXAMPLE 148

N-[4-(4-Amino-7-isopropyl-7H-pyrrolo[2,3-d]pyrimidine-5-carbonyl)-pyridin-2yl]-2-fluoro-benzene-sulfonamide 2-Fluoro-benzenesulfonyl chloride (0.11 mL, 0.81 mmol) was added to a solution of (4-Amino-7-isopropyl-7H-pyrrolo[2,3-d]pyrimidin-5-yl)-(2-amino-6-methyl-pyridin4-yl)-methanone (200 mg, 0.67 mmol) in pyridine (2 mL). The mixture was stirred for 2 h at 80° C. The reaction mixture was quenched with $H_2O$ (10 mL) and extracted with hot EtOAC/MeOH (95:5, 3×10 mL). The combined organic extracts were dried ($Na_2SO_4$), filtered, and concentrated in vacuo. Purification by flash column chromatography (ethyl acetate/MeOH 99:1) afforded the title compound as a yellow solid (91 mg, 30%). MS: 455.8 (MH+); HPLC Rf: 5.98 min. (HPLC method 4); HPLC purity: 100%.

EXAMPLES 149-150

Example 149-150 listed in the following table were prepared using procedures analogous to those described in Example 148.

| Example | Compound Name | MH+ | HPLC Rf (min) | method |
|---|---|---|---|---|
| 149 | N-[4-(4-Amino-7-isopropyl-7H-pyrrolo[2,3-d]pyrimidine-5-carbonyl)-pyridin-2-yl]-4-fluoro-benzenesulfonamide | 455.7 | 6.01 | 4 |
| 150 | N-[4-(4-Amino-7-isopropyl-7H-pyrrolo[2,3-d]pyrimidine-5-carbonyl)-pyridin-2-yl]-4-chloro-benzenesulfonamide | 471.0 | 5.87 | 4 |

EXAMPLE 151

(4-Amino-7-isopropyl-7H-pyrrolo[2,3-d]pyrimidin-5-yl)-(4-amino-pyridin-2-yl)-methanone The title compound was prepared from 5-Bromo4-chloro-7-isopropyl-7H-pyrrolo[2,3-d]pyrimidine (6.5 g, 23.7 mmol) and 4-Chloro-pyridine-2-carboxylic acid methoxy-methyl-amide (5.7 g, 28.5 mmol) by procedures analogous to those described for the preparation (4-Amino-7-isopropyl-7H-pyrrolo[2,3-d]pyrimidin-5-yl)-(6-amino-pyridin-2-yl)-methanone. MS:

298.1 (MH$^+$); HPLC R$_f$: 2.55 min. (HPLC method 2); HPLC purity: 99%.

EXAMPLE 152

1-[2-(4-Amino-7-isopropyl-7H-pyrrolo[2,3-d]pyrimidine-5-carbonyl)-pyridin-4-yl]-3-(2-fluoro-phenyl)-urea The title compound was prepared from 1-fluoro-2-isocyanato-benzene (0.05 mL, 0.41 mmol) and (4-Amino-7-isopropyl-7H-pyrrolo[2,3-d]pyrimidin-5-yl)-(4-amino-pyridin-2-yl)-methanone (0.10 g, 0.34 mmol) by procedures analogous to those described for the preparation of 1-[4-(4-Amino-7-isopropyl-7H-pyrrolo[2,3-d]pyrimidine-5-carbonyl)-pyridin-2-yl]-3-(2-fluoro-phenyl)-urea. MS: 434.1 (MH$^+$); HPLC R$_f$: 2.6 min. (HPLC method 2).

EXAMPLES 153-164

Example 153-164 listed in the following table were prepared using procedures analogous to those described in Example 152.

| Example | Compound Name | MH+ | HPLC Rf (min) | method |
|---|---|---|---|---|
| 153 | 1-[2-(4-Amino-7-isopropyl-7H-pyrrolo[2,3-d]pyrimidine-5-carbonyl)-pyridin-4-yl]-3-(3-fluoro-phenyl)-urea | 434.4 | 2.6 | 2 |
| 154 | 1-[2-(4-Amino-7-isopropyl-7H-pyrrolo[2,3-d]pyrimidine-5-carbonyl)-pyridin-4-yl]-3-(4-fluoro-phenyl)-urea | 434.4 | 2.6 | 2 |
| 155 | 1-[2-(4-Amino-7-isopropyl-7H-pyrrolo[2,3-d]pyrimidine-5-carbonyl)-pyridin-4-yl]-3-(2-chloro-phenyl)-urea | 450.4 | 2.6 | 2 |
| 156 | 1-[2-(4-Amino-7-isopropyl-7H-pyrrolo[2,3-d]pyrimidine-5-carbonyl)-pyridin-4-yl]-3-(3-chloro-phenyl)-urea | 450.1 | 2.6 | 2 |
| 157 | 1-[2-(4-Amino-7-isopropyl-7H-pyrrolo[2,3-d]pyrimidine-5-carbonyl)-pyridin-4-yl]-3-(4-chloro-phenyl)-urea | 450.1 | 2.6 | 2 |
| 158 | 1-[2-(4-Amino-7-isopropyl-7H-pyrrolo[2,3-d]pyrimidine-5-carbonyl)-pyridin-4-yl]-3-m-tolyl-urea | 430.5 | 2.8 | 2 |
| 159 | 1-[2-(4-Amino-7-isopropyl-7H-pyrrolo[2,3-d]pyrimidine-5-carbonyl)-pyridin-4-yl]-3-(3-trifluoromethyl-phenyl)-urea | 484.5 | 2.7 | 2 |
| 160 | 1-[2-(4-Amino-7-isopropyl-7H-pyrrolo[2,3-d]pyrimidine-5-carbonyl)-pyridin-4-yl]-3-(2,4-difluoro-phenyl)-urea | 452.1 | 2.7 | 2 |
| 161 | 1-[2-(4-Amino-7-isopropyl-7H-pyrrolo[2,3-d]pyrimidine-5-carbonyl)-pyridin-4-yl]-3-(2,4-dichloro-phenyl)-urea | 484.1 | 2.9 | 2 |
| 162 | 1-[2-(4-Amino-7-isopropyl-7H-pyrrolo[2,3-d]pyrimidine-5-carbonyl)-pyridin-4-yl]-3-(2-fluoro-5-methyl-phenyl)-urea | 448.7 | 5.84 | 4 |
| 163 | 1-[2-(4-Amino-7-isopropyl-7H-pyrrolo[2,3-d]pyrimidine-5-carbonyl)-pyridin-4-yl]-3-(3,5-difluoro-phenyl)-urea | 452.3 | 5.85 | 4 |
| 164 | 1-[2-(4-Amino-7-isopropyl-7H-pyrrolo[2,3-d]pyrimidine-5-carbonyl)-pyridin-4-yl]-3-(4-chloro-2-methyl-phenyl)-urea | 464.3 | 6.02 | 4 |

EXAMPLE 165

N-[2-(4-Amino-7-isopropyl-7H-pyrrolo[2,3-d]pyrimidine-5-carbonyl)-pyridin-4-yl]-2-fluoro-benzenesulfonamide The title compound was prepared from 2-fluoro-benzenesulfonyl chloride (0.53 mL, 0.41 mmol) and (4-Amino-7-isopropyl-7H-pyrrolo[2,3-d]pyrimidin-5-yl)-(4-amino-pyridin-2-yl)-methanone (0.10 g, 0.34 mmol) by procedures analogous to those described for the preparation of N-[4-(4-Amino-7-isopropyl-7H-pyrrolo[2,3-d]pyrimidine-5-carbonyl)-pyridin-2-yl]-2-fluoro-benzenesulfonamide. MS: 455.3 (MH$^+$); HPLC R$_f$: 2.4 min. (HPLC method 2).

EXAMPLES 166-167

Example 166-167 listed in the following table were prepared using procedures analogous to those described in Example 165.

| Example | Compound Name | MH+ | HPLC Rf (min) | method |
|---|---|---|---|---|
| 166 | N-[2-(4-Amino-7-isopropyl-7H-pyrrolo[2,3-d]pyrimidine-5-carbonyl)-pyridin-4-yl]-4-fluoro-benzenesulfonamide | 455.3 | 2.5 | 2 |
| 167 | N-[2-(4-Amino-7-isopropyl-7H-pyrrolo[2,3-d]pyrimidine-5-carbonyl)-pyridin-4-yl]-4-chloro-benzenesulfonamide | 471.3 | 2.6 | 2 |

EXAMPLE 168

2-(Benzhydrylidene-amino)-6,N-dimethoxy-N-methyl-isonicotinamide

2-Chloro-6,N-dimethoxy-N-methyl-isonicotinamide (1.0 g, 4.35 mmol) was added to a mixture of Pd(OAc)$_2$ (0.05 g, 0.22 mmol), BINAP (0.27 g, 0.43 mmol), benzophenone imine (0.88 mL, 5.22 mmol), and cesium carbonate (7.08 g, 21.7 mmol) in toluene (16 mL) and heated to 100° C. for 12 h. Pd(OAc)$_2$ (0.05 g, 0.22 mmol) was added to the reaction mixture and stirred for an additional 1 h at 100° C. The reaction mixture was cooled to room temperature, quenched with EtOAc (200 mL), and filtered. The filtrate was concentrated in vacuo and the residue was purified by flash column chromatography (ethyl acetate/hexanes 65:35) to afford the title compound as a yellow oil (1.53 g, 94%). MS: 376.3 (MH+); HPLC Rf: 6.92 min. (HPLC method 4).

[2-(Benzhydrylidene-amino)-6-methoxy-pyridin-4-yl]-(4-chloro-7-isopropyl-7H-pyrrolo[2,3-d]pyrimidin-5-yl)-methanone n-BuLi (9.40 mL, 2.5 M in Hexane, 23.3 mmol) was added dropwise to a solution of 5-Bromo-4-chloro-7-isopropyl-7H-pyrrolo[2,3-d]pyrimidine (6.25 g, 22.2 mmol) in Et$_2$O (190 mL) at −78° C. and stirred for 1 h. 2-(Benzhydrylideneamino)-6,N-dimethoxy-N-methyl-isonicotinamide (10.0 g, 26.6 mmol) was added to the reaction mixture slowly and stirred for 3h, warmed to room temperature, and quenched with saturated aqueous NH$_4$Cl (200 mL). The aqueous layer was extracted with EtOAc (3×200 mL) and the combined organic layers were dried (Na$_2$SO$_4$), filtered, and concentrated in vacuo to provide a crude solid. Purification by flash column chromatography (ethyl acetate/hexanes 1:1) afforded the title compound as a yellow solid (7.31 mg, 63%). MS: 511.3 (MH+); HPLC Rf: 3.1 min. (HPLC method 3); HPLC purity: 100%.

(4-Amino-7-isopropyl-7 H-pyrrolo[2,3-d]pyrimidin-5-yl )-(2-amino-6-methoxy-pyridin-4-yl)-methanone

[2-(Benzhydrylidene-amino)-6-methoxy-pyridin-4-yl]-(4-chloro-7-isopropyl-7H-pyrrolo[2,3-d]pyrimidin-5-yl)-methanone (7.31 g, 14.3 mmol) was added to a solution of ammonium hydroxide (150 mL) in dioxane (150 mL) and stirred at 45° C. in a sealed tube for 12 h. The reaction mixture was concentrated in vacuo, dissolved in hot CH$_2$Cl$_2$ (150 mL), and washed with water (3×100 mL). The aqueous layer was extracted with CH$_2$Cl$_2$ (3×100 mL) and the combined organic extracts were dried (Na$_2$SO$_4$), filtered, and concentrated in vacuo to provide the title compound as a yellow solid (3.43 g, 73%). MS: 327.2 (MH$^−$); HPLC R$_f$: 2.1 min. (HPLC method 2).

EXAMPLE 169

1-[4-(4-Amino-7-isopropyl-7H-pyrrolo[2,3-d]pyrimidine-5-carbonyl)-6-methoxy-pyridin-2-yl]-3-(2-fluoro-phenyl)-urea 1-Fluoro-2-isocyanato-benzene (0.04 mL, 0.37 mmol) was added to a solution of (4-isopropyl-Amino-7H-pyrrolo[2,3-d]pyrimidin-5-yl)-(2-amino-6-methoxy-pyridin-4-yl)-methanone (0.10 g, 0.31 mmol) in pyridine (2 mL) and stirred in a sealed tube for 2 h at room temperature. The reaction mixture was quenched with water (100 mL) and extracted with hot EtOAc/MeOH (95:5, 3×100 mL). The combined organic extracts were dried (Na$_2$SO$_4$), filtered, and concentrated in vacuo. Purification by flash column chromatography (ethyl acetate/MeOH 99:1) afforded the title compound as a yellow solid (132 mg, 93%). MS: 464.2 (MH$^+$); HPLC R$_f$: 1.7 min. (HPLC method 2); HPLC purity: 100%.

EXAMPLES 170-182

Example 170-182 listed in the following table were prepared using procedures analogous to those described in Example 169.

| Example | Compound Name | MH+ | HPLC Rf (min) | method |
|---|---|---|---|---|
| 170 | 1-[4-(4-Amino-7-isopropyl-7H-pyrrolo[2,3-d]pyrimidine-5-carbonyl)-6-methoxy-pyridin-2-yl]-3-(3-fluoro-phenyl)-urea | 464.3 | 1.7 | 3 |

-continued

| Example | Compound Name | MH+ | HPLC Rf (min) | method |
|---|---|---|---|---|
| 171 | 1-[4-(4-Amino-7-isopropyl-7H-pyrrolo[2,3-d]pyrimidine-5-carbonyl)-6-methoxy-pyridin-2-yl]-3-(4-fluoro-phenyl)-urea | 464.3 | 1.7 | 3 |
| 172 | 1-[4-(4-Amino-7-isopropyl-7H-pyrrolo[2,3-d]pyrimidine-5-carbonyl)-6-methoxy-pyridin-2-yl]-3-(2-chloro-phenyl)-urea | 480.3 | 1.8 | 3 |
| 173 | 1-[4-(4-Amino-7-isopropyl-7H-pyrrolo[2,3-d]pyrimidine-5-carbonyl)-6-methoxy-pyridin-2-yl]-3-(3-chloro-phenyl)-urea | 480.3 | 1.8 | 3 |
| 174 | 1-[4-(4-Amino-7-isopropyl-7H-pyrrolo[2,3-d]pyrimidine-5-carbonyl)-6-methoxy-pyridin-2-yl]-3-(4-chloro-phenyl)-urea | 480.3 | 1.8 | 3 |
| 175 | 1-[4-(4-Amino-7-isopropyl-7H-pyrrolo[2,3-d]pyrimidine-5-carbonyl)-6-methoxy-pyridin-2-yl]-3-m-tolyl-urea | 460.3 | 2.8 | 2 |
| 176 | 1-[4-(4-Amino-7-isopropyl-7H-pyrrolo[2,3-d]pyrimidine-5-carbonyl)-6-methoxy-pyridin-2-yl]-3-(3-trifluoromethyl-phenyl)-urea | 514.3 | 1.8 | 3 |
| 177 | 1-[4-(4-Amino-7-isopropyl-7H-pyrrolo[2,3-d]pyrimidine-5-carbonyl)-6-methoxy-pyridin-2-yl]-3-(2,4-dichloro-phenyl)-urea | 517.2 | 3.0 | 2 |
| 178 | 1-[4-(4-Amino-7-isopropyl-7H-pyrrolo[2,3-d]pyrimidine-5-carbonyl)-6-methoxy-pyridin-2-yl]-3-(2,4-difluoro-phenyl)-urea | 482.2 | 2.8 | 2 |
| 179 | 1-[4-(4-Amino-7-isopropyl-7H-pyrrolo[2,3-d]pyrimidine-5-carbonyl)-6-methoxy-pyridin-2-yl]-3-(2-fluoro-5-methyl-phenyl)-urea | 478.2 | 2.8 | 2 |
| 180 | 1-[4-(4-Amino-7-isopropyl-7H-pyrrolo[2,3-d]pyrimidine-5-carbonyl)-6-methoxy-pyridin-2-yl]-3-(4-chloro-2-methyl-phenyl)-urea | 494.2 | 2.8 | 2 |
| 181 | 1-[4-(4-Amino-7-isopropyl-7H-pyrrolo[2,3-d]pyrimidine-5-carbonyl)-6-methoxy-pyridin-2-yl]-3-(2,6-difluoro-phenyl)-urea | 482.5 | 2.7 | 2 |
| 182 | 1-[4-(4-Amino-7-isopropyl-7H-pyrrolo[2,3-d]pyrimidine-5-carbonyl)-6-methoxy-pyridin-2-yl]-3-(3,5-dichloro-phenyl)-urea | 514.2 | 3.1 | 2 |

EXAMPLE 183

N-[4-(4-Amino-7-isopropyl-7H-pyrrolo[2,3-d]pyrimidine-5-carbonyl)-6-methoxy-pyridin-2-yl]-2-fluoro-benzenesulfonamide 2-Fluoro-benzenesulfonyl chloride (0.05 mL, 0.37 mmol) was added to a solution of (4-Amino-7-isopropyl-7H-pyrrolo[2,3-d]pyrimidin-5-yl)-(2-amino-6-methoxy-pyridin-4-yl)-methanone (100 mg, 0.31 mmol) in pyridine (2 mL) and stirred for 2 h at room temperature. The reaction mixture was quenched with H$_2$O (100 mL) and extracted with hot EtOAC/MeOH (95:5 3×100 mL). The combined organic extracts were cooled to room temperature and the solid was filtered and dried to provide the title compound as a white solid (69 mg, 47%). MS: 485.3 (MH+); HPLC Rf: 2.7 min. (HPLC method 2); HPLC purity: 100%.

EXAMPLES 184-188

Example 184-188 listed in the following table were prepared using procedures analogous to those described in Example 183.

| Example | Compound Name | MH+ | HPLC Rf (min) | method |
|---|---|---|---|---|
| 184 | N-[4-(4-Amino-7-isopropyl-7H-pyrrolo[2,3-d]pyrimidine-5-carbonyl)-6-methoxy-pyridin-2-yl]-4-fluoro-benzenesulfonamide | 485.3 | 2.7 | 2 |
| 185 | N-[4-(4-Amino-7-isopropyl-7H-pyrrolo[2,3-d]pyrimidine-5-carbonyl)-6-methoxy-pyridin-2-yl]-2-chloro-benzenesulfonamide | 501.3 | 2.6 | 2 |
| 186 | N-[4-(4-Amino-7-isopropyl-7H-pyrrolo[2,3-d]pyrimidine-5-carbonyl)-6-methoxy-pyridin-2-yl]-4-chloro-benzenesulfonamide | 501.3 | 2.7 | 2 |
| 187 | N-[4-(4-Amino-7-isopropyl-7H-pyrrolo[2,3-d]pyrimidine-5-carbonyl)-6-methoxy-pyridin-2-yl]-2,6-difluoro-benzenesulfonamide | 504.2 | 2.6 | 2 |

-continued

| Example | Compound Name | MH+ | HPLC Rf (min) | method |
|---|---|---|---|---|
| 188 | N-[4-(4-Amino-7-isopropyl-7H-pyrrolo[2,3-d]pyrimidine-5-carbonyl)-6-methoxy-pyridin-2-yl]-3,5-dichloro-benzenesulfonamide | 535.3 | 2.8 | 2 |

We claim:

1. A compound of the formula 1

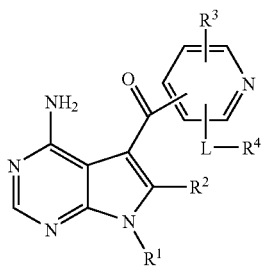

wherein:

L is —N(R)S(O)$_2$—; or —N(R)C(O)N(R)—; wherein each R is H;

each of R$^1$ and R$^2$ is independently H, or (C$_1$-C$_6$)alkyl;

R$^3$ is H, (C$_1$-C$_6$)alkyl, or (C$_1$-C$_6$)alkoxy;

R$^4$ is H, (C$_1$-C$_6$)alkyl, (C$_3$-C$_8$)cycloalkyl, —(CR$^5$R$^6$)$_t$(C$_6$-C$_{10}$)aryl, —(CR$^5$R$^6$)$_t$(C$_2$-C$_{10}$)heteroaryl, or(C$_3$-C$_8$)heterocycloalkyl, wherein t is an integer from 0 to 6; and each of the aforesaid (C$_1$-C$_6$)alkyl, (C$_3$-C$_8$)cycloalkyl, —(CR$^5$R$^6$)$_t$(C$_6$-C$_{10}$)aryl, —(CR$^5$R$^6$)$_t$(C$_2$-C$_{10}$)heteroaryl, and (C$_3$-C$_8$)heterocycloalkyl groups is independently optionally substituted with 1 to 5 R$^9$ groups;

each of R$^5$ and R$^6$ is independently selected from H and (C$_1$-C$_6$)alkyl;

each R$^9$ is independently halo, cyano, trifluoromethoxy, trifluoromethyl, (C$_1$-C$_6$)alkyl, (C$_2$-C$_6$)alkenyl, (C$_2$-C$_6$)alkynyl, or —(CR$^5$R$^6$)$_t$OR$^{10}$, t is independently an integer from 0 to 6; any of the aforesaid —(CR$^5$R$^6$)$_t$ moiety may optionally include a carbon-carbon double or triple bond; and R$^{10}$ is independently hydrogen or (C$_1$-C$_6$)alkyl; or a pharmaceutically acceptable salt thereof.

2. A compound according to claim 1, wherein formula 1 is formula 1D

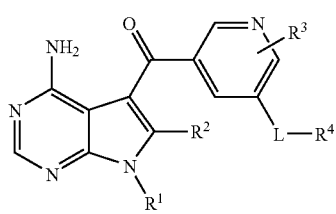

wherein L, R$^1$, R$^2$, R$^3$ and R$^4$ are as set forth in claim 1.

3. A compound according to claim 2, wherein L is —N(R)C(O)N(R)—.

4. A compound according to claim 3, wherein R$^1$ is (C$_1$-C$_6$)alkyl; R$^2$ is H; R$^3$ is H; and R$^4$ is (C$_3$-C$_8$)cycloalkyl or (C$_6$-C$_{10}$)aryl; wherein said (C$_1$-C$_6$)alkyl is optionally substituted with 1 to 5 (C$_1$-C$_6$)alkyl groups and said (C$_3$-C$_8$)cycloalkyl and (C$_6$-C$_{10}$)aryl group are optionally independently substituted with 1 to 5 R$^9$ groups.

5. The compound or salt according to claim 1, wherein said compound is selected from the group consisting of:
   1-[5-(4-Amino-7-isopropyl-7H-pyrrolo[2,3-d]pyrimidine-5-carbonyl)-pyridin-3-yl]-3-(2-fluoro-5-methyl-phenyl)-urea;
   1-[5-(4-Amino-7-isopropyl-7H-pyrrolo[2,3-d]pyrimidine-5-carbonyl)-pyridin-3-yl]-3-(4-chloro-phenyl)-urea;
   1-[5-(4-Amino-7-isopropyl-7H-pyrrolo[2,3-d]pyrimidine-5-carbonyl)-pyridin-3-yl]-3-(2,4-dichloro-phenyl)-urea;
   1-[5-(4-Amino-7-isopropyl-7H-pyrrolo[2,3-d]pyrimidine-5-carbonyl)-pyridin-3-yl]-3-p-tolyl-urea;
   1-[5-(4-Amino-7-isopropyl-7H-pyrrolo[2,3-d]pyrimidine-5-carbonyl)-pyridin-3-yl]-3-(2-fluoro-phenyl)-urea;
   1-[5-(4-Amino-7-isopropyl-7H-pyrrolo[2,3-d]pyrimidine-5-carbonyl)-pyridin-3-yl]-3-(3-fluoro-phenyl)-urea;
   1-[5-(4-Amino-7-isopropyl-7H-pyrrolo[2,3-d]pyrimidine-5-carbonyl)-pyridin-3-yl]-3-(3,5-dimethyl-phenyl)-urea;
   1-[5-(4-Amino-7-isopropyl-7H-pyrrolo[2,3-d]pyrimidine-5-carbonyl)-pyridin-3-yl]-3-(4-methoxy-phenyl)-urea;
   1-[5-(4-Amino-7-isopropyl-7H-pyrrolo[2,3-d]pyrimidine-5-carbonyl)-pyridin-3-yl]-3-(2-chloro-phenyl)-urea;
   1-[5-(4-Amino-7-isopropyl-7H-pyrrolo[2,3-d]pyrimidine-5-carbonyl)-pyridin-3-yl]-3-(3,5-difluoro-phenyl)-urea;
   1-[5-(4-Amino-7-isopropyl-7H-pyrrolo[2,3-d]pyrimidine-5-carbonyl)-pyridin-3-yl]-3-(2,4-difluoro-phenyl)-urea;
   1-[5-(4-Amino-7-isopropyl-7H-pyrrolo[2,3-d]pyrimidine-5-carbonyl)-pyridin-3-yl]-3-(2-methoxy-5-methyl-phenyl)-urea;
   1-[5-(4-Amino-7-isopropyl-7H-pyrrolo[2,3-d]pyrimidine-5-carbonyl)-pyridin-3-yl]-3-(4-chloro-2-methyl-phenyl)-urea;
   1-[5-(4-Amino-7-isopropyl-7H-pyrrolo[2,3-d]pyrimidine-5-carbonyl)-pyridin-3-yl]-3-(3,5-dimethoxy-phenyl)-urea; and
   1-[5-(4-Amino-7-isopropyl-7H-pyrrolo[2,3-d]pyrimidine-5-carbonyl)-pyridin-3-yl]-3-(3-trifluoromethyl-phenyl)-urea.

6. A pharmaceutical composition comprising at least one compound or salt of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,595,325 B2 | Page 1 of 1 |
| APPLICATION NO. | : 11/140411 | |
| DATED | : September 29, 2009 | |
| INVENTOR(S) | : Marx et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 766 days.

Signed and Sealed this
Eleventh Day of January, 2011

David J. Kappos
*Director of the United States Patent and Trademark Office*